United States Patent
Di Francesco et al.

(10) Patent No.: US 10,933,078 B2
(45) Date of Patent: Mar. 2, 2021

(54) CYCLIC DINUCLEOTIDES AS AGONISTS OF STIMULATOR OF INTERFERON GENE DEPENDENT SIGNALLING

(71) Applicant: Board of Regents, The University of Texas System, Austin, TX (US)

(72) Inventors: Maria Emilia Di Francesco, Houston, TX (US); Philip Jones, Houston, TX (US); Michael A. Curran, Pearland, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/484,179

(22) PCT Filed: Feb. 21, 2018

(86) PCT No.: PCT/US2018/019015
§ 371 (c)(1),
(2) Date: Nov. 20, 2019

(87) PCT Pub. No.: WO2018/156625
PCT Pub. Date: Aug. 30, 2018

(65) Prior Publication Data
US 2019/0358254 A1 Nov. 28, 2019

Related U.S. Application Data

(60) Provisional application No. 62/461,642, filed on Feb. 21, 2017.

(51) Int. Cl.
*A61K 31/7084* (2006.01)
*A61P 35/00* (2006.01)
*C07H 21/02* (2006.01)
*C07H 21/04* (2006.01)

(52) U.S. Cl.
CPC .......... *A61K 31/7084* (2013.01); *A61P 35/00* (2018.01); *C07H 21/02* (2013.01); *C07H 21/04* (2013.01)

(58) Field of Classification Search
None
See application file for complete search history.

(56) References Cited

U.S. PATENT DOCUMENTS

| 10,364,266 B2 * | 7/2019 | Adams ................ C07F 9/65746 |
| 2016/0068560 A1 | 3/2016 | Patel |
| 2019/0062365 A1 * | 2/2019 | Katibah ............... A61K 39/395 |

FOREIGN PATENT DOCUMENTS

| WO | 2013185052 | 12/2013 |
| WO | 2014093936 | 6/2014 |
| WO | 2014189805 | 11/2014 |
| WO | 2014189806 | 11/2014 |
| WO | 2015185565 | 12/2015 |
| WO | 2016096174 | 6/2016 |
| WO | 2016096577 | 6/2016 |
| WO | 2016120305 | 8/2016 |
| WO | 2016145102 | 9/2016 |
| WO | 2018156625 | 8/2018 |

OTHER PUBLICATIONS

Corrales, L. et al., "Endogenous and Pharmacologic Targeting of the STING Pathway in Cancer Immunotherapy", Cytokine, 77:245-7, (2016).
Corrales, L. et al., "The Host STING Pathway at the Interface of Cancer and Immunity", J Clin Invest., 126 (7):2404-11, (2016).
Fu, J. et al., "STING Agonist Formulated Cancer Vaccines Can Cure Established Tumors Resistant to PD-1 Blockade", Sci Transl Med., 7(283):283ra52, (2015).
International Application No. PCT/US2018/019015; International Preliminary Report on Patentability, date of issuance Aug. 27, 2019; 14 pages.
International Application No. PCT/US2018/019015; International Search Report and Written Opinion of the International Searching Authority, dated Jun. 21, 2018; 11 pages.
Woo, S. et al., "The STING Pathway and the T Cell-Inflamed Tumor Microenvironment", Trends Immunol., 36 (4):250-6, (2015).
Zhao, J. et al., "Thiophosphate Analogs of c-di-GMP: Impact on Polymorphism", Nucleosides Nucleotides and Nucleic Acids., 28(5):352-78, (2009).

* cited by examiner

*Primary Examiner* — Brian J Davis
(74) *Attorney, Agent, or Firm* — Dennis A. Bennett; Cynthia Hathaway; John Desper

(57) ABSTRACT

Disclosed herein are new cyclic dinucleotide compounds and compositions and their application as pharmaceuticals for the treatment of disease. Methods of modulation of immune response to disease, and induce Stimulator of Interferon Genes (STING) dependent type I interferon production and co-regulated genes in a human or animal subject are also provided for the treatment diseases such as cancer, particularly metastatic solid tumors and lymphomas, inflammation, allergic and autoimmune disease, infectious disease, and for use as anti-viral agents and vaccine adjuvants.

28 Claims, No Drawings

CYCLIC DINUCLEOTIDES AS AGONISTS OF STIMULATOR OF INTERFERON GENE DEPENDENT SIGNALLING

This application claims the benefit of priority of U.S. Provisional Application No. 62/461,642, filed Feb. 21, 2017, the contents of which are incorporated by reference as if written herein in their entirety.

Disclosed herein are new cyclic dinucleotide compounds and compositions and their application as pharmaceuticals for the treatment of disease, and methods of modulating immune response to disease, and induce Stimulator of Interferon Genes (STING) dependent type I interferon production and co-regulated genes. Methods of modulation of STING activity in a human or animal subject are also provided for the treatment of diseases such as cancer, particularly metastatic solid tumors and lymphomas, inflammation, allergic and autoimmune disease, infectious disease, and for use as vaccine adjuvants.

Vertebrates are constantly threatened by the invasion of microorganisms and have evolved mechanisms of immune defence to eliminate infective pathogens. In mammals, this immune system comprises two branches; innate immunity and adaptive immunity. The innate immune system is the first line of defence which is initiated by Pattern Recognition Receptors (PRRs) which detect ligands from the pathogens as well as damage associated molecular patterns (Tokeuchi, O. et al., *Cell* 2010, 140, 805-820). A growing number of these receptors have been identified, including Toll-like receptors (TLRs), C-type lectin receptors, retinoic acid inducible gene I (RIG-1)-like receptors and NOD-like receptors (NLRs) and also double stranded DNA sensors. Activation of PRRs leads to up-regulation of genes involved in the inflammatory response. This response utilizes such agents as: type 1 interferons, pro-inflammatory cytokines and chemokines, which suppress pathogen replication and facilitate adaptive immunity.

The adaptor protein STING (Stimulator of Interferon Genes), also known as TMEM 173, MPYS, MITA and ERIS, has been identified as a central signalling molecule in the innate immune response to cytosolic nucleic acids (Ishikawa, H.; Barber, G. N. *Nature* 2008, 455, 674-678; WO2013/1666000). Activation of STING results in up-regulation of IRFβ and NFKB pathways leading to induction of interferon-β and other cytokines. STING is critical for responses to cytosolic DNA of pathogen or host origin, and of unusual nucleic acids called Cyclic Dinucleotides (CDNs). Initially characterized as ubiquitous bacterial secondary messengers, CDNs [cyclic di-GMP (guanosine 5'-monophosphate) (CDG), cyclic di-AMP (adenosine 5'-monophosphate) (CDA), and cyclic GMP-AMP (cGAMP)] constitute a class of pathogen-associated molecular pattern molecules (PAMPs) that activate the TBK1/interferon regulatory factor 3 (IRF3)/type 1 interferon (IFN) signaling axis via the cytoplasmic pattern recognition receptor stimulator of interferon genes (STING). Bacterial CDNs, such as CDG are symmetrical molecules characterised by two 3', 5' phophodiester linkages.

Direct activation of STING by bacterial CDNs has recently been confirmed through X-ray crystallography (Burdette, D. L.; Vance, R. E. *Nature Immunology* 2013, 14, 19-26; Cai, X. et al. *Molecular Cell* 2014, 54, 289-296). More recently, the response to cytosolic DNA has been elucidated and shown to involve generation, by an enzyme called cyclic GMP-AMP synthase (cGAS, previously known as C6orf150 or MB21D1), of a novel mammalian CDN signalling molecule identified as cGAMP, which then activates STING. Unlike bacterial CDNs, cGAMP is an unsymmetrical molecule characterised by its mixed 2',5' and 3',5' phosphodiester linkages. (Gao, P. et al. *Cell* 2013, 153, 1-14).

Interferon was first described as a substance which could protect cells from viral infection (Isaacs, A.; Lindemann, J. *Proc. Royal Soc. Lon. Ser. B. Biol. Sci.* 1957, 147, 258-267). Interferons belong to the class of small proteins known as cytokines, which are implicated in intercellular signalling. In humans, the type I interferons are a family of related proteins encoded by genes on chromosome 9 and encoding at least 13 isoforms of interferon alpha (IFNα) and one isoform of interferon beta (IFNβ). Recombinant IFNα was the first approved biological therapeutic and has become an important therapy in viral infections and in cancer. As well as direct antiviral activity on cells, interferons are known to be potent agonists of the immune response, acting on cells of the immune system.

Administration of a small molecule compound which could stimulate the innate immune response, including the activation of type I interferons and other cytokines, could become an important strategy for the treatment or prevention of human diseases including viral infections. Compounds capable of stimulating the immune response may be useful not only in infectious diseases but also in cancer (Krieg, *Curr. Oncol. Rep.* 2004, 6(2), 88-95), allergic diseases (Moisan J. et al. *Am. J Physiol. Lung CellMol. Physiol.* 2006, 290, 1987-1995), other inflammatory conditions such as irritable bowel disease (Rakoff-Nahoum, S. et al. *Cell* 2004, 23, 118(2), 229-241), and as vaccine adjuvants (Persing, D. H. et al. *Trends Microbiol.* 2002, 10(10 Suppl), S32-S37).

Induction of type 1 interferons by activation of STING, may offer benefit in treatment of allergic diseases such as asthma and allergic rhinitis (Huber, J. P. et al. *J. Immunol.* 2010, 185, 813-817). Recent evidence has been accumulated to suggest that allergen-reactive type 2 helper T cells (Th2) play a triggering role in the activation and/or recruitment of IgE antibody-producing B cells, mast cells and eosinophils, all of which are involved in the allergic inflammation. Th2 responses are associated with raised levels of IgE, which, via its effects on mast cells, promotes a hypersensitivity to allergens, resulting in the symptoms seen, for example, in allergic rhinitis and asthma. In healthy individuals the immune-response to allergens is more balanced with a mixed Th2/Th1 and regulatory T cell response. Induction of type 1 interferons have been shown to result in reduction of Th2-type cytokines in the local environment and promote Th1/Treg responses.

Activation of the stimulator of interferon genes (STING) pathway has been identified as one of the key determinants in the generation of the spontaneous T-cell response in vivo. The STING pathway is activated by tumor-derived DNA in the cytosol of dendritic cells (DCs), which in turn results in increased levels of cGAMP. Antigen-presenting cells (APCs) such as DCs are implicated in the antitumor T cell response pathway. Upon exposure to immune danger signals, DCs act as potent T cell stimulators, via induction of cGAS, followed by production of cGAMP, which in turn binds to STING. This pathway induces the phenotypic maturation of DCs, followed by the production of type I interferon and other cytokines. Activation of STING induces transcription of numerous host defence genes, resulting in the production of interferon beta, chemokine release and ultimately priming of antigen-specific T-cells, thus eliciting spontaneous anti-tumor T cell response. Innate immune activation by STING agonists in the tumor microenvironment leads to vascular disruption and rapid tumor collapse, which is followed by T cell-mediated adaptive immunity against residual disease. Pharmacological stimulation of the STING pathway with chemically modified cyclic dinucleotides has proven therapeutically efficacious preclinically against tumors in relevant in vivo models, and offers great promise in the clinical setting, with the first STING agonists currently in Phase I studies in patients with metastatic solid tumors or lymphomas. Intratumoral injection of an optimized STING agonist is currently being tested clinically in a phase I clinical trial in advanced cancer patients (NCT02675439).

Induction of IFN in *Listeria*-infected cells is STING-dependent, and it is lost in goldenticket mice harboring a mutant STING allele. Other observations, including the CDG-STING cocrystal structures, demonstrated that cytosolic microbial CDNs bind to STING to elicit an IFN and proinflammatory signaling cascade. The STING signaling pathway has emerged as a central TLR-independent mediator of host innate defense stimulated by cytosolic nucleic acids, either through direct binding of exogenous CDNs from bacteria or through binding of a structurally distinct CDN produced by a host cGAS in response to cytosolic double-stranded DNA (dsDNA). The STING pathway represents a central node linking cytosolic nucleic acids to a transcriptional response resulting in a MyD88-independent production of type I IFN.

Modulation of STING holds promise for the development of compounds with antiviral activity. Recognition of pathogens is mainly mediated by PRRs, including TLRs, RIG-I-like receptors (RLRs) and NOD-like receptors (NLRs) (Takeuchi, O. et al. *Cell* 2010, 140, 805-820), that trigger signal cascades to upregulate the expression of various cytokines. In the case of viral infection, endosomal TLRs and cytoplasmic RLRs detect viral DNAs or RNAs and induce the production of type I IFN, which are potent inhibitors of viral replication (Gitlin, L. et al. *PNAS USA* 2006, 103, 8459-8464; Kato, H. et al. *Nature Immunol.* 2005, 23, 19-28; Kato, H. et al. *Nature* 2006, 441, 101-105). STING has been shown to activate downstream transcription factors STAT6 and IRF3 through TBK1, which are responsible for antiviral response and innate immune response against intracellular pathogen. It has been recently reported that, in response to viral infection, STING activates STAT6 (signal transducer and activator of transcription 6) to induce (Th2-type), increase (IL-12) or decrease (IL-10) production of various cytokines, including the chemokines CCL2, CCL20, and CCL26 (Chen, H. et al. *Cell* 2011, 147, 436-446).

Compounds and pharmaceutical compositions, certain of which have been found to modulate STING activity have been discovered, together with methods of synthesizing and using the compounds including methods for the treatment of STING-mediated diseases in a patient by administering the compounds.

The present invention also relates to new adjuvants and their uses in pharmaceutical compositions, such as vaccines. In particular, the present invention provides new compounds useful as adjuvants and/or immunomodulators for prophylactic and/or therapeutic vaccination in the treatment of infectious diseases, inflammatory diseases, autoimmune diseases, tumours, allergies as well as for the control of fertility in human or animal populations.

Vaccination has become the most cost-effective measure to prevent infections. However, there are still many diseases for which vaccines are not yet available or the available vaccines are not completely satisfactory due to low efficacy, high reactogenicity, poor stability and/or high costs. Thus, there is still an urgent need for both new and improved vaccines.

Recent findings suggest that vaccines can also be used in the immunotherapy of transmissible diseases. Furthermore, vaccines can be used in prophylaxis or immunotherapy of autoimmune diseases, inflammatory diseases, tumours, allergies and for the control of fertility in human and/or animal populations.

The use of optimal adjuvants plays a crucial role in vaccination. Antigens administered without adjuvant only rarely mediate an adequate immune response. In addition, not only the strength but also the quality of the elicited immune response matters. Stimulation of an incorrect immunization pattern may lead to immunopathological reactions and exacerbation of the symptoms of infection. In this context, the adjuvant can help to assist the desired immune response. In other words, an adjuvant can modulate the immune response or redirect the immune response to balance the immune response in the desired direction.

Substances referred to as "adjuvants" are those which are added and/or co-formulated in an immunization to the actual antigen (i.e. the substance which provokes the desired immune response) in order to enhance the humoral and/or cell-mediated immune response ("Lexikon der Biochemie und Molekularbiologie", 1. Band, Spektrum, Akademischer Verlag 1995). That is, adjuvants are compounds having immunopotentiating properties, in particular, when co-administered with antigens. The use of many adjuvants is based solely on experience, and the effect can neither be accurately explained nor predicted. The following groups of adjuvants are traditionally used in particular: aluminum hydroxide, emulsions of mineral oils, saponins, detergents, silicon compounds, thiourea, endotoxins of gram-negative bacteria, exotoxins of gram-positive bacteria, killed or attenuated living bacteria or parts thereof.

As adjuvants which may be useful in mucosal vaccination the following have been described: The MALP-2 molecule and bisacyloxypropylcysteine-conjugates thereof, e.g. a bis-palmitoyloxypropylcysteine-PEG molecule is known to represent potent stimulants for macrophages. The usefulness of MALP-2 as an adjuvant was shown previously, see e.g. WO2004/009125 and WO2003/084568. In particular, it was demonstrated that MALP-2 can act as an effective mucosal adjuvant enhancing the mucosal immune response, e.g. fostering an enhanced expression of antigen-specific IgA antibodies.

Furthermore, it was shown that MALP-2 can activate dendritic cells and B-cells, both play an important role in the induction of a specific humoral immune response. In addition, preliminary studies demonstrate that a combination of biologically active HIV-1 tat protein and synthetic MALP-2 may be a promising vaccine with the MALP-2 component as an effective mucosal adjuvant.

There has been an intensive search in recent years for novel adjuvants, including those for the mucosal administration route. Only a few substances have been found to be able to enhance mucosal responses. Among these, some act as carriers to which the antigens must be bound or fused thereto. Far fewer universally employable "true" adjuvants which are admixed to the antigens have been found, as outlined above.

Prokaryotic as well as eukaryotic cells use various small molecules for cell signaling and intra- and intercellular communication. For example, cyclic nucleotides like cGMP, cAMP, etc. are known to have regulatory and initiating activity in pro- and eukaryotic cells. While in eukaryotic cells cAMP and cGMP are used as signalling molecules, prokaryotic cells utilize cyclic di-nucleoside mono phosphate molecules, in particular CDG, beside cAMP.

The condensation of two GTP molecules is catalyzed by the enzyme diguanylate cyclase (DGC) to give CDG, which has demonstrated anti-microbial activity, and which may be used to prevent or combat pathogens. Moreover, CDG acts as a key bacterial regulator: in bacterial cells, CDG regulates the expression of genes and the biosynthesis of exo-polysaccharides. Further, CDG has not been implicated in any eukaryotic biochemical pathway. Since interacting ligands of CDG are expressed throughout the various genera of bacteria, it is assumed that most bacteria use CDG as a regulatory molecule.

Bacterial CDNs and their analogues have consequently attracted interest as potential vaccine adjuvants (Libanova R. et al. *Microbial Biotechnology* 2012, 5, 168-176; WO2007/054279, WO2005/087238). In WO 2005/087238, it has been speculated that CDG or analogs thereof can stimulate or enhance immune or inflammatory response in a patient or can enhance the immune response to a vaccine by serving as an adjuvant. Further, it is speculated that CDG or its analogs may be used as active ingredient in compositions for treating injuries, diseases, disorders and conditions that result in neurodegeneration. Therein, data are provided showing that cyclic diGMP does not modulate DC endocytic activity but may activate dendritic cells due to induction of expression of co-stimulatory molecules. Further, data are provided showing that occasionally CDG may upregulate immunostimulatory capacity of dendritic cells. Further, data are provided showing that CDG in high doses may activate T-cells in vitro when mixed with dendritic cells. However, any enhancement of immune or inflammatory responses in a patient or enhancement of the immune response to a vaccine by serving as an adjuvant is not shown, rather it is speculated therein that there are some data which may indicate for an increased presentation of antigen through stimulation of HLA-DR. Further, no immunomodulatory action of cyclic diGMP is shown in said document. Hence, this document merely speculates about any immunomodulatory, in particular, about any enhanced immune response by serving as an adjuvant. As discussed before, an adjuvant is a compound able to provoke or enhance the humoral and/or cell mediated immune response against an active antigen. No data are provided in WO 2005/087238 showing an immune response against an active antigen using CDG as adjuvant for enhancing or eliciting or modulating said immune response. In addition, it is noted that said document only provides information regarding CDG but not with respect to any other analogs of cyclic diGMP.

The discovery of the STING pathway, and CDNs that activate it opened up several new possibilities for the development of vaccine adjuvants. STING agonists would be candidates for clinical testing as adjuvants and as stimulants for anticancer immune activity. DMXAA, which markedly shrinks cancer in mouse model systems by activating the innate immune response, is a STING agonist that activates mouse STING (mSTING) but not hSTING. To test the therapeutic hypothesis that STING agonists will be effective for cancer treatment or as vaccine adjuvants, molecules that are active in humans are required. Analogues to cGAMP that are resistant to its activity have been tested for use as vaccine adjuvants (Li, L. et al. *Nature Chem. Biol.* 2014, 10, 1043-1048).

There is a need to provide new compounds useful as adjuvants for use with vaccines. In particular, there is a need for adjuvants which can elicit a strong immune response which represent a balanced or adjusted immune response involving both humoral and cellular components, thus, allowing effective prophylaxis or treatment of various diseases and conditions, specifically of infectious diseases or cancer.

Thus, an object of the present disclosure is the provision of adjuvants which can elicit, enhance, or modulate (pre-existing) immune response in an individual or subject. In particular, the disclosure is directed towards development of a range of novel, highly active adjuvants, particularly, but not limited to, mucosal adjuvants which are non-toxic for humans and which can be employed with a wide variety of active ingredients to be assisted in conventional or novel vaccines such as, in particular, prophylactic or therapeutic vaccines, including cancer and DNA vaccines.

In certain embodiments of the present invention, compounds have structural Formula Ia:

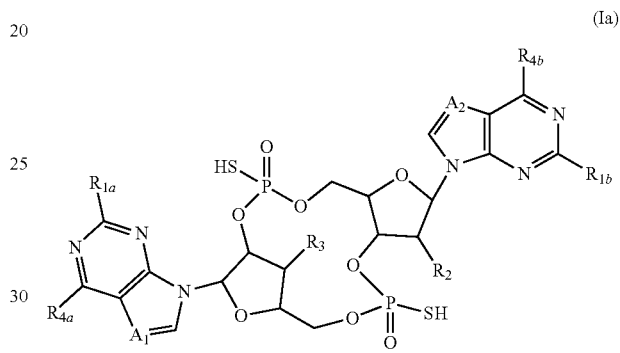

(Ia)

or a salt, ester, tautomer, or prodrug thereof, wherein:
$A_1$ and $A_2$ are independently selected from CH and N;
$R_{1a}$ and $R_{1b}$ are independently selected from H and $NH_2$;
$R_2$ is selected from OH, F, Cl, $N_3$, and $NH_2$;
$R_3$ is selected from OH, F, Cl, $N_3$, and $NH_2$;
$R_{4a}$ and $R_{4b}$ are independently selected from $NH_2$, OH, $NHR_5$, and $OR_5$; and
$R_5$ is independently selected from methyl, ethyl, and propyl; with the provisos that:
when $A_1$ is CH, then $R_{4a}$ is not $NHR_5$ or $OR_5$;
when $A_2$ is CH, then $R_{4b}$ is not $NHR_5$ or $OR_5$; and
when $A_1$ and $A_2$ are both N, then at least one of $R_2$ and $R_3$ is not OH.

Also provided are all stereoisomers, including enantiomers and diastereomers, of compounds of Formula Ia.

In certain embodiments of the present invention, compounds have structural Formula

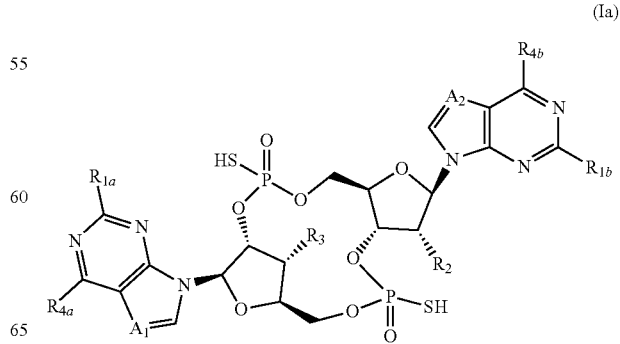

(Ia)

or a salt, ester, tautomer, or prodrug thereof, wherein:

$A_1$ and $A_2$ are independently selected from CH and N;
$R_{1a}$ and $R_{1b}$ are independently selected from H and $NH_2$;
$R_2$ is selected from OH, F, Cl, $N_3$, and $NH_2$;
$R_3$ is selected from OH, F, Cl, $N_3$, and $NH_2$;
$R_{4a}$ and $R_{4b}$ are independently selected from $NH_2$, OH, $NHR_5$, and $OR_5$; and
$R_5$ is independently selected from methyl, ethyl, and propyl; with the provisos that:
  when $A_1$ is CH, then $R_{4a}$ is not $NHR_5$ or $OR_5$;
  when $A_2$ is CH, then $R_{4b}$ is not $NHR_5$ or $OR_5$; and
  when $A_1$ and $A_2$ are both N, then at least one of $R_2$ and $R_3$ is not OH.

Certain compounds disclosed herein may possess useful STING modulating activity, and may be used in the treatment or prophylaxis of a disease or condition in which STING plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for modulating STING. Other embodiments provide methods for treating a STING-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the agonism of STING.

It will be appreciated by a person in the chemical arts that compounds of Formula (Ia) possess several asymmetric, tetrahedral atoms. Formula (Ia) embraces compounds that possess all possible combinations of absolute stereochemistry at the various asymmetric, tetrahedral atoms. Due to the nonidentical substitution at the two tetrahedral phosphorus atoms, each atom represents a center of chirality. Formula (Ia) embraces compounds that possess all possible combinations of absolute stereochemistry at the two asymmetric, tetrahedral phosphorus atoms.

In certain embodiments of the present invention, compounds have structural Formula IIa:

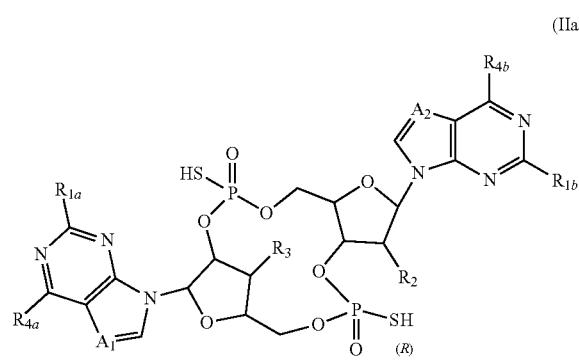

(IIa)

or a salt, ester, tautomer, or prodrug thereof, wherein:
$A_1$ and $A_2$ are independently selected from CH and N;
$R_{1a}$ and $R_{1b}$ are independently selected from H and $NH_2$;
$R_2$ is selected from OH, F, and Cl;
$R_3$ is OH;
$R_{4a}$ and $R_{4b}$ are independently selected from $NH_2$ and OH; and
when $A_1$ and $A_2$ are both N, then $R_2$ is not OH.

Also provided are stereoisomeric forms of Formula IIa, including enantiomers and diastereomers for which the phosphorus indicated in Formula IIa has R absolute stereochemistry.

In certain embodiments of the present invention, compounds have structural Formula II:

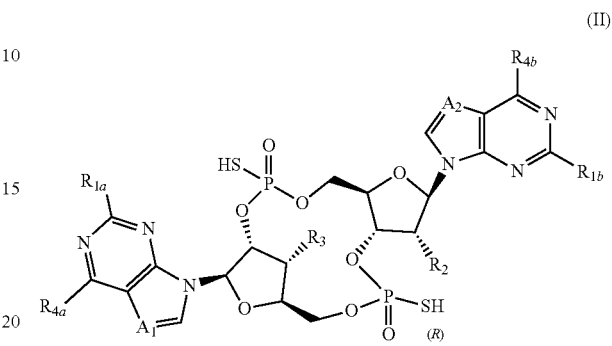

(II)

or a salt, ester, tautomer, or prodrug thereof, wherein:
$R_4$ and $A_2$ are independently selected from CH and N;
$R_{1a}$ and $R_{1b}$ are independently selected from H and $NH_2$;
$R_2$ is selected from OH, F, and Cl;
$R_3$ is OH;
$R_{4a}$ and $R_{4b}$ are independently selected from $NH_2$ and OH; and
when $A_1$ and $A_2$ are both N, then $R_2$ is not OH.

In certain embodiments of any of Formulas I, Ia, 2, and 2a, $A_1$ is CH and $A_2$ is N.
In certain embodiments of any of Formulas I, Ia, 2, and 2a, $A_1$ is N and $A_2$ is CH.
In certain embodiments of any of Formulas I, Ia, 2, and 2a, $A_1$ and $A_2$ are both CH.
In certain embodiments of any of Formulas I, Ia, 2, and 2a, $A_1$ and $A_2$ are both N.
In certain embodiments of any of Formulas I, Ia, 2, and 2a, $A_1$ and $A_2$ are both N, and $R_2$ is selected from F and Cl.
In certain embodiments of any of Formulas I, Ia, 2, and 2a, $R_{1a}$ and $R_{1b}$ are both H.
In certain embodiments of any of Formulas I, Ia, 2, and 2a, $R_{4a}$ and $R_{4b}$ are independently selected from $NH_2$ and $NHR_5$.
In certain embodiments of any of Formulas I, Ia, 2, and 2a, $R_{4a}$ and $R_{4b}$ are independently selected from $NH_2$ and $NHR_5$, and $R_{1a}$ and $R_{1b}$ are both H.
In certain embodiments of any of Formulas I, Ia, 2, and 2a, $R_{4a}$ and $R_{4b}$ are both $NH_2$.
In certain embodiments of any of Formulas I, Ia, 2, and 2a, $R_{4a}$ and $R_{4b}$ are both $NH_2$, and $R_{1a}$ and $R_{1b}$ are both H.

Also provided is a compound chosen from the species described herein, e.g.:

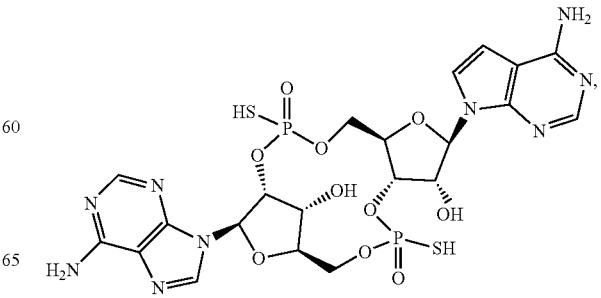

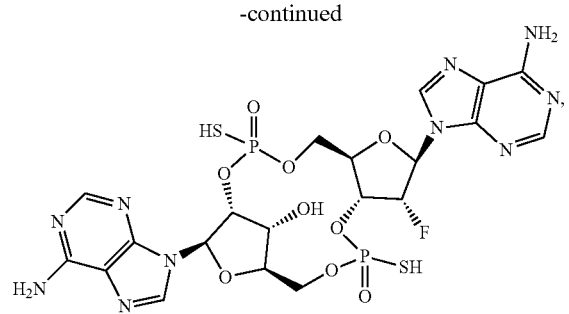
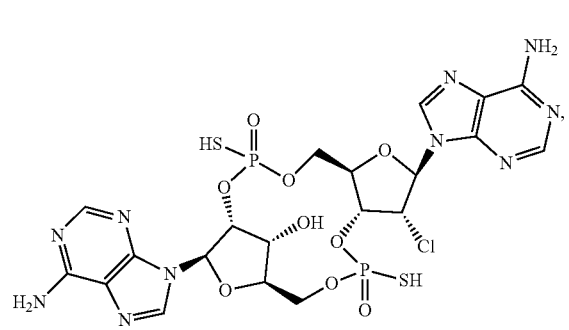
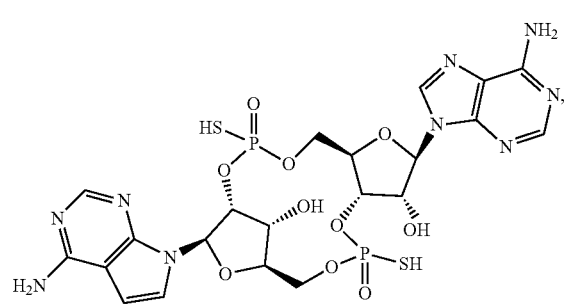
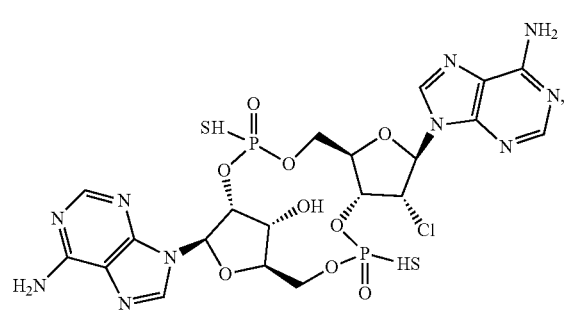
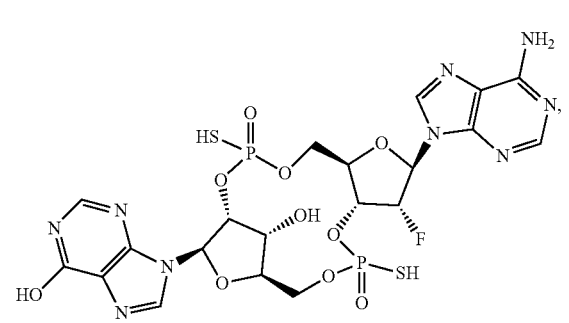
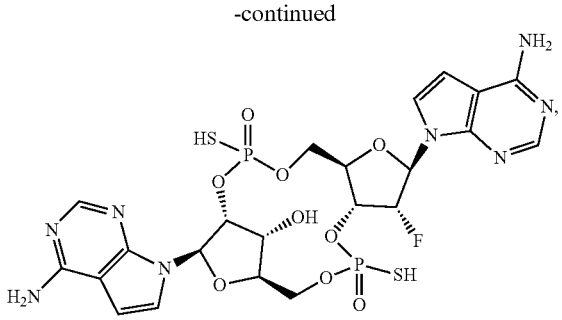
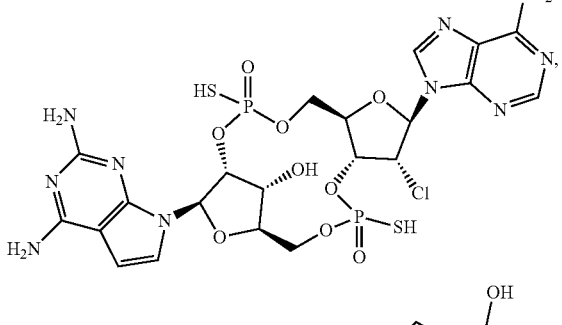
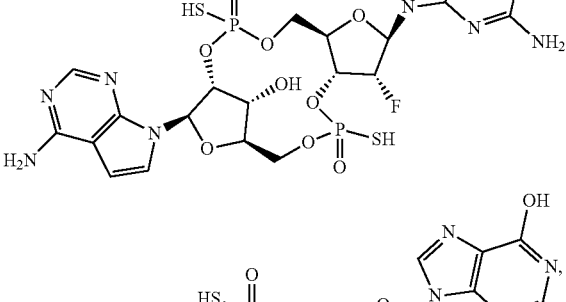
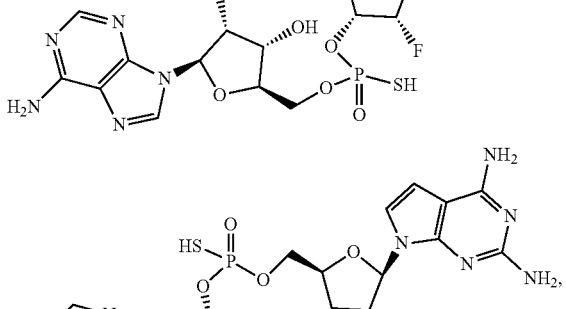
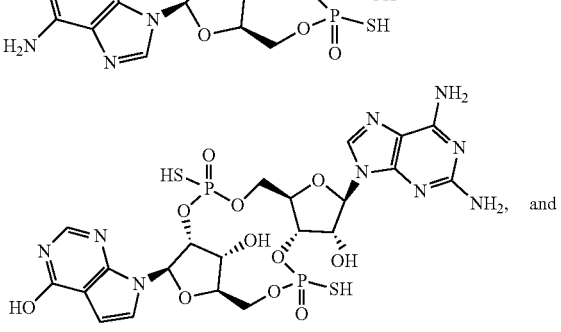

11
-continued
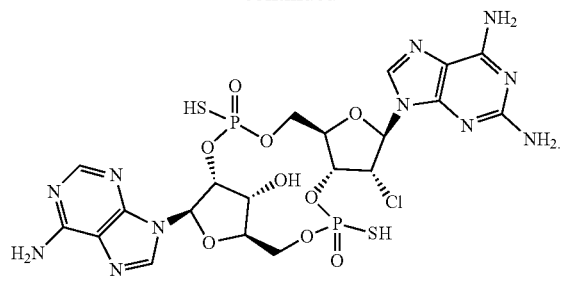
or a salt, ester, tautomer, or prodrug thereof.
In certain embodiments, the compound is selected from:
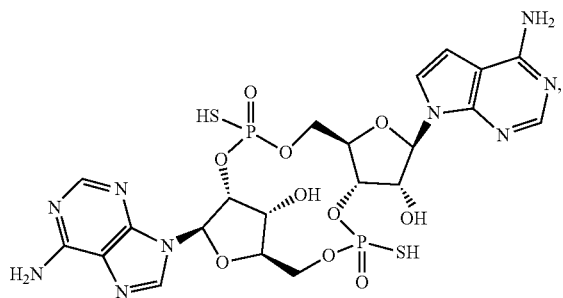
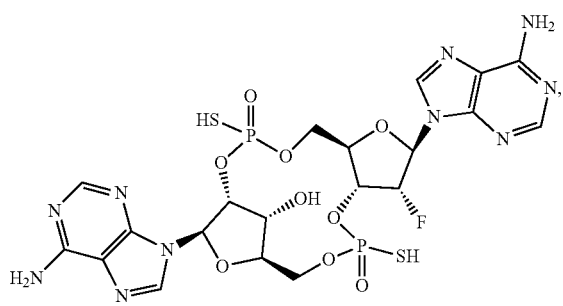
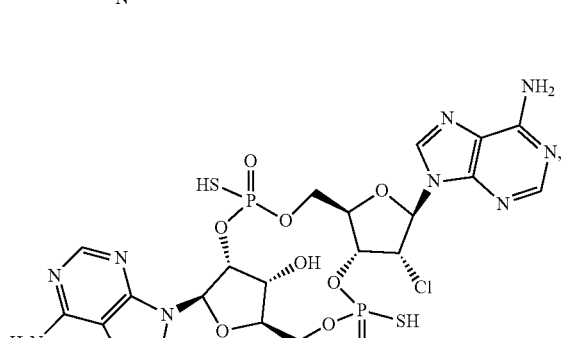
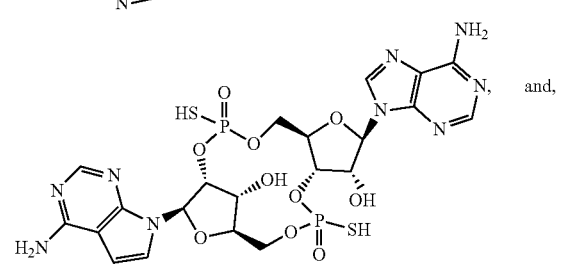
and,
12
-continued
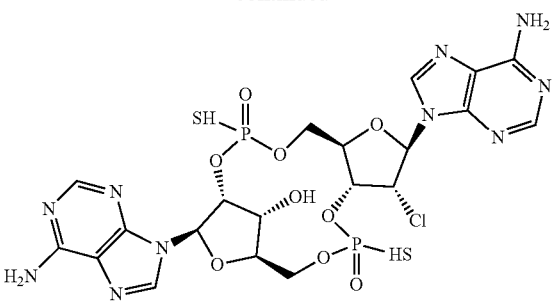
or a salt, ester, tautomer, or prodrug thereof.
In certain embodiments, the compound is selected from:
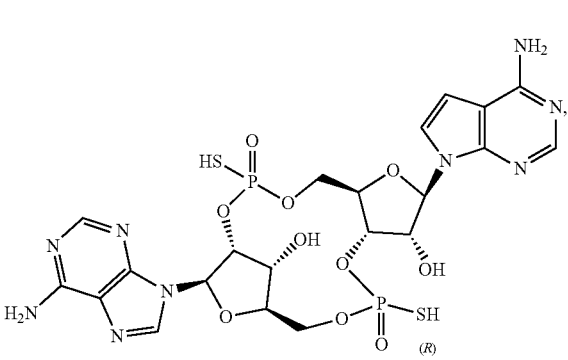
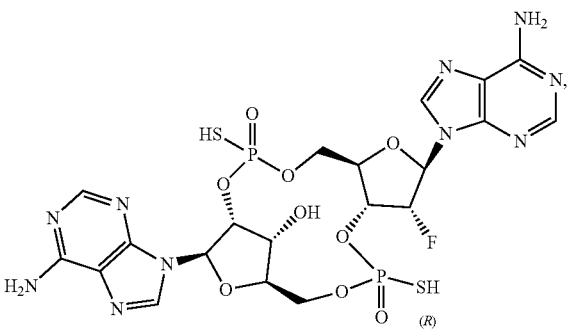
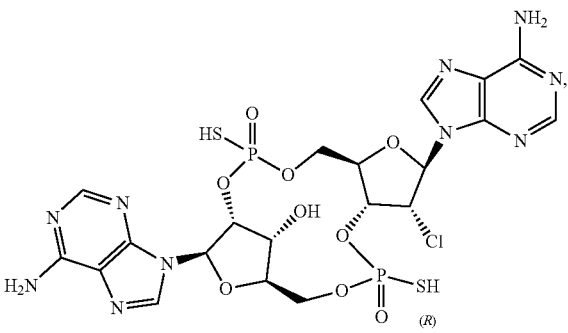
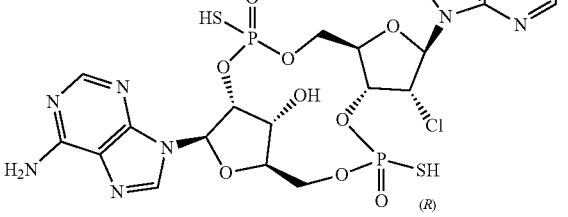

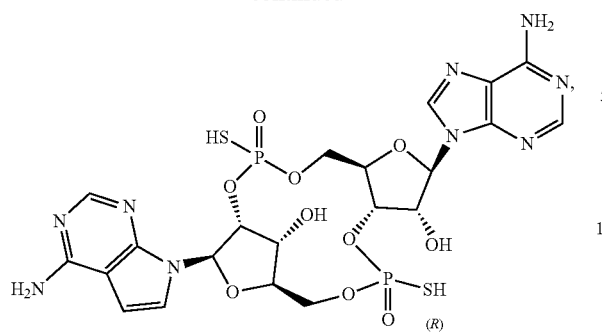
or a salt, ester, tautomer, or prodrug thereof.
In certain embodiments, the compound is selected from
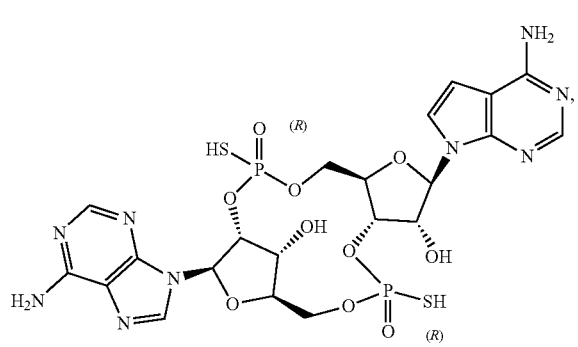
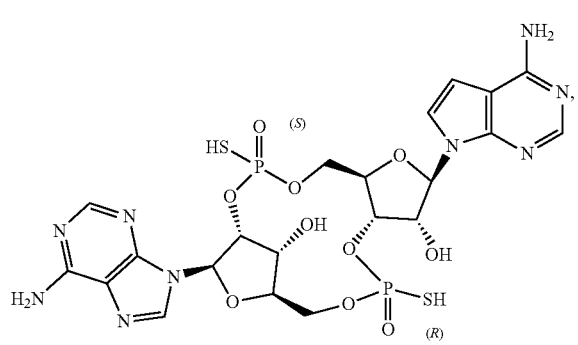
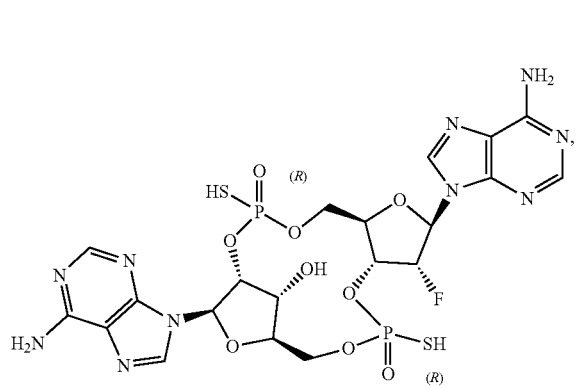
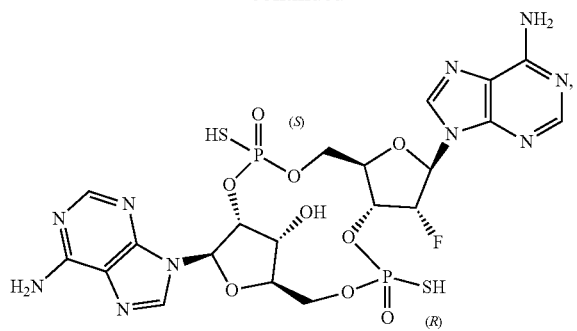
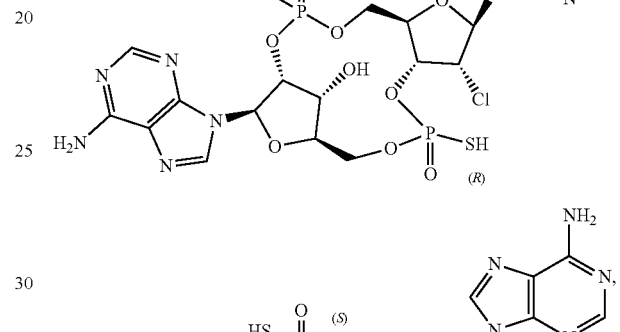
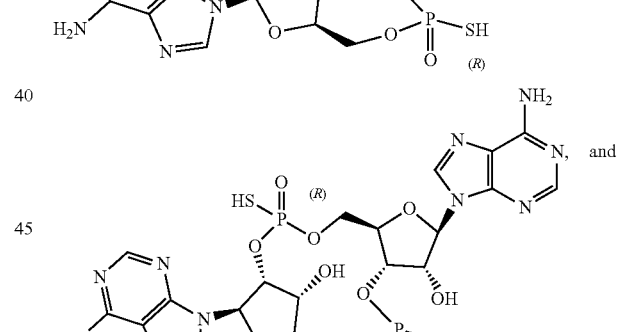
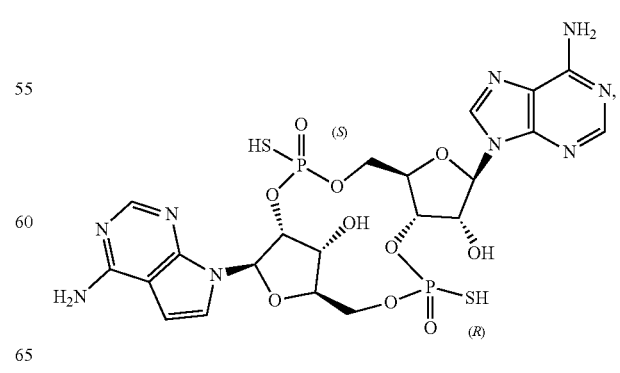
or a salt, ester, tautomer, or prodrug thereof.

In certain embodiments, the compound is selected from:
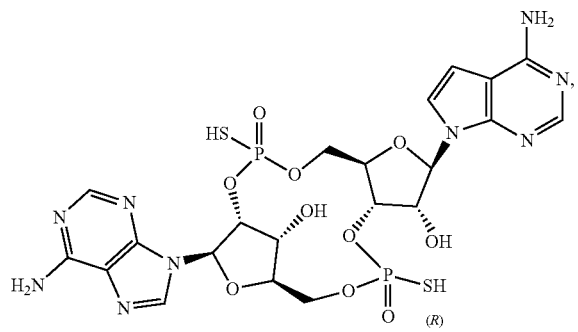
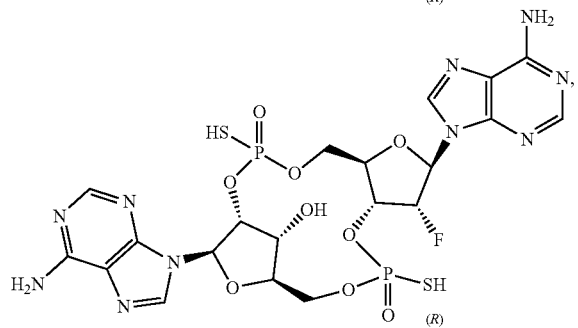
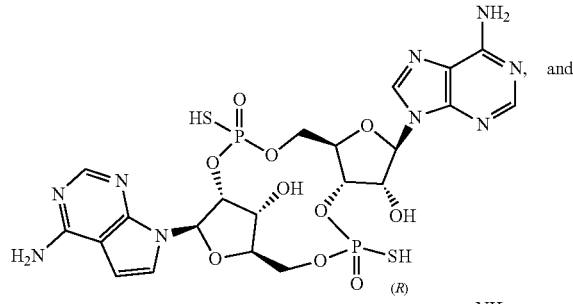
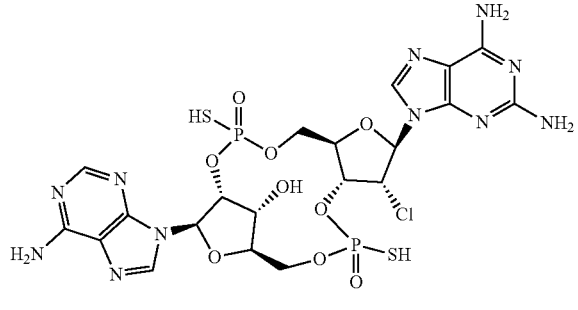
or a salt, ester, tautomer, or prodrug thereof.
In certain embodiments, the compound is selected from
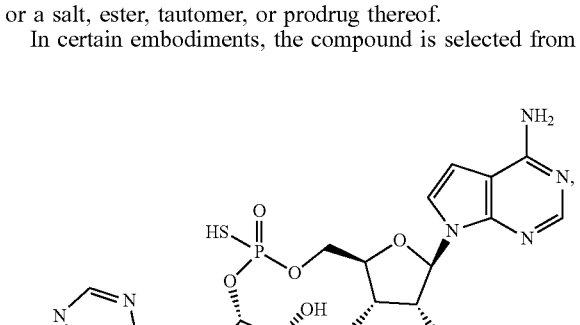
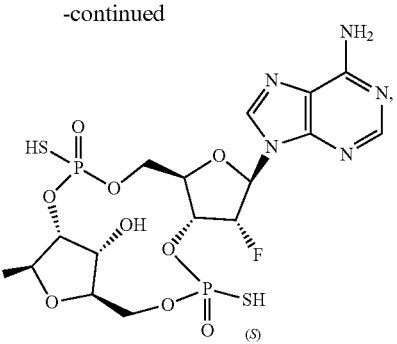
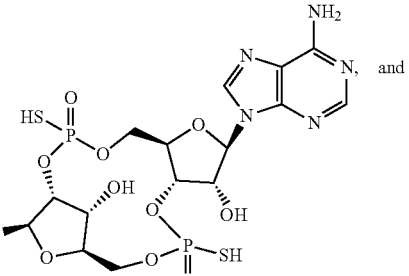
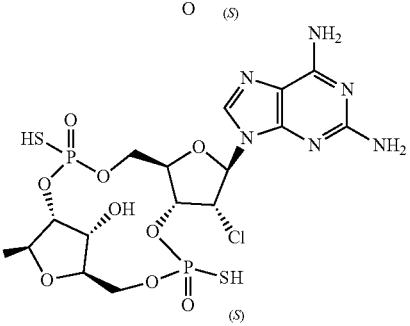
or a salt, ester, tautomer, or prodrug thereof.
In certain embodiments, the compound is selected from
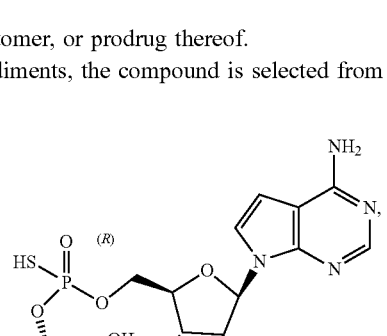
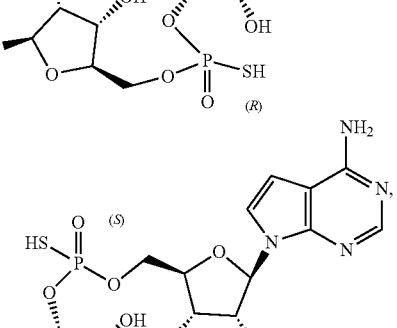

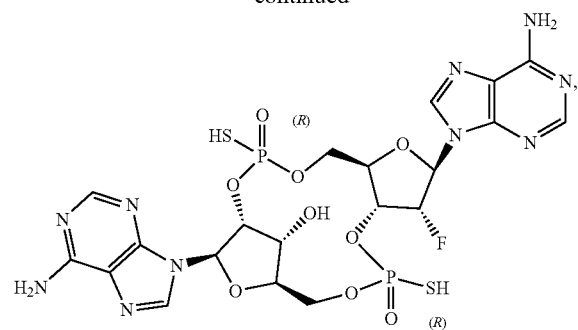
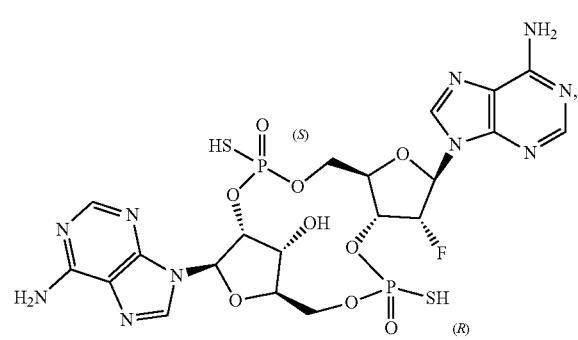
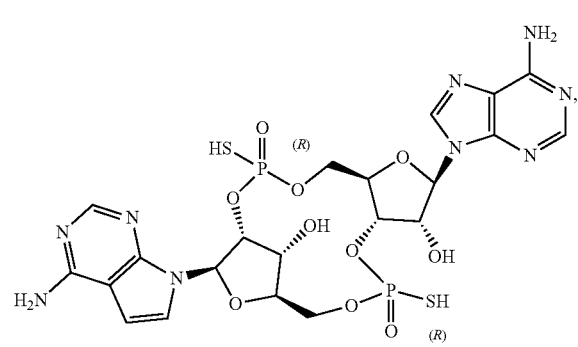
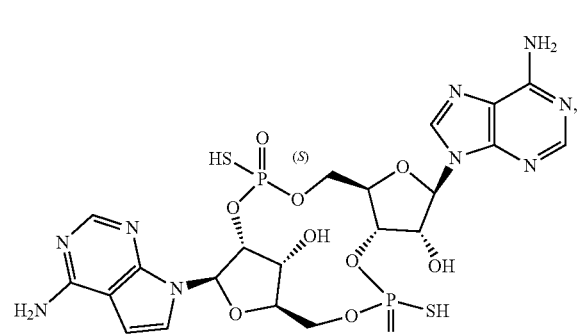
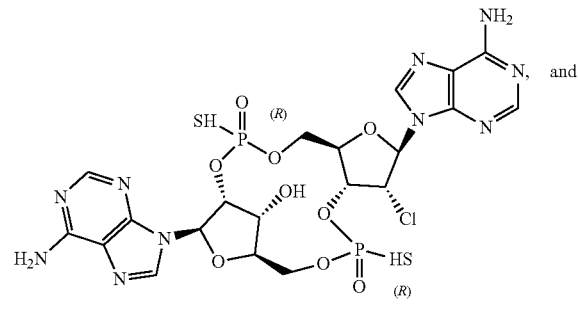
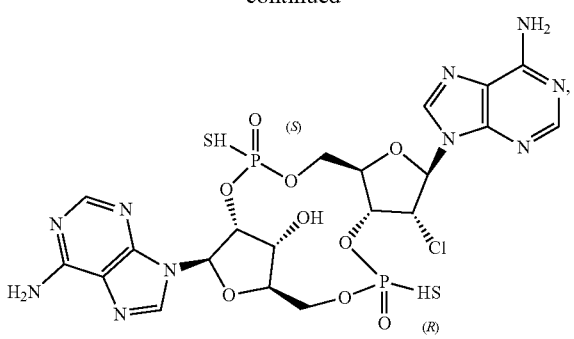
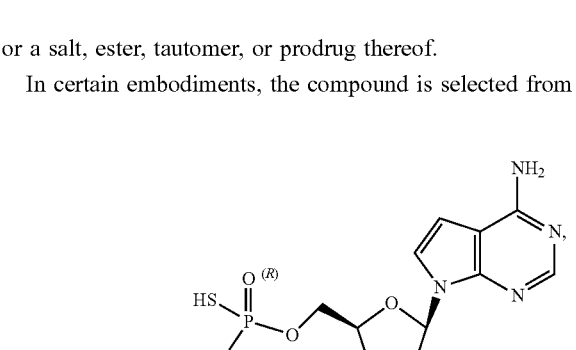
or a salt, ester, tautomer, or prodrug thereof.
In certain embodiments, the compound is selected from
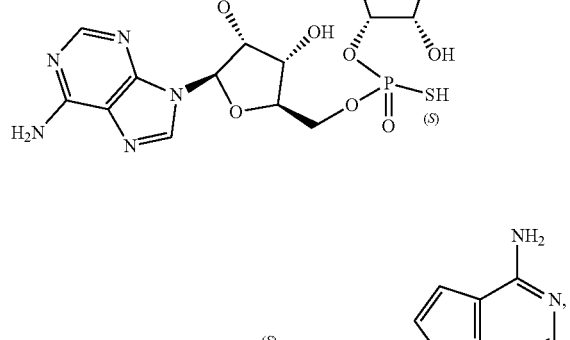
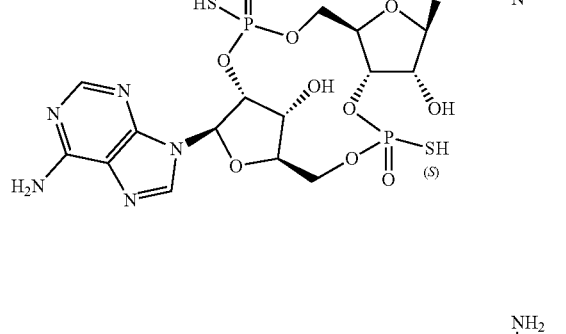
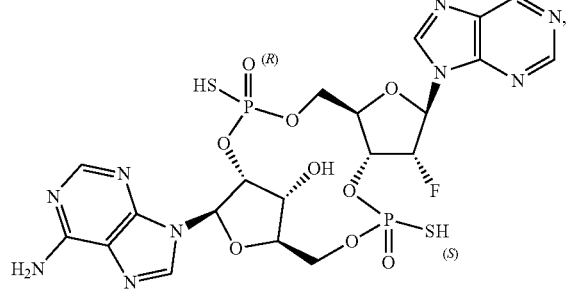

-continued

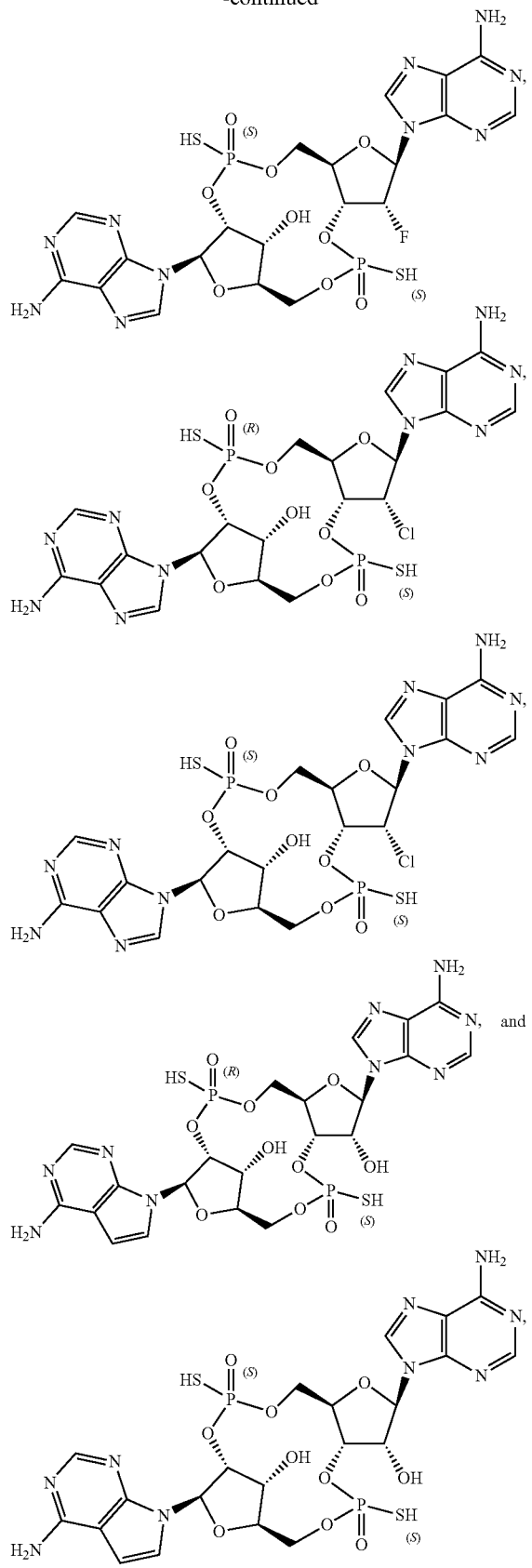

or a salt, ester, tautomer, or prodrug thereof.

Also provided is a compound chosen from the Examples disclosed herein, or a salt, ester, tautomer, or prodrug thereof.

Also provided are embodiments wherein a compound of Formula Ia is conjugated to a targeting moiety for targeted delivery.

In certain embodiments, the targeting moiety is a biotin or biotin analogue.

In certain embodiments, the targeting moiety is a peptide.
In certain embodiments, the targeting moiety is a protein.
In certain embodiments, the protein is transferrin.
In certain embodiments, the targeting moiety is an antibody.

Also provided are embodiments wherein a compound of Formula Ia is conjugated to an antibody for targeted delivery.

In certain embodiments, the antibody is a monoclonal antibody.

Also provided are embodiments wherein a compound of Formula Ia is conjugated to a hapten for binding to an antibody for targeted delivery.

Also provided are embodiments wherein a compound of Formula Ia is conjugated to a nanoparticle for targeted delivery.

In certain embodiments, the nanoparticle is comprised of polymers of one or more alpha-hydroxycarboxylic acids.

Also provided are embodiments wherein a compound of Formula Ia is contained within a polymeric delivery vehicle.

Also provided are embodiments wherein a compound of Formula Ia is contained within a liposome.

Also provided are embodiments wherein a compound of Formula Ia is contained within a micelle.

Also provided are embodiments wherein a compound of Formula Ia is contained within a vesicle.

In certain embodiments, the vesicle is comprised of phospholipids.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

The present invention also relates to a method of inhibiting at least one STING function comprising the step of contacting STING with a compound as described herein. The cell phenotype, cell proliferation, activity of STING, change in biochemical output produced by active STING, expression of STING, or binding of STING with a natural binding partner may be monitored. Such methods may be modes of treatment of disease, biological assays, cellular assays, biochemical assays, or the like.

Also provided herein is a method of treatment of a STING-mediated disease comprising the administration of a therapeutically effective amount of a compound as disclosed herein, or a salt thereof, to a patient in need thereof.

In certain embodiments, the STING-mediated disease is an autoimmune disease or disorder.

In certain embodiments, the STING-mediated disease is an immune deficiency or defect.

In certain embodiments, the STING-mediated disease is an inflammatory disease or disorder.

In certain embodiments, the STING-mediated disease is cancer.

In certain embodiments, the cancer is chosen from a metastatic solid tumor and lymphoma. Also provided herein is a compound as disclosed herein for use as a medicament.

Also provided herein is a compound as disclosed herein for use as a medicament for the treatment of a STING-mediated disease.

Also provided is the use of a compound as disclosed herein as a medicament.

Also provided is the use of a compound as disclosed herein as a medicament for the treatment of a STING-mediated disease.

Also provided is a compound as disclosed herein for use in the manufacture of a medicament for the treatment of a STING-mediated disease.

Also provided is the use of a compound as disclosed herein for the treatment of a STING-mediated disease.

Also provided herein is a method of agonizing STING comprising contacting STING with a compound as disclosed herein, or a salt thereof.

Also provided herein is a method for achieving an effect in a patient comprising the administration of a therapeutically effective amount of a compound as disclosed herein, or a salt thereof, to a patient, wherein the effect is chosen from induction of transcription of host defense genes, production of interferon beta, release of chemokines, priming of antigen-specific T-cells.

In certain embodiments, the STING-mediated disease is an autoimmune disease or disorder.

In certain embodiments, the STING-mediated disease is an immune deficiency or defect.

In certain embodiments, the STING-mediated disease is an inflammatory disease.

In certain embodiments, the STING-mediated disease is cancer.

In certain embodiments, the cancer is chosen from a metastatic solid tumor and lymphoma.

Also provided is a method of modulation of a STING-mediated function in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the oral pharmaceutical composition is chosen from a tablet and a capsule.

In certain embodiments, the pharmaceutical composition is formulated for parenteral administration. In certain embodiments, the parenteral administration is chosen from subcutaneous, intravenous, intramuscular, intraarterial, intraderminal, intrathecal, and epidural.

In certain embodiments, the pharmaceutical composition is formulated for intratumoral administration.

Terms

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH₃C(O)NH—).

The term "amino," as used herein, alone or in combination, refers to —NRR, wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C₆H₄=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1.1.1]pentane, camphor, adamantane, and bicyclo[3.2.1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently chosen from nitrogen, oxygen, and sulfur. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "mercapto" as used herein, alone or in combination, refers to an —SH group.

The term "phosphate", as used herein, alone or in combination, refers to the functional group P(=O)(OR$_X$)(OR$_Y$)(OR$_Z$), wherein R$_X$, R$_Y$, and R$_Z$ are independently chosen from hydrogen and organic groups. The term can also refer to a compound containing this functional group.

The term "phosphodiester", as used herein, alone in combination, refers to the functional group P(=X)(OR$_X$)(OR$_Y$)(OH), wherein R$_X$ and R$_Y$ are organic groups, and X is selected from oxygen and sulfur.

The term "thiophosphate", as used herein, alone or in combination, refers to a phosphate functional group in which one or more of the oxygen atoms has been replaced with sulfur. The term can also refer to a compound containing this functional group.

The term "thiolophosphate", as used herein, alone or in combination, refers to the phosphate functional group which contains a P—S—R moiety in place of a P—O—R moiety. This term can also refer to a compound containing this functional group.

The term "thionophosphate", as used herein, alone or in combination, refers to a phosphate functional group in which the P=O moiety has been replaced with a P=S moiety. The term can also refer to a compound containing this functional group.

It will be understood that, for certain thiolophosphates and thionophosphates, the following tautomeric equilibrium can occur:

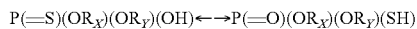

P(=S)(OR$_X$)(OR$_Y$)(OH)↔P(=O)(OR$_X$)(OR$_Y$)(SH)

The term "thiono" as used herein, alone or in combination, refers to =S.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "tautomer", as use herein, alone or in combination, refers to one of two or more isomers that rapidly interconvert. Generally, this interconversion is sufficiently fast so that an individual tautomer is not isolated in the absence of another tautomer. The ratio of the amount of tautomers can be dependent on solvent composition, ionic strength, and pH, as well as other solution parameters. The ratio of the amount of tautomers can be different in a particular solution and in the microenvironment of a biomolecular binding site in said solution. Examples of tautomers that are well known in the art include keto/enol, enamine/imine, and lactam/lactim tautomers. Examples of tautomers that are well known in the art also include 2-hydroxypyridine/2(1H)-pyridone and 2-aminopyridine/2(1H)-iminopyridone tautomers.

The term "predominantly one isomer", as used herein, means that a compound contains at least about 85% of one isomer (e.g., an enantiomer or diastereomer). For example, in certain embodiments, a compound may contain at least about 90% of one isomer. In certain embodiments, a compound may contain at least about 95% of one isomer. In certain embodiments, a compound may contain at least about 98% of one isomer. In certain embodiments, a compound may contain at least about 99% of one isomer. Similarly, the phrase "substantially free from other isomers" means that the compound contains at most about 15% of another isomer. For example, in certain embodiments, the compound contains at most about 10% of another isomer. In certain embodiments, the compound contains at most about 5% of another isomer. In certain embodiments, the compound contains at most about 2% of another isomer. In certain embodiments, the compound contains at most about 1% of another isomer.

Cyclic dinucleotides, including those specifically described herein, as well as isoforms (e.g., tautomers) of those specifically described herein that can be used in practicing the invention. Cyclic dinucleotides can be obtained using any suitable method. For example, cyclic dinucleotides may be made by chemical synthesis using nucleoside derivatives as starting material. Cyclic dinucleotides can also be produced by in vitro synthesis, using recombinant purified cGAMP synthase. Moreover, the structures of such cyclic dinucleotides can be confirmed using analytical chemical techniques. These techniques include, but are not limited to, nuclear magnetic resonance (proton and other nuclei, and both 1D and 2D), X-ray crystallography, electromagnetic spectroscopy (including but not limited to visible, infrared, optical regions of the electromagnetic spectrum, and including but not limited to absorption, emission, and optical rotation methods) and mass spectrometry.

Cyclic dinucleotides provided herein can be described by the following nomenclature: cyclic[X$_1$(A-5')pX$_2$(B-5')p], wherein X$_1$ and X$_2$ are the first and second nucleosides, A is the point of attachment of the first nucleoside (e.g. 2' or 3') that is linked to the 5' carbon of the second nucleoside via a phosphodiester bond, and B is the point of attachment of the second nucleoside (e.g. 2' or 3') that is linked to the 5' carbon of the first nucleoside. For instance, based on this nomenclature, cyclic(A(2'-5')pG(3'-5')p] has the following formula:

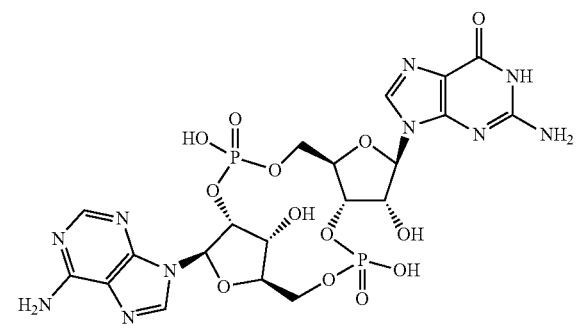 [SMILES: Nc1nc2c(ncn2[C@@H]2O[C@@H]3COP(=O)(O)O[C@@H]4[C@H](O)[C@@H](COP(=O)(O)O[C@H]3[C@H]2O)O[C@H]4n2cnc3c(N)ncnc32)c(=O)[nH]1]

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "sulfhydryl," as used herein, alone or in combination, refers to an —SH group.

The term "thiono", as used herein, alone or in combination, refers to a sulfur doubly bonded to the parent atom.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3CS(O)_2NR$— group with X is a halogen and R as defined herein.

The term "trihalomethanesulfonyl" refers to a $X_3CS(O)_2$— group where X is a halogen.

The term "trihalomethoxy" refers to a $X_3CO$— group where X is a halogen.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N (R)— may be attached to the parent moiety at either the carbon or the nitrogen.

Asymmetric centers exist in the compounds disclosed herein. These centers are designated by the symbols "R" or "S," depending on the configuration of substituents around the chiral atom. It will be understood by a person in the art that any tetrahedral atom with for nonidentical substituents can possess a chiral center. The group of such atoms includes, but is not limited to, carbon and phosphorus. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The terms "R" and "S" will be understood by persons of skill in the chemical art to refer to the absolute stereochemistry at a given asymmetric tetrahedral atom, using the Cahn-Ingold-Prelog rules for priority. A chemical structure provided herein having an asymmetric tetrahedral atom will embrace compounds having either "R" or "S" absolute stereochemistry at said atom, in the absence of either (a) a clear "R" or "S" designation in the structure at said atom, or (b) clear wedge and dash depictions of bonds to said atom, as understood by persons of skill in the chemical art to indicate absolute stereochemistry.

The terms "$R_P$" and "$S_P$" refer to absolute stereochemistry at a phosphorus atom. For compounds with more than one phosphorus atom, and thus requiring more than one such term, the terms will be listed in the same order as is given for the phosphorus atoms in the name provided.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

As used herein, alone or in combination, the term "supramolecular assembly" refers to an assembly of molecules held together by noncovalent interactions. In some embodiments, the nocovalent interaction is a hydrophobic interaction. In some embodiments, the noncovalent interaction is a hydrogen bonding interaction. In some embodiments, the noncovalent interaction is electrostatic interaction between ions. In some embodiments, the molecules are amphiphilic in nature. In some embodiments, the supramolecular assemblies comprise both hydrophilic and hydrophobic regions. In some embodiments, the supramolecular assemblies comprise lipid bilayers.

As used herein, alone or in combination, the term "nanoparticle" refers to a particle larger than conventional synthetic organic molecules. In some embodiments, nanoparticles are greater than about 100 picometers in diameter. In some embodiments, nanoparticles are greater than about 1 nanometer in diameter. In some embodiments, nanoparticles are greater than about 10 nanometers in diameter. In some embodiments, nanoparticles are greater than about 100 nanometers in diameter. In some embodiments, nanoparticles are greater than about 1 micrometer in diameter. In some embodiments, nanoparticles are greater than about 10 micrometers in diameter. In some embodiments, nanoparticles are composed primarily of metal, including but not limited to gold, lead, and zinc. In some embodiments, nanoparticles are composed of inorganic salts, including but limited to cadmium selenide, zinc telluride, and silicon nitride. In some embodiments, nanoparticles are uniform in composition. In some embodiments, nanoparticles comprise both core and shell regions of differing composition.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

A typical test to determine whether a compound is a STING agonist is to present the compound to a wild-type human or animal cell line and in the corresponding cell line in which the STING coding gene has been genetically inactivated (e.g. a homozygous STING knockout cell line). A STING agonist will induce Type I interferons in the wild-type cells but will not induce Type I interferons in the cells in which the STING coding gene has been inactivated.

As used herein, the term "STING agonist" is used to refer to a compound that induces activation of STING-dependent pathways at least as effectively as bis-3',5' c-di-GMP. In some embodiments, the STING agonist induces activation of STING-dependent pathways at least 2-fold as effectively as bis-3',5' c-di-GMP. In some embodiments, the STING agonist induces activation of STING-dependent pathways at least 5-fold as effectively as bis-3',5' c-di-GMP. In some embodiments, the STING agonist induces activation of STING-dependent pathways at least 10-fold as effectively as bis-3',5' c-di-GMP. In some embodiments, the STING agonist induces activation of STING-dependent pathways at least 20-fold as effectively as bis-3',5' c-di-GMP. In some embodiments, the STING agonist induces activation of STING-dependent pathways at least 50-fold as effectively as bis-3',5' c-di-GMP. In some embodiments, the STING agonist induces activation of STING-dependent pathways at least 100-fold as effectively as bis-3',5' c-di-GMP.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, "treating," "treatment," and the like means ameliorating a disease, so as to reduce, ameliorate, or eliminate its cause, its progression, its severity, or one or more of its symptoms, or otherwise beneficially alter the disease in a subject. Reference to "treating," or "treatment" of a patient is intended to include prophylaxis. Treatment may also be preemptive in nature, i.e., it may include prevention of disease in a subject exposed to or at risk for the disease. Prevention of a disease may involve complete protection from disease, for example as in the case of prevention of infection with a pathogen, or may involve prevention of disease progression, for example from prediabetes to diabetes. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can be administered with the use of a drug delivery vehicle.

As used herein, alone or in combination, the term "drug delivery vehicle" refers to a molecular assembly that comprises a pharmaceutically active compound and a second component that confers pharmacokinetic benefits.

In some embodiments, the drug delivery vehicle comprises a pharmaceutically active compound and a targeting moiety.

As used herein, alone or in combination, the term "targeting moiety" is used to describe a moiety that assists in the delivery of the pharmaceutically active compound to a biochemical target. In some embodiments, the pharmaceutically active compound is covalently linked to the targeting moiety. In some embodiments, the pharmaceutically active compound is covalently linked to the targeting moiety with a chemically labile bond. Non-limiting examples of chemically labile bonds used for this purpose include acetals, ketals, esters, and amides. In some embodiments, the pharmaceutically active compound is noncovalently associated with the targeting moiety.

In some embodiments, the targeting moiety is a biomolecule. Biomolecules that can be used as a targeting moiety include, but is not limited to, peptides, proteins, antibodies, nucleic acids, and naturally occurring hormones, cofactors, signalling molecules, and enzyme substrates. In some embodiments, the targeting moiety is a synthetic analogue of a biomolecule. In some embodiments, the targeting moiety is a synthetic molecule. In some embodiments, the targeting moiety is a nanoparticle.

In some embodiments, the drug delivery vehicle comprises a pharmaceutically active compound and a container moiety.

As used herein, alone or in combination, the term "container moiety" refers to a molecule or supramolecular structure that partially or completely encloses a pharmaceutically active compound.

In some embodiments, the container moiety is a single molecule. In some embodiments, the container moiety is a nanoparticle.

In some embodiments, the container moiety is a supramolecular assembly of noncovalently associated molecules. In some embodiments, the container moiety is a liposome. In some embodiments, the container moiety is a micelle. In some embodiments, the container moiety is a vesicle. In some embodiments, the container moiety comprises phospholipids.

In some embodiments, the pharmaceutically active compound is fully contained within the container moiety. In some embodiments, the pharmaceutically active compound is partially contained within the container moiety. In some embodiments, the pharmaceutically active compound is noncovalently associated with the container moiety.

In some embodiments, the drug delivery vehicle comprises a selectivity moiety.

As used herein, alone or in combination, the term "selectivity moiety" refers to a molecule that confers selective delivery to a certain region of the body of a subject. In some embodiments, the selectivity moiety selectively delivers the drug delivery vehicle to an organ of interest. In some embodiments, the selectivity moiety selectively delivers the drug delivery vehicle to a tumor. In some embodiments, the selectivity moiety improves transport across biological membranes. In some embodiments, the selectivity moiety improves transport from the gastrointestinal tract into the bloodstream. In some embodiments, the selectivity moiety improves transport across the blood-brain barrier. A selectivity moiety may also be a targeting moiety, and vice versa.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, tautomer, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In certain embodiments, parenteral administration is facilitated with liposomes. Liposomes are vesicles formed from one or more layers of phospholipid. Liposomes comprise both hydrophilic and hydrophobic regions, and can be used to improve the pharmacokinetic properties of a formulation. In some embodiments, the liposomes can comprise one or more additional components, such as peptidoglycan, lipopeptide, lipopolysaccharide, phosphorylated lipid A, acylated phosphatidylcholine, acylated glycerol, oligonucleotides, ceramides, retinoic acid, quaternary ammonium salts, anionic, cationic, and nonionic surfactants, lipoteichoic acid, resiquimod, imiquimod, and flagellin.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhaler or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, tautomer, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating STING-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of STING-mediated disorders.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Autoimmune Disorders

In some embodiments, the compounds and pharmaceutical compositions of the present disclosure may be useful in the treatment of autoimmune diseases and disorders. In some embodiments, the autoimmune disorder is selected from systemic lupus erythmatosis, psoriasis, insulin-dependent diabetes, dermatomyositis, and Sjogren's syndrome. In some embodiments, the autoimmune disorder is multiple sclerosis.

In some embodiments, the compounds and pharmaceutical compositions of the present disclosure may be useful in the treatment of immune system deficiencies or defects.

In some embodiments, the compounds and pharmaceutical compositions of the present disclosure may be useful in the treatment of microbial or viral infections. In some embodiments, the viral infection is hepatitis.

Inflammation and Inflammatory Disease

In some embodiments, the compounds and pharmaceutical compositions of the present disclosure may be useful in the treatment of inflammation or an inflammatory disease or disorder. In some embodiments, the inflammatory disease or disorder is selected from musculoskeletal inflammation, vascular inflammation, neural inflammation, digestive system inflammation, inflammation of the reproductive system, and ocular inflammation.

In some embodiments, the inflammatory disease or disorder is selected from arthritis, tendonitis, synovitis, tenosynovitis, bursitis, fibrositis (fibromyalgia), epicondylitis, myositis, osteitis, blepharitis, blepharochalasis, conjunctivitis, dacryoadenitis, keratitis, keratoconjunctivitis sicca (dry eye), scleritis, trichiasis, uveitis, encephalitis, Guillain-Barre syndrome, meningitis, neuromyotonia, narcolepsy, multiple sclerosis, myelitis, schizophrenia, arthrosclerosis, arthritis, phlebitis, vasculitis, lymphangitis, cholangitis, cholecystitis, enteritis, enterocolitis, gastritis, gastroenteritis, inflammatory bowel disease (such as Crohn's disease and ulcerative colitis), ileitis, proctitis, cervicitis, chorioamnionitis, endometritis, epididymitis, omphalitis, oophoritis, orchitis, salpingitis, tubo-ovarian abscess, urethritis, vaginitis, vulvitis, and vulvodynia.

In some embodiments, the inflammatory disease or disorder is selected from appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatitis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xengrafts, sewrum sickness, and graft vs host disease), acute pancreatitis, chronic pancreatitis, acute respiratory distress syndrome, Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, astopic dermatitis, drug hypersensistivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autroimmine) hemolytic anemia, leukemia and lymphomas in adults, acute leukemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosis, psoriasis, chronic pulmonary disease, and inflammation accompanying infectious conditions (e.g., sepsis).

In some embodiments, the compounds and pharmaceutical compositions of the present disclosure may be useful for the treatment of autoimmune disease or disorder having an inflammatory component. In some embodiments, the autoimmune disease or disorder is selected from acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome, Grave's disease, Guillain-Barre syndrome, Hashimoto's disease, Henoch-Schonlein purpura, Kawasaki's disease, lupus erythematosus, microscopic colitis, microscopic polyarteritis, mixed connective tissue disease, multiple sclerosis, myasthenia gravis, opsoclonus myoclonus syndrome, optic neuritis, ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune hemolytic anemia, interstitial cystitis, lyme disease, morphea, psoriasis, sarcoidosis, scleroderma, ulcerative colitis, and vitiligo.

In some embodiments, the compounds and pharmaceutical compositions of the present disclosure may be useful for the treatment of a neurodegenerative disease or disorder. In some embodiments, the neurodegenerative disease or disorder is chosen from Parkinson's disease, Alzheimer's disease, Huntington's disease, and amyotrophic lateral sclerosis.

In some embodiments, the compounds and pharmaceutical compositions of the present disclosure may be administered before, during, or after administration of a vaccine. The benefits afforded by the coadministration may include: enhanced efficacy of the vaccine, reduced toxicity of the vaccine, or reduced side effects of the vaccine. In some embodiments, the vaccine can comprise inactivated or attenuated bacteria or viruses. In some embodiments, the vaccine can comprise purified antigens. In some embodiments, the vaccine can comprise live viral or bacterial delivery vectors that have been recombinantly engineered to express or secrete an antigen. In some embodiments, the vaccine can comprise antigen presenting cells that are loaded with antigen. In some embodiments, the vaccine may comprise an inactivated tumor cell.

Cancer

In some embodiments, the compounds and pharmaceutical compositions of the present disclosure may be useful in the treatment or prevention of cancer.

In some embodiments, the compounds of the present disclosure may be used to prevent or treat cancer, wherein the cancer is one or a variant of Acute Lymphoblastic Leukemia (ALL), Acute Myeloid Leukemia (AML), Adrenocortical Carcinoma, AIDS-Related Cancers (Kaposi Sarcoma and Lymphoma), Anal Cancer, Appendix Cancer, Atypical Teratoid/Rhabdoid Tumor, Basal Cell Carcinoma, Bile Duct Cancer (including Extrahepatic), Bladder Cancer, Bone Cancer (including Osteosarcoma and Malignant Fibrous Histiocytoma), Brain Tumor (such as Astrocytomas, Brain and Spinal Cord Tumors, Brain Stem Glioma, Central Nervous System Atypical Teratoid/Rhabdoid Tumor, Central Nervous System Embryonal Tumors, Craniopharyngioma, Ependymoblastoma, Ependymoma, Medulloblastoma, Medulloepithelioma, Pineal Parenchymal Tumors of Intermediate Differentiation, Supratentorial Primitive Neuroectodermal Tumors and Pineoblastoma), Breast Cancer, Bronchial Tumors, Burkitt Lymphoma, Basal Cell Carcinoma, Bile Duct Cancer (including Extrahepatic), Bladder Cancer, Bone Cancer (including Osteosarcoma and Malignant Fibrous Histiocytoma), Carcinoid Tumor, Carcinoma of Unknown Primary, Central Nervous System (such as Atypical Teratoid/Rhabdoid Tumor, Embryonal Tumors and Lymphoma), Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma (Mycosis Fungoides and Sezary Syndrome), Duct, Bile (Extrahepatic), Ductal Carcinoma In Situ (DCIS), Embryonal Tumors (Central Nervous System), Endometrial Cancer, Ependymoblastoma, Ependymoma, Esophageal Cancer, Esthesioneuroblastoma, Ewing Sarcoma Family of Tumors, Extracranial Germ Cell Tumor, Extragonadal Germ Cell Tumor, Extrahepatic Bile Duct Cancer, Eye Cancer (like Intraocular Melanoma, Retinoblastoma), Fibrous Histiocytoma of Bone (including Malignant and Osteosarcoma) Gallbladder Cancer, Gastric (Stomach) Cancer, Gastrointestinal Carcinoid Tumor, Gastrointestinal Stromal Tumors (GIST), Germ Cell Tumor (Extracranial, Extragonadal, Ovarian), Gestational Trophoblastic Tumor, Glioma, Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors (Endocrine, Pancreas), Kaposi Sarcoma, Kidney (including Renal Cell), Langerhans Cell Histiocytosis, Laryngeal Cancer, Leukemia (including Acute Lymphoblastic (ALL), Acute Myeloid (AML), Chronic Lymphocytic (CLL), Chronic Myelogenous (CML), Hairy Cell), Lip and Oral Cavity Cancer, Liver Cancer (Primary), Lobular Carcinoma In Situ (LCIS), Lung Cancer (Non-Small Cell and Small Cell), Lymphoma (AIDS-Related, Burkitt, Cutaneous T-Cell (Mycosis Fungoides and Sezary Syndrome), Hodgkin, Non-Hodgkin, Primary Central Nervous System (CNS), Macroglobulinemia, Waldenström, Male Breast Cancer, Malignant Fibrous Histiocytoma of Bone and Osteosarcoma, Medulloblastoma, Medulloepithelioma, Melanoma (including Intraocular (Eye)), Merkel Cell Carcinoma, Mesothelioma (Malignant), Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML), Myeloma and Multiple Myeloma, Myeloproliferative Disorders (Chronic), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and, Oropharyngeal Cancer, Osteosarcoma and Malignant Fibrous Histiocytoma of Bone, Ovarian Cancer (such as Epithelial, Germ Cell Tumor, and Low Malignant Potential Tumor), Pancreatic Cancer (including Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pineal Parenchymal Tumors of Intermediate Differentiation, Pineoblastoma and Supratentorial Primitive Neuroectodermal Tumors, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (like Ewing Sarcoma Family of Tumors, Kaposi, Soft Tissue, Uterine), Sezary Syndrome, Skin Cancer (such as Melanoma, Merkel Cell Carcinoma, Nonmelanoma), Small Cell Lung Cancer, Small Intestine Cancer, Soft Tissue Sarcoma, Squamous Cell Carcinoma, Squamous Neck Cancer with Occult Primary, Metastatic, Stomach (Gastric) Cancer, Supratentorial Primitive Neuroectodermal Tumors, T-Cell Lymphoma (Cutaneous, Mycosis Fungoides and Sezary Syndrome), Testicular Cancer, Throat Cancer, Thymoma and Thymic Carcinoma, Thyroid Cancer, Transitional Cell Cancer of the Renal Pelvis and Ureter, Trophoblastic Tumor (Gestational), Unknown Primary, Unusual Cancers of Childhood, Ureter and Renal Pelvis, Transitional Cell Cancer, Urethral Cancer, Uterine Cancer, Endometrial, Uterine Sarcoma, Waldenström Macroglobulinemia or Wilms Tumor.

In some embodiments, methods described herein are used to treat a disease condition comprising administering to a subject in need thereof a therapeutically effective amount of a compound of Formula I or pharmaceutically acceptable salt thereof, wherein the condition is cancer which has developed resistance to chemotherapeutic drugs and/or ionizing radiation.

Adjuvants for Vaccines

In some embodiments of the present invention, there is provided a compound of formula (Ia), or a pharmaceutically acceptable salt thereof for use as vaccine adjuvants.

In some embodiments there is further provided a vaccine adjuvant comprising a compound of formula (Ia), or a pharmaceutically acceptable salt thereof.

In some embodiments there is further provided an immunogenic composition comprising an antigen or antigen composition and a compound of formula (Ia), or a pharmaceutically acceptable salt thereof.

In some embodiments there is further provided an immunogenic composition comprising an antigen or antigen composition and a compound of formula (Ia), or a pharmaceutically acceptable salt thereof for use in the treatment or prevention of disease.

In some embodiments there is further provided the use of a compound of formula (Ia), or a pharmaceutically acceptable salt thereof, for the manufacture of an immunogenic composition comprising an antigen or antigen composition, for the treatment or prevention of disease. In some embodiments there is further provided a method of treating or preventing disease comprising the administration to a human subject suffering from or susceptible to disease, an immunogenic composition comprising an antigen or antigen composition and a compound of formula (Ia), or a pharmaceutically acceptable salt thereof.

In some embodiments there is further provided a vaccine composition comprising an antigen or antigen composition and a compound of formula (Ia), or a pharmaceutically acceptable salt thereof for use in the treatment or prevention of disease. In some embodiments there is further provided a vaccine composition comprising an antigen or antigen composition and a compound of formula (Ia), or a pharmaceutically acceptable salt thereof for use in the treatment or prevention of disease In some embodiments there is further provided the use of a compound of formula (I), or a pharmaceutically acceptable salt thereof, for the manufacture of a vaccine composition comprising an antigen or antigen composition, for the treatment or prevention of disease.

In some embodiments there is further provided a method of treating or preventing disease comprising the administration to a human subject suffering from or susceptible to disease, a vaccine composition comprising an antigen or antigen composition and a compound of formula (I), or a pharmaceutically acceptable salt thereof.

The compounds of formula (Ia) and pharmaceutically acceptable salts thereof may also be formulated with vaccines as adjuvants to modulate their activity. Such compositions may contain one or more antibodies, or one or more antibody fragments or an antigenic component including but not limited to protein, DNA, live or dead bacteria and/or viruses or virus-like particles. Such compositions may also contain one or more components with adjuvant activity including but not limited to aluminium salts, oil and water emulsions, heat shock proteins, lipid A preparations and derivatives, glycolipids, other TLR agonists such as CpG DNA or similar agents, cytokines such as GM-CSF or IL-12 or similar agents.

Combinations and Combination Therapy

The compounds of the present invention can be used, alone or in combination with other pharmaceutically active compounds, to treat conditions such as those previously described hereinabove. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention and one or more additional pharmaceutically active compounds.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is selected from anti-cancer drugs, anti-proliferative drugs, and anti-inflammatory drugs.

STING agonist compositions described herein are also optionally used in combination with other therapeutic reagents that are selected for their therapeutic value for the condition to be treated. In general, the compounds described herein and, in embodiments where combination therapy is employed, other agents do not have to be administered in the same pharmaceutical composition and, because of different physical and chemical characteristics, are optionally administered by different routes. The initial administration is generally made according to established protocols and then, based upon the observed effects, the dosage, modes of administration and times of administration subsequently modified. In certain instances, it is appropriate to administer a STING agonist compound, as described herein, in combination with another therapeutic agent. By way of example only, the therapeutic effectiveness of a STING agonist is enhanced by administration of another therapeutic agent (which also includes a therapeutic regimen) that also has therapeutic benefit. Regardless of the disease, disorder or condition being treated, the overall benefit experienced by the patient is either simply additive of the two therapeutic agents or the patient experiences an enhanced (i.e., synergistic) benefit. Alternatively, if a compound disclosed herein has a side effect, it may be appropriate to administer an agent to reduce the side effect; or the therapeutic effectiveness of a compound described herein may be enhanced by administration of an adjuvant.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a STING agonist as described herein) may be administered in any order, or simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses. If not simultaneous, the timing between the multiple doses optionally varies from more than zero weeks to less than twelve weeks.

In addition, the combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time between the multiple administration steps ranges from a few minutes to several hours, depending upon the properties of each pharmaceutical agent, such as potency, solubility, bioavailability, plasma half-life and kinetic profile of the pharmaceutical agent.

In another embodiment, a STING agonist is optionally used in combination with procedures that provide additional benefit to the patient. A STING agonist and any additional therapies are optionally administered before, during or after the occurrence of a disease or condition, and the timing of administering the composition containing a STING agonist varies in some embodiments. Thus, for example, a STING agonist is used as a prophylactic and is administered continuously to subjects with a propensity to develop conditions or diseases in order to prevent the occurrence of the disease or condition. A STING agonist and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention.

It should be understood that in some embodiments of the invention various alternatives to the embodiments described herein are employed in practicing the invention.

A STING agonist can be used in combination with anti-cancer drugs, including but not limited to the following classes: alkylating agents, anti-metabolites, plant alkaloids and terpenoids, topoisomerase inhibitors, cytotoxic antibiotics, angiogenesis inhibitors and tyrosine kinase inhibitors.

For use in cancer and neoplastic diseases a STING agonist may be optimally used together with one or more of the following non-limiting examples of anti-cancer agents:

1) alkylating agents, including but not limited to carmustine, chlorambucil (LEUKERAN), cisplatin (PLATIN), carboplatin (PARAPLATIN), oxaliplatin (ELOXATIN), streptozocin (ZANOSAR), busulfan (MYLERAN), dacarbazine, ifosfamide, lomustine (CCNU), melphalan (ALKERAN), procarbazine (MATULAN), temozolomide (TEMODAR), thiotepa, and cyclophosphamide (ENDOXAN);
2) anti-metabolites, including but not limited to cladribine (LEUSTATIN), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), raltitrexed;
3) antimitotics, which are often plant alkaloids and terpenoids, or derivateves thereof, including but not limited to taxanes such as docetaxel (TAXITERE) and paclitaxel (ABRAXANE, TAXOL); vinca alkaloids such as vincristine (ONCOVIN), vinblastine, vindesine, and vinorelbine (NAVELBINE);
4) topoisomerase inhibitors, including but not limited to camptothecin (CTP), irinotecan (CAMPTOSAR), topotecan (HYCAMTIN), teniposide (VUMON), and etoposide (EPOSIN);
5) cytotoxic antibiotics, including but not limited to actinomycin D (dactinomycin, COSMEGEN), bleomycin (BLENOXANE) doxorubicin (ADRIAMYCIN), daunorubicin (CERUBIDINE), epirubicin (ELLENCE), fludarabine (FLUDARA), idarubicin, mitomycin (MITOSOL), mitoxantrone (NOVANTRONE), plicamycin;
6) aromatase inhibitors, including but not limited to aminoglutethimide, anastrozole (ARIMIDEX), letrozole (FEMARA), vorozole (RIVIZOR), exemestane (AROMASIN);
7) angiogenesis inhibitors, including but not limited to genistein, sunitinib (SUTENT) and bevacizumab (AVASTIN);
8) anti-steroids and anti-androgens such as aminoglutethimide (CYTADREN), bicalutamide (CASODEX), cyproterone, flutamide (EULEXIN), nilutamide (NILANDRON);
9) tyrosine kinase inhibitors, including but not limited to imatinib (GLEEVEC), erlotinib (TARCEVA), lapatininb (TYKERB), sorafenib (NEXAVAR), and axitinib (INLYTA);
10) mTOR inhibitors such as everolimus, temsirolimus (TORISEL), and sirolimus;
11) monoclonal antibodies such as trastuzumab (HERCEPTIN) and rituximab (RITUXAN);
12) other agents, such as amsacrine; *Bacillus* Calmette-Guerin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon; leucovorin; leuprolide (LUPRON); levamisole; lonidamine; mesna; metformin; mitotane (o,p'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone.

For use in treatment of multiple sclerosis, a STING agonist may be optimally used together with one or more of the following non-limiting examples of agents: glatiramer, corticosteroids, muscle relaxants such as tizanidine (ZANAFLEX) or baclofen (LIORESAL), agents to reduce fatigue, such as amantadine (SYMMETREL), modafinil (PROVIGIL), and agents to alleviate depression, pain, and bladder or bowel control problems.

In some embodiments, a STING agonist may be optimally used together with one or more of the following non-limiting examples of immune checkpoint inhibitors: CTLA-4, PD-1, Tim-3, Vista, BTLA, LAG-3 and TIGIT pathway antagonists; PD-1 pathway blocking agents; PD-L1 inhibitors; including without limitation anti-PD-1 antibodies nivolumab, pembrolizumab or pidilizumab; PD-1 inhibitor AMP-224; anti-CTLA-4 antibody ipilimumab; and anti-PD-L1 antibodies BMS-936559, MPDL3280A, MEDI4736, and avelumab.

In some embodiments, a STING agonist may be optimally used together with one or moe of the following non-limiting examples of antibody therapeutical agents: muromonab-CD3, infliximab (REMICADE), adalimumab (HUMIRA), omalizumab (XOLAIR), daclizumab (ZENAPAX), rituximab (RITUXAN), ibritumomab (ZEVALIN), tositumomab (BEXXAR), cetuximab (ERBITUX), trastuzumab (HERCEPTIN), ADCETRIS, alemtuzumab (CAMPATH-1H), Lym-1 (ONCOLYM), ipilimumab (YERVOY), vitaxin, bevacizumab (AVASTIN), and abciximab (REOPRO).

Where a subject is suffering from or at risk of suffering from an inflammatory condition, a STING agonist compound described herein is optionally used together with one or more agents or methods for treating an inflammatory condition in any combination. Therapeutic agents/treatments for treating an autoimmune and/or inflammatory condition include, but are not limited to any of the following examples:

1) corticosteroids, including but not limited to cortisone, dexamethasone, and methylprednisolone;
2) nonsteroidal anti-inflammatory drugs (NSAIDs), including but not limited to ibuprofen, naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONSTEL), nabumetone (RELAFEN) and piroxicam (FELDENE);
3) immunosuppressants, including but not limited to methotrexate (RHEUMATREX), leflunomide (ARAVA), azathioprine (IMURAN), cyclosporine (NEORAL, SANDIMMUNE), tacrolimus and cyclophosphamide (CYTOXAN);
4) CD20 blockers, including but not limited to rituximab (RITUXAN);
5) Tumor Necrosis Factor (TNF) blockers, including but not limited to etanercept (ENBREL), infliximab (REMICADE) and adalimumab (HUMIRA);

6) interleukin-1 receptor antagonists, including but not limited to anakinra (KINERET);

7) interleukin-6 inhibitors, including but not limited to tocilizumab (ACTEMRA);

8) interleukin-17 inhibitors, including but not limited to AIN457;

9) Janus kinase inhibitors, including but not limited to tasocitinib; and 10) syk inhibitors, including but not limited to fostamatinib.

The compositions may also be administered in combination with radiotherapy, surgical therapy, immunotherapy, cryotherapy, gene therapy, or any other therapy known for use by the person of ordinary skill in the art.

Combination therapies may be applied during the same time period, or sequentially, or with overlapping time intervals. Nonsequential combination therapy may alternate between the two or more therapies. In some situations, it may be desirable to extend the time period for administration of a certain therapy. In some situations, it may be desirable to shorten or prolong the time period between therapies.

List of Abbreviations

DCI=4,5-dicyanoimidazole; DDTT=3-((dimethylaminomethylidene)amino)-3H-1,2,4-dithiazole-5-thione; DMAP=4-Dimethylaminopyridine; DMOCP=2-chloro-5,5-dimethyl-2-oxo-1,3,2-dioxaphosphorinane; DMTr=dimethoxytrityl=(4-methoxyphenyl)$_2$(phenyl)methyl; Piv=pivaloyl=$(CH_3)_3C$—$C(=O)$—; NaOH=sodium hydroxide; M=molar; mL=milliliter; h=hour; min.=minute; HCl=hydrogen chloride; $H_2O$=water; MS=mass spectrometry; ES+=electrospray positive ionization; $^1$H-NMR=proton nuclear magnetic resonance; $^{31}$P-NMR=phosphorous nuclear magnetic resonance; MHz=megahertz; H=hydrogen; RT=room temperature; ° C.=Celsius; $Br_2$=bromine; $NaHSO_3$=sodium bisulfite; NMP=N-Methyl-2-pyrrolidone; MW=microwave; KF=potassium fluoride; Pd(dppf)Cl$_2$=[1,1-bis(diphenylphosphino)ferrocene]palladium(II) dichloride; PE=petroleum ether; EtOAc=ethyl acetate; EA=ethyl acetate; CDCl$_3$=deuterated chloroform; DMSO-d$_6$=dimethyl sulfoxide deuterated-6; CD$_3$CN=deuterated acetonitrile; MeOH=methanol; D$_2$O=deuterated water; prep-HPLC=preparative high pressure liquid chromatography, also known as preparative high performance liquid chromatography; DMSO=dimethyl sulfoxide; MeCN=acetonitrile; NH$_3$=ammonia; NH$_4$OH=ammonium hydroxide; NIS=N-iodosuccinimide; DMF=dimethylformamide; K$_3$PO$_4$=potassium phosphate, tribasic; N$_2$=nitrogen; Py=pyridine; THF=tetrahydrofuran; TEA=triethylamine; TBSCl=tert-butyldimethylsilyl chloride; TEAB=tetraethyl ammonium bicarbonate; TMSCl=trimethylsilyl chloride;

TFA=trifluoroacetic acid; DCM=dichloromethane; K$_2$CO$_3$=potassium carbonate; ul=microliter.

General Synthetic Methods for Preparing Compounds

The following schemes can be used to practice the present invention.

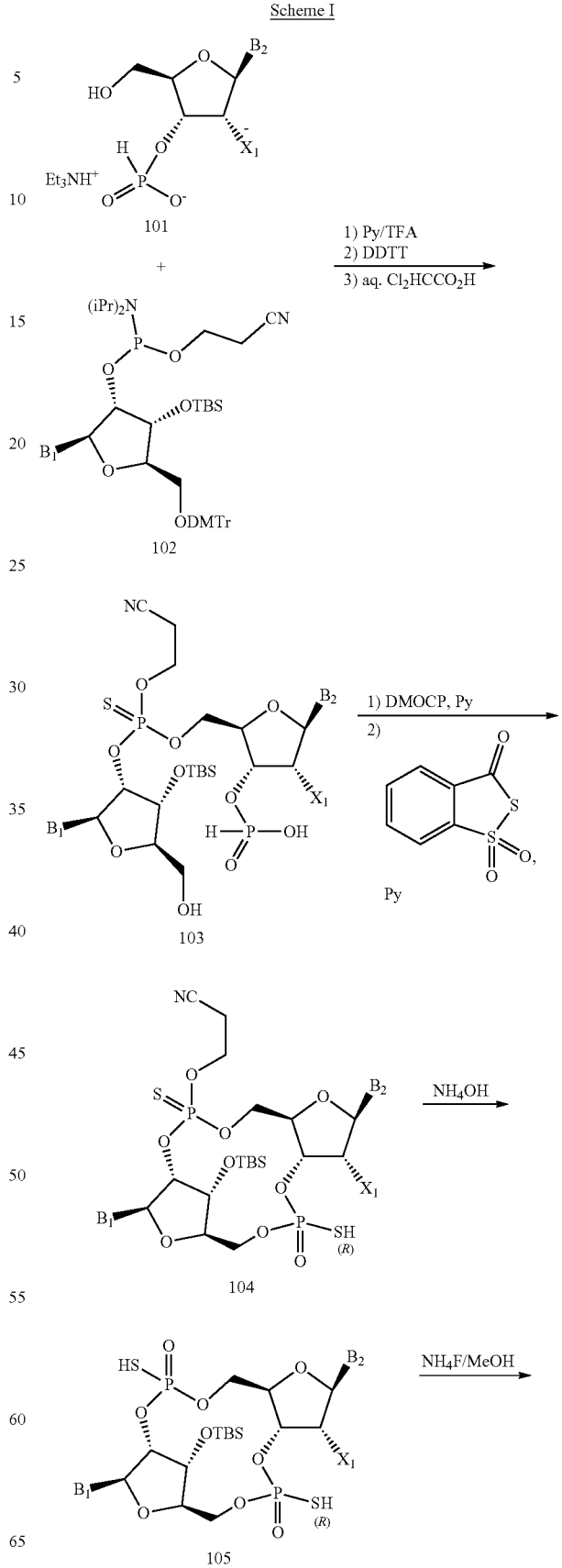

Scheme I

-continued

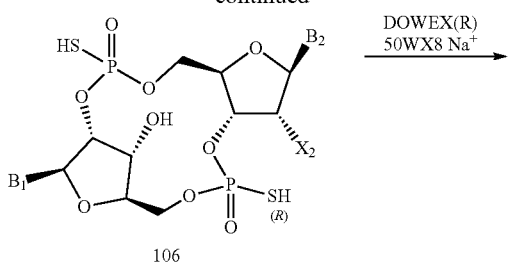

106

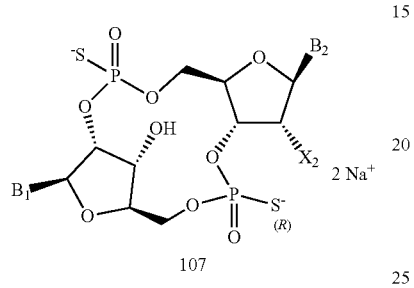

107

X₁ = OTBS, F, Cl
X₂ = OH, F, Cl

Compounds disclosed herein can be synthesized using the following general synthetic procedure set forth in Scheme I, employing variations which will be apparent to those skilled in the art. Nucleotide or nucleotide analogue 101, having an unprotected 5' hydroxyl, and nucleotide or nucleotide analogue 102, having a phosphoramidite moiety at its 2' hydroxyl, are coupled with pyridinium fluoride. The intermediate phosphite is oxidatively sulfurized with DDTT, giving a mixture of $R_P$ and $S_P$ diastereoisomers at the phosphorothioate center.

In a third step, dichloroacetic acid is used to remove the DMTr group on the fragment derived from 102. Intermediate 103 is then cyclized with DMOCP, then oxidatively sulfurized with Beaucage reagent (3H-1,2-benzodithiol-3-one 1,1-dioxide). Stereochemistry at the newly formed phosphorothioate center can result in a mixture of $R_p$ and $S_p$ stereoisomers. Based on literature precedent (Gaffney, B. L. et al. Org. Lett. 2010, 12(14), 3269-3271; Zhao, J. et al. Nucleosides Nucleotides Nucl Acids 2009, 28, 352-378; Battistini, C. et al. Tetrahedron 1993, 49, 1115-1132.), the stereochemistry at this center is often, but not always, assigned as $R_p$, and is indicated as (R) in Scheme 1. Synthesis is completed by removal of the cyanoethyl group of 104 with ammonia, followed by removal of the silyl protecting groups of 105 with fluoride. Cyclic dinucleotides 106 are obtained as a mixture of diastereoisomers, typically assigned as $R_PR_P$ and $S_PR_P$ at the phosphorothioate centers based on the above literature precedent. It is also possible that more than two diastereoisomers may be obtained in some cases. The diastereoisomers can be separated and obtained in substantially pure form via reverse phase HPLC purification. If desired, the anionic form can be obtained by treatment with ion exchange resin. Without limitation, the disodium salt can be obtained in this fashion.

The invention is further illustrated by the following examples.

INTERMEDIATE A (2R,3R,4R,5R)-2-(4-benzamido-7H-pyrrolo[2,3-d]pyrimidin-7-yl)-5-((bis(4-methoxyphenyl)(phenyl)methoxy)methyl)-4-((tert-butyldimethylsilyl)oxy)tetrahydrofuran-3-yl (2-cyanoethyl) diisopropylphosphoramidite

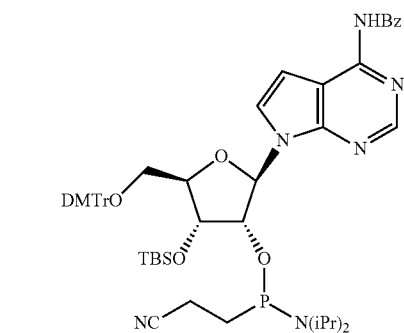

Step 1

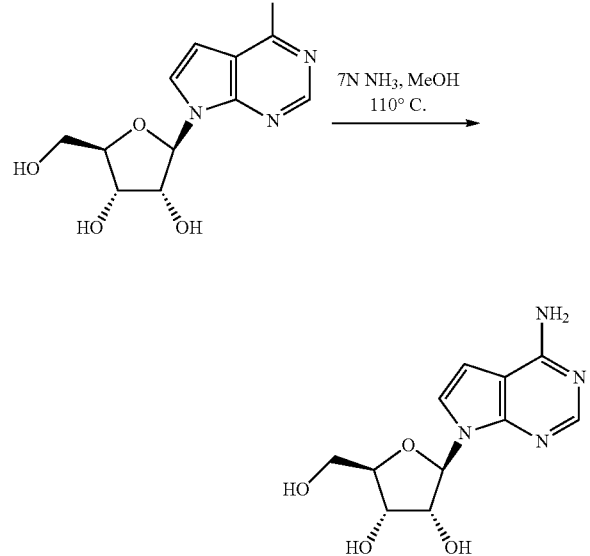

(2R,3R,4S,5R)-2-(4-amino-7H-pyrrolo[2,3-d]pyrimidin-7-yl)-5-(hydroxymethyl)-tetrahydrofuran-3,4-diol A mixture of (2R,3R,4S,5R)-2-(4-chloro-7H-pyrrolo[2,3-d]-pyrimidin-7-yl)-5-(hydroxymethyl)tetrahydrofuran-3,4-diol (7.0 g, 24.5 mmol) and 7 N $NH_3$ in MeOH (70 mL) was stirred at 110° C. for 16 h in a pressure safe steel vessel. The mixture was cooled to RT and the volatiles were removed under reduced pressure. Ten batches of this reaction were run in parallel. The residues were combined and triturated with MeOH (500 ml) to give the title compound as an off-white solid.

Step 2

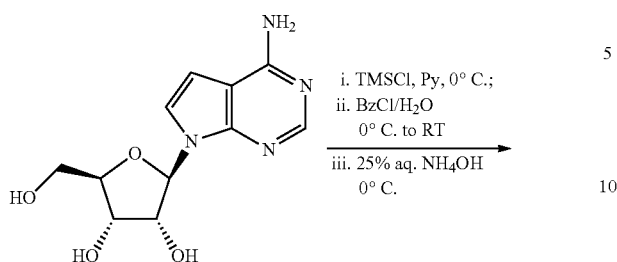

N-(7-((2R,3R,4S,5R)-3,4-dihydroxy-5-(hydroxymethyl)tetrahydrofuran-2-yl)-7H-pyrrolo[2,3-d]pyrimidin-4-yl)benzamide To a solution of the product from the previous step (65.2 g, 245 mmol) in pyridine (1.14 L) at 0° C. was added TMSCl (119.8 g, 1.10 mol, 4.5 eq) dropwise over 30 minutes. The mixture was stirred for further 30 minutes at 0° C., and BzCl (6 g, 34.9 mmol, 1.5 eq) was then added dropwise. The resulting mixture was allowed to stir at RT for 16 h, cooled to 0° C. and then quenched with H$_2$O (200 mL), followed by 25% aq. NH$_4$OH (500 mL). The volatiles were removed under reduced pressure; the residue was diluted in H$_2$O (1.5 L) and extracted with EtOAc (3×2.0 L). The organic layer was dried over anhydrous Na$_2$SO$_4$, filtered and concentrated under reduced pressure. The residue was purified by SiO$_2$ gel chromatography (DCM:MeOH=20:1) to afford the title compound (60.7 g, 0.164 mol, 67% over two steps).

MS(ES$^+$) C$_{18}$H$_{19}$N$_4$O$_5$ requires: 371, found: 370.8 [M+H]$^+$; $^1$H-NMR (400 MHz, DMSO-d$_6$) δ ppm 11.15 (s, 1H), 8.61 (s, 1H), 8.07 (d, J=7.4 Hz, 2H), 7.74 (d, J=3.8 Hz, 1H), 7.61-7.67 (m, 1H), 7.52-7.58 (m, 2H), 6.69 (d, J=3.6 Hz, 1H), 6.24 (d, J=6.4 Hz, 1H), 5.38 (d, J=6.4 Hz, 1H), 5.18 (d, J=4.8 Hz, 1H), 5.08 (t, J=5.5 Hz, 1H), 4.43 (q, J=6.1 Hz, 1H), 4.09-4.15 (m, 1H), 3.93 (q, J=3.6 Hz, 1H), 3.52-3.68 (m, 2H).

Step 3

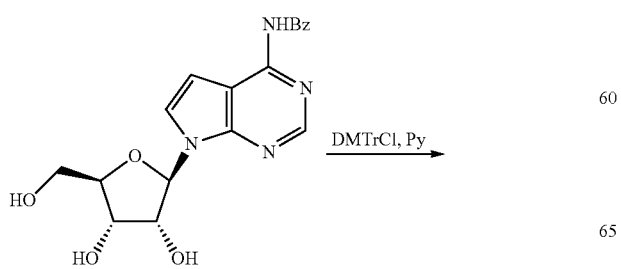

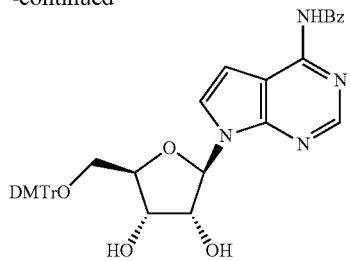

N-(7-((2R,3R,4S,5R)-5-((bis(4-methoxyphenyl)(phenyl)methoxy)methyl)-3,4-dihydroxytetrahydrofuran-2-yl)-7H-pyrrolo[2,3-d]pyrimidin-4-yl)benzamide To a solution of the product from the previous step (60.0 g, 162.0 mmol) in pyridine (420 mL) was added DMTrCl (65.87 g, 194.4 mmol, 1.2 eq). The mixture was stirred at RT for 16 h, diluted with CH$_2$Cl$_2$ (1.0 L), washed with sat NaHCO$_3$ (2×500 mL), H$_2$O (500 mL) and brine (500 mL). The organic layer was dried over anhydrous Na$_2$SO$_4$, filtered and concentrated under reduced pressure. The residue was purified by SiO$_2$ gel chromatography (5/1 petroleum ether/EtOAc to 100% EtOAc) to afford the title compound (89.3 g, 132.8 mmol, 82%) as a white foam.

Step 4

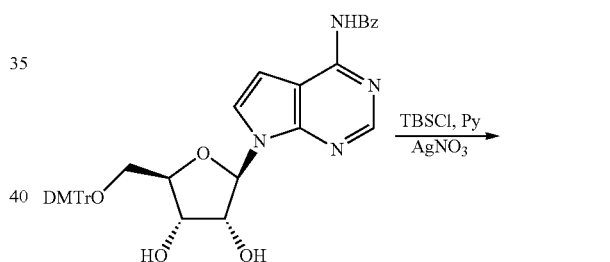

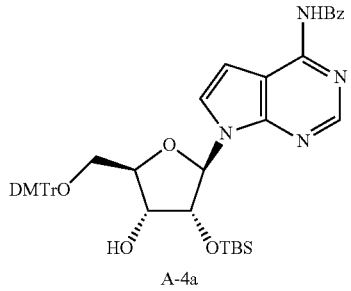

A-4a

+

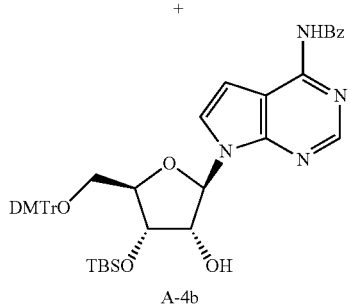

A-4b

N-(7-((2R,3R,4S,5R)-5-((bis(4-methoxyphenyl)(phenyl)methoxy)methyl)-3-(tert-butyldimethylsilyloxy)-4-hydroxy-tetrahydrofuran-2-yl)-7H-pyrrolo[2,3-d]pyrimidin-4-yl)benzamide (A-4a) and N-(7-((2R,3R,4S,5R)-5-((bis(4-methoxyphenyl)-(phenyl)methoxy)methyl)-3-hydroxy-4-(tert-butyldimethylsilyloxy)-tetrahydrofuran-2-yl)-7H-pyrrolo[2,3-d]pyrimidin-4-yl)benzamide (A-4b)

To a mixture of the product from the previous step (55 g, 81.76 mmol) and AgNO$_3$ (22.92 g, 134.9 mmol, 22.7 mL, 1.65 eq) in THF (400 mL) was added TBSCl (78.75 g, 522.48 mmol, 1.76 eq). The reaction mixture was stirred at RT for 5 h, filtered and concentrated under reduced pressure. The residue was purified by SiO$_2$ gel chromatography (Petroleum Ether/EtOAc=10/1 to 2/1) to afford A-4a (70 g, 88.9 mmol, 54.4%) and A-4b (7 g, 8.89 mmol, 5.4%).

A-4a: $^1$H-NMR (400 MHz, DMSO-d$_6$) δ ppm 11.16 (br s, 1H), 8.58 (s, 1H), 8.07 (d, J=7.7 Hz, 2H), 7.52-7.67 (m, 4H), 7.42 (d, J=7.7 Hz, 2H), 7.22-7.32 (m, 7H), 6.88 (d, J=8.8 Hz, 4H), 6.69 (d, J=3.8 Hz, 1H), 6.30 (d, J=5.4 Hz, 1H), 5.12 (d, J=5.8 Hz, 1H), 4.59 (t, J=5.3 Hz, 1H), 4.07-4.21 (m, 2H), 3.73 (s, 6H), 3.28 (br s, 2H), 0.75 (s, 9H), −0.04 (s, 3H), −0.16 (s, 3H).

A-4b: $^1$H-NMR (400 MHz, DMSO-d$_6$) δ ppm 11.76 (brs, 1H), 8.59 (s, 1H), 8.07 (d, J=7.8 Hz, 2H), 7.61-7.66 (m, 2H), 7.52-7.57 (m, 2H), 7.38 (br d, J=7.8 Hz, 2H), 7.19-7.32 (m, 7H), 6.86 (d, J=8.7 Hz, 4H), 6.68 (d, J=3.6 Hz, 1H), 6.21 (d, J=5.6 Hz, 1H), 5.38 (br d, J=5.9 Hz, 1H), 4.57 (br d, J=5.1 Hz, 1H), 4.34 (t, J=4.4 Hz, 1H), 4.00 (br d, J=4.1 Hz, 1H), 3.72 (s, 6H), 3.30-3.39 (m, 1H), 3.12-3.16 (m, 1H), 3.14 (br dd, J=4.7, 10.4 Hz, 1H), 0.84 (s, 9H), 0.08 (s, 3H), 0.03 (s, 3H).

Step 5

(2R,3R,4R,5R)-2-(4-benzamido-7H-pyrrolo[2,3-d]pyrimidin-7-yl)-5-((bis(4-methoxyphenyl)(phenyl)methoxy)methyl)-4-((tert-butyldimethylsilyl)oxy)tetrahydrofuran-3-yl (2-cyanoethyl) diisopropylphosphoramidite To a solution of A-4b (10.0 g, 12.71 mmol) in CH$_2$Cl$_2$ (100 mL) were added were added 3-((bis(diisopropylamino)phosphanyl)-oxy)propanenitrile (4.21 g, 14 mmol, 1.1 eq) and DCI (2.25 g, 19.07 mmol, 1.5 eq). The mixture was stirred at RT for 5 h, diluted with CH$_2$Cl$_2$ (100 mL) and washed with sat NaHCO$_3$ (3×100 mL). The organic layer was dried over Na$_2$SO$_4$, filtered and concentrated under reduced pressure. The residue was purified by SiO$_2$ gel chromatography (petroleum ether/EtOAc=10/1 to 3/1; 0.5% TEA) to afford the title compound (10.0 g, 9.72 mmol, 76%) as a white foam.

$^1$H-NMR (400 MHz, CD$_3$CN) δ ppm 9.23 (br s, 1H), 8.52 (br s, 1H), 8.01 (br d, J=5.8 Hz, 2H), 7.60-7.68 (m, 1H), 7.51-7.58 (m, 2H), 7.40-7.50 (m, 3H), 7.18-7.34 (m, 7H), 6.79-6.92 (m, 5H), 6.34-6.48 (m, 1H), 4.97-4.70 (m, 1H), 4.63-4.48 (m, 1H), 4.13 (br d, J=3.9 Hz, 1H), 3.84-3.69 (m, 7H), 3.62-3.41 (m, 4H), 3.27-3.15 (m, 1H), 2.58 (t, J=6.2 Hz, 1H), 2.41 (t, J=6.2 Hz, 1H), 1.12-1.03 (m, 9H), 0.91-0.84 (m, 12H), 0.13 (d, J=16.2 Hz, 3H), 0.05 (s, 3H); $^{31}$P NMR (162 MHz, CD$_3$CN) δ ppm 149.92, 149.53.

INTERMEDIATE B

(2R,3R,4R,5R)-5-(4-benzamido-7H-pyrrolo[2,3-d]pyrimidin-7-yl)-4-((tert-butyldimethylsilyl)oxy)-2-(hydroxymethyl)tetrahydrofuran-3-yl hydrogen phosphonate

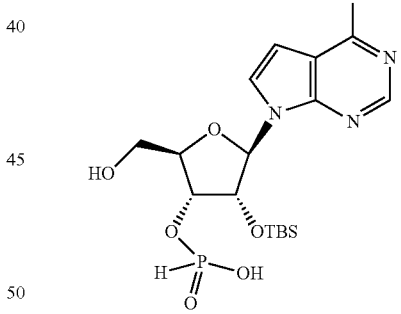

Step 1

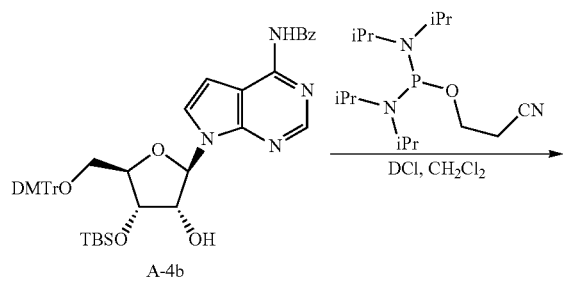

A-4b

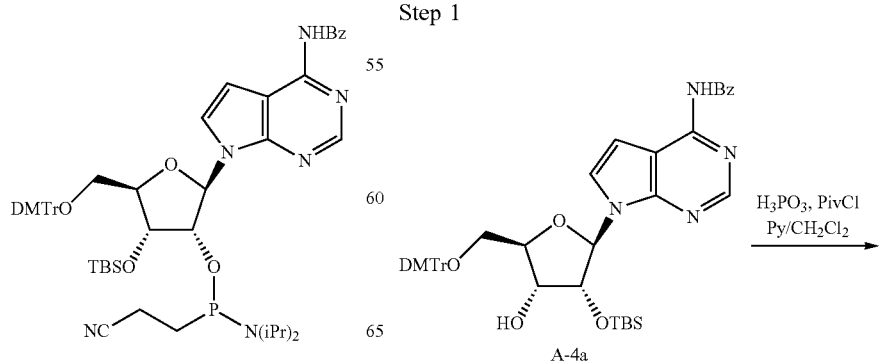

55

-continued

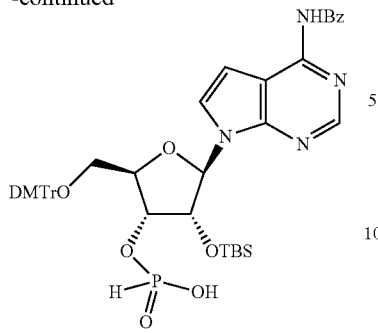

(2R,3R,4R,5R)-5-(4-benzamido-7H-pyrrolo[2,3-d]pyrimidin-7-yl)-2-((bis(4-methoxyphenyl)(phenyl)methoxy)methyl)-4-((tert-butyldimethylsilyl)oxy)tetrahydrofuran-3-yl hydrogen phosphonate Phosphorous acid (15.63 g, 190.6 mmol, 15 eq) was co-evaporated three times with anhydrous pyridine (5 mL) and then dissolved in anhydrous pyridine (75 mL) upon heating to ca. 45° C. The mixture was allowed to cool to RT. A-4a (10.0 g, 12.7 mmol) was added and the mixture was cooled to 0° C. Pivaloyl chloride (15.32 g, 127.07 mmol, 10.0 eq) was slowly added at 0° C. and the resulting mixture was allowed to warm to RT and stirred for 16 h. The reaction mixture was then quenched by 1 M aq. TEAB (100 mL) and extracted with EtOAc (3×1000 mL). The combined organic layers were washed with 0.5 M aq. TEAB (100 m L), and brine (1000 mL), dried over anhydrous Na$_2$SO$_4$, filtered and concentrated under reduced pressure. The residue was purified by SiO$_2$ gel chromatography (CH$_2$Cl$_2$/MeOH=50/1) to afford the title compound as a white foam (8.0 g, 8.38 mmol, 66%).

Step 2

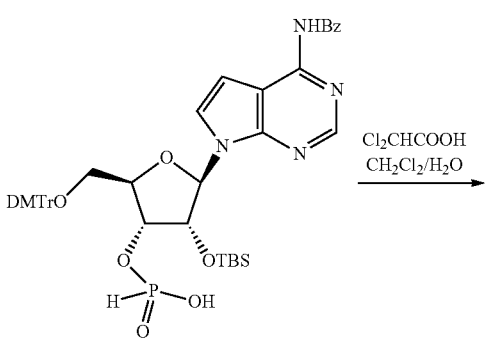

56

(2R,3R,4R,5R)-5-(4-benzamido-7H-pyrrolo[2,3-d]pyrimidin-7-yl)-4-((tert-butyldimethylsilyl)oxy)-2-(hydroxymethyl)tetrahydrofuran-3-yl hydrogen phosphonate The product from the previous step (40.0 g, 42.01 mmol) and H$_2$O (4.0 g, 222 mmol, 4.0 mL, 5.3 eq) were added to a solution of Cl$_2$CHCOOH in CH$_2$Cl$_2$ (6% v/v, 400 mL) and the reaction mixture was stirred at RT for 0.5 h, then washed with H$_2$O (4×200 mL). The organic layer was dried over anhydrous Na$_2$SO$_4$ and filtered. SiO$_2$ gel (80 g, previously treated with TEA) was combined with the filtrate, and the mixture was concentrated under reduced pressure to obtain free flowing SiO$_2$ gel powder. The residue was purified by SiO$_2$ gel column chromatography (CH$_2$Cl$_2$/MeOH=50/1 to 30/1) to give the title compound as a white solid (15.0 g, 23.08 mmol, 55%);

MS(ES$^+$) C$_{24}$H$_{34}$N$_4$O$_7$PSi requires: 549, found: 549.1 [M+H]$^+$; $^1$H-NMR (400 MHz, 400 MHz, DMSO-d$_6$) δ ppm 11.15 (br s, 1H), 8.49-8.74 (m, 1H), 8.08 (d, J=7.6 Hz, 2H), 7.78 (d, J=3.6 Hz, 1H), 7.60-7.67 (m, 1H), 7.51-7.57 (m, 2H), 6.74 (d, J=3.6 Hz, 1H), 6.28 (d, J=6.2 Hz, 1H), 5.75 (s, 1H), 4.56-4.74 (m, 2H), 4.16 (br s, 1H), 3.61-3.76 (m, 2H), 3.03 (q, J=7.2 Hz, 5H), 1.19 (t, J=7.4 Hz, 7H), 0.69 (s, 9H), −0.09 (s, 3H), −0.27 (s, 3H); $^{31}$P NMR (162 MHz, DMSO-d$_6$) δ ppm 0.72.

INTERMEDIATE C (2R,3R,4R,5R)-5-(6-benzamido-9H-purin-9-yl)-4-fluoro-2-(hydroxymethyl) tetrahydrofuran-3-yl hydrogen phosphonate

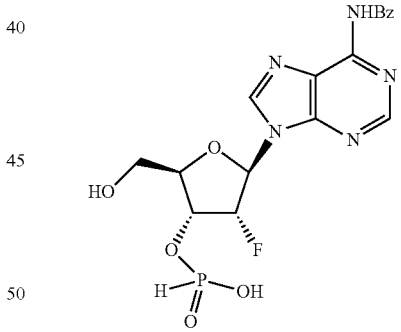

Step 1

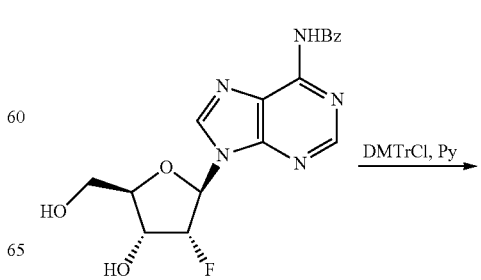

-continued

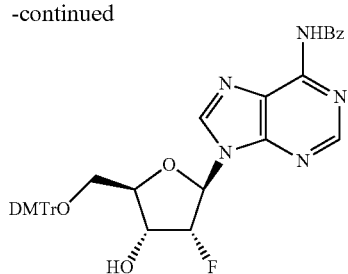

N-(9-((2R,3R,4R,5R)-5-((bis(4-methoxyphenyl)(phenyl)methoxy)methyl)-3-fluoro-4-hydroxytetrahydrofuran-2-yl)-9H-purin-6-yl)benzamide To a solution of N-(9-((2R,3R,4R,5R)-3-fluoro-4-hydroxy-5-(hydroxymethyl) tetrahydrofuran-2-yl)-9H-purin-6-yl)-benzamide (35 g, 93.7 mmol) in pyridine (180 mL) was added DMTrCl (38.12 g, 112.5 mmol, 1.2 eq) and the resulting mixture was stirred at RT for 16 h. The mixture was then diluted with $CH_2Cl_2$ (800 mL), washed with sat $NaHCO_3$ (2×400 mL) and brine (400 mL). The organic layer was dried over anhydrous $Na_2SO_4$, filtered and concentrated under reduced pressure. The residue was purified by $SiO_2$ gel chromatography (petroleum ether/EtOAc=10/1 to 1/4) to give the title compound as a white solid (53.0 g, 78.4 mmol, 84%).

$^1$H-NMR (400 MHz, DMSO-$d_6$) δ ppm 11.26 (br s, 1H), 8.74 (s, 1H), 8.62 (s, 1H), 8.05 (d, J=7.4 Hz, 2H), 7.60-7.72 (m, 1H), 7.48-7.58 (m, 2H), 7.32 (d, J=7.2 Hz, 2H), 7.14-7.24 (m, 7H), 6.80 (dd, J=6.2, 8.7 Hz, 4H), 6.43 (d, J=20.0 Hz, 1H), 5.73-5.85 (m, 1H), 5.61 (d, J=4.4 Hz, 1H), 4.76-4.99 (m, 1H), 4.14 (br d, J=5.4 Hz, 1H), 3.64-3.79 (m, 7H), 3.19-3.33 (m, 2H).

Step 2

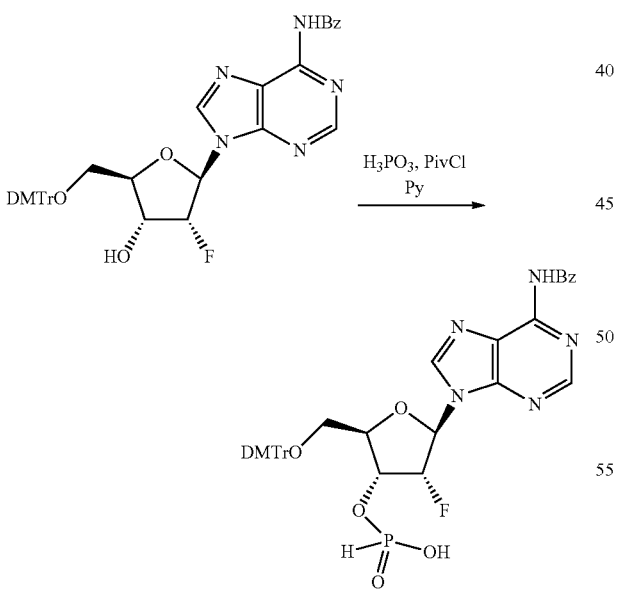

(2R,3R,4R,5R)-5-(6-benzamido-9H-purin-9-yl)-2-((bis(4-methoxyphenyl)-(phenyl)methoxy)methyl)-4-fluorotetrahydrofuran-3-yl hydrogen phosphonate Phosphorous acid (18.2 g, 222 mmol, 15 eq) was co-evaporated three times with anhydrous pyridine (15 mL) and then dissolved with heating in anhydrous pyridine (150 mL). The mixture was allowed to cool to RT. The product from the previous step (10 g, 14.8 mmol) was added, and the resulting mixture was cooled to 0° C. Pivaloyl chloride (17.85 g, 148 mmol, 10 eq) was slowly added at 0° C. and the resulting mixture was allowed to warm to RT and stirred for 16 h. The reaction mixture was then quenched with 1 M aq. TEAB (150 mL) and extracted with EtOAc (3×900 mL). The combined organic layers were washed with 0.5 M aq. TEAB (900 mL), brine (900 mL), dried over anhydrous $Na_2SO_4$, filtered and concentrated under reduced pressure. The residue was purified by $SiO_2$ gel chromatography ($CH_2Cl_2$/MeOH=50/1 to 20/1; 1% TEA) to give the title compound as a white foam (38 g).

Step 3

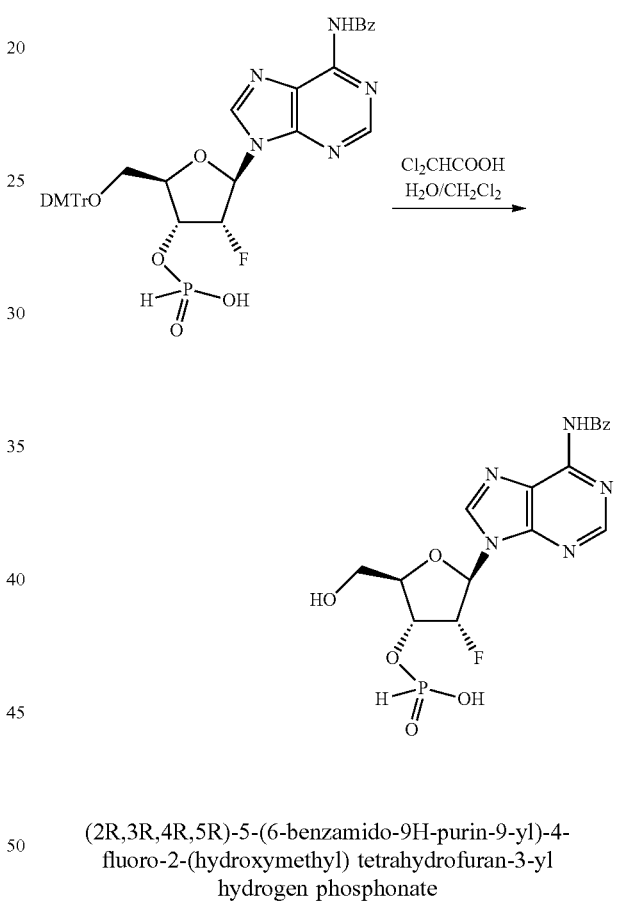

(2R,3R,4R,5R)-5-(6-benzamido-9H-purin-9-yl)-4-fluoro-2-(hydroxymethyl) tetrahydrofuran-3-yl hydrogen phosphonate The product from the previous step (38 g, 45.19 mmol) and $H_2O$ (4.0 g, 222 mmol, 4.0 mL, 5 eq) were added to a solution of $Cl_2CHCOOH$ in $CH_2Cl_2$ (6% v/v, 380 mL) and the reaction mixture was stirred at RT for 0.5 h. The reaction mixture was filtered to give a red solid, which was washed with $CH_2Cl_2$ (2×20 mL) to give the title compound as a white solid (15 g, 30.87 mmol, 68%).

$^1$H-NMR (400 MHz, DMSO-$d_6$) δ ppm 11.24 (br s, 1H), 8.78 (s, 1H), 8.73 (s, 1H), 8.02-8.08 (m, 2H), 7.76 (d, J=1.2 Hz, 0.5H), 7.62-7.68 (m, 1H), 7.53-7.59 (m, 2H), 6.69 (s, 1H), 6.46 (dd, J=3.2, 16.6 Hz, 1H), 6.07 (d, J=1.4 Hz, 0.5H), 5.87-5.91 (m, 1H), 5.73-5.78 (m, 1H), 5.17-5.28 (m, 1H), 4.22-4.28 (m, 1H), 3.64-3.84 (m, 2H).

INTERMEDIATE D (2R,3R,4R,5R)-2-(6-benzamido-9H-purin-9-yl)-5-((bis(4-methoxyphenyl)(phenyl)-methoxy)methyl)-4-((tert-butyldimethylsilyl)oxy)tetrahydrofuran-3-yl (2-cyanoethyl) diisopropylphosphoramidite

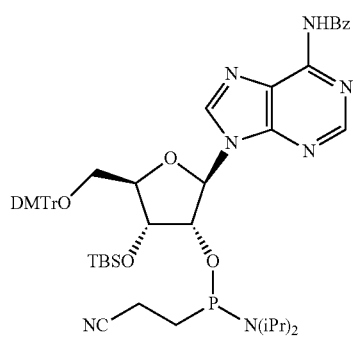

Step 1

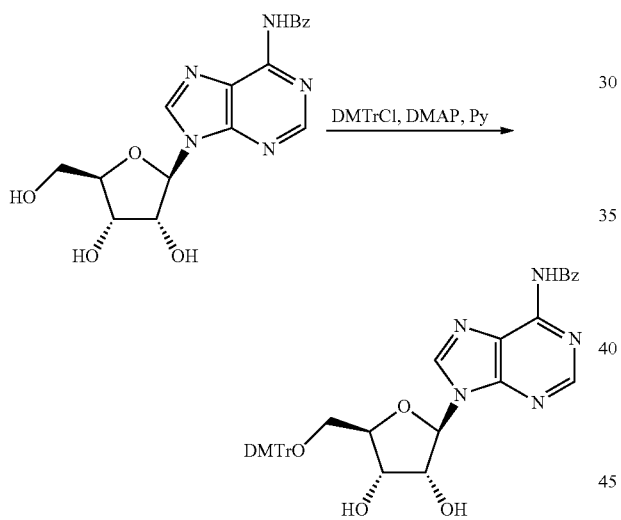

N-(9-((2R,3R,4S,5R)-5-((bis(4-methoxyphenyl)(phenyl)methoxy)methyl)-3,4-dihydroxytetrahydrofuran-2-yl)-9H-purin-6-yl)benzamide To a solution of N-(9-((2R,3R,4S,5R)-3,4-dihydroxy-5-(hydroxymethyl)tetrahydrofuran-2-yl)-9H-purin-6-yl)-benzamide (100 g, 269.3 mmol) in pyridine (500 mL) at 0° C. were added DMAP (1.64 g, 13.46 mmol, 0.05 eq) and DMTrCl (100.4 g, 296.2 mmol, 1.1 eq). The reaction mixture was stirred at RT for 16 h, then quenched by addition of MeOH (500 mL). The volatiles were removed under reduced pressure and the residue was purified by SiO₂ gel chromatography (1/1 petroleum ether/EtOAc to 100% EtOAc) to give the title compound as a white foam (150 g, 223 mmol, 83%).

Step 2

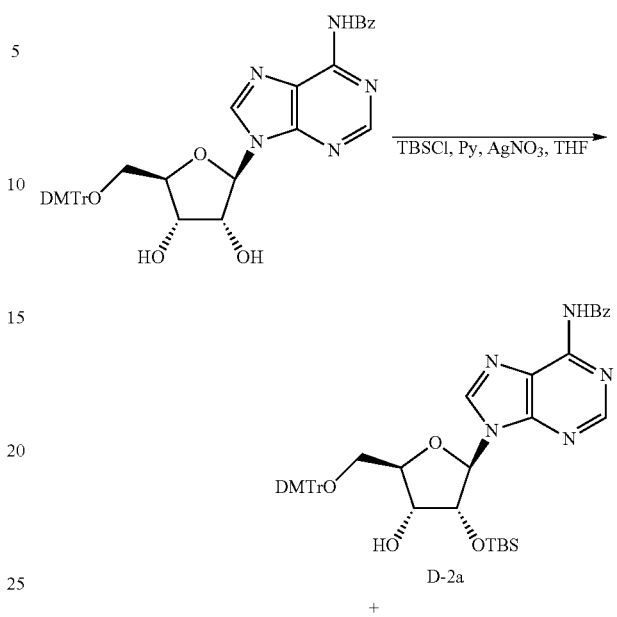

N-(9-((2R,3R,4S,5R)-5-((bis(4-methoxyphenyl)(phenyl)methoxy)methyl)-3-(tert-butyldimethylsilyloxy)-4-hydroxytetrahydrofuran-2-yl)-9H-purin-6-yl)benzamide (D-2a) and N-(9-((2R,3R,4S,5R)-5-((bis(4-methoxyphenyl)(phenyl)methoxy)methyl)-4-(tert-butyl-dimethylsilyloxy)-3-hydroxytetrahydrofuran-2-yl)-9H-purin-6-yl)benzamide (D-2b)

To a solution of the product from the previous step (200 g, 296.9 mmol) in THF (800 mL) and pyridine (15 mL) were added AgNO₃ (83.2 g, 489.8 mmol, 82 mL, 1.65 eq) and TBSCl (78.7 g, 522.5 mmol, 1.76 eq), and the mixture was stirred at RT for 16 h. The reaction mixture was filtered, diluted with H₂O (1.0 L) and extracted with EtOAc (3×1.0 L). The combined organic layers were washed with brine (2×1.0 L), dried over anhydrous Na₂SO₄ and concentrated under reduced pressure. The residue was purified by SiO₂ gel chromatography (petroleum ether/EtOAc=3/1 to 1/1) to give D-2a (114 g, 145 mmol, 49%) and D-2b (53 g, 68 mmol, 23%).

Step 3

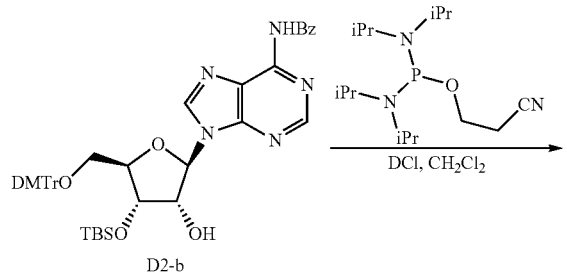

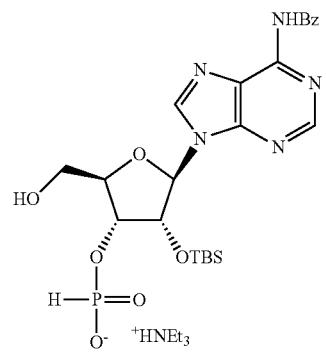

(2R,3R,4R,5R)-2-(6-benzamido-9H-purin-9-yl)-5-((bis(4-methoxyphenyl)-(phenyl)methoxy)methyl)-4-((tert-butyldimethylsilyl)oxy)tetrahydrofuran-3-yl (2-cyanoethyl) diisopropylphosphoramidite To a solution of D-2b (19.0 g, 24.1 mmol) in MeCN (200 mL) at 0° C. were added 3-((bis(diisopropylamino)phosphanyl)oxy)propanenitrile (7.99 g, 26.5 mmol, 1.1 eq) and DCI (3.42 g, 28.9 mmol, 1.2 eq), and the resulting mixture was stirred for 3 h at RT under $N_2$ atmosphere. The volatiles were removed under reduced pressure and the residue was purified by $SiO_2$ gel chromatography (petroleum ether/EtOAc=4/1 to 1.5/1; 1% TEA) to give the title compound as a white foam (20.5 g, 20.74 mmol, 86%).

MS(ES+) $C_{53}H_{67}N_7O_8PSi$ requires: 988, found: 987.8 [M+H]+; 1H-NMR (400 MHz, $CD_3CN$) δ ppm 8.57 (s, 1H), 8.26 (s, 1H), 7.91 (br d, J=7.6 Hz, 2H), 7.57 (m, 1H), 7.47-7.49 (m, 2H), 7.17-7.21 (m, 9H), 6.73-6.76 (m, 4H), 6.10-6.19 (m, 1H), 5.10-5.14 (m, 1H), 4.64-4.68 (m, 1H), 4.10-4.14 (m, 1H), 3.25-3.75 (m, 7H), 3.40-3.51 (m, 4H), 3.15-3.18 (m, 1H), 2.58 (t, J=6.0 Hz, 1H), 2.41 (t, J=6.0 Hz, 1H), 1.03-1.06 (m, 9H), 0.76-0.86 (m, 12H), 0.00-0.93 (m, 6H); 31P NMR (162 MHz, $CD_3CN$) δ ppm 150.32, 149.58.

INTERMEDIATE E (2R,3R,4R,5R)-5-(6-benzamido-9H-purin-9-yl)-4-((tert-butyldimethylsilyl)oxy)-2-(hydroxymethyl)tetrahydrofuran-3-yl hydrogen phosphonate triethylammonium salt

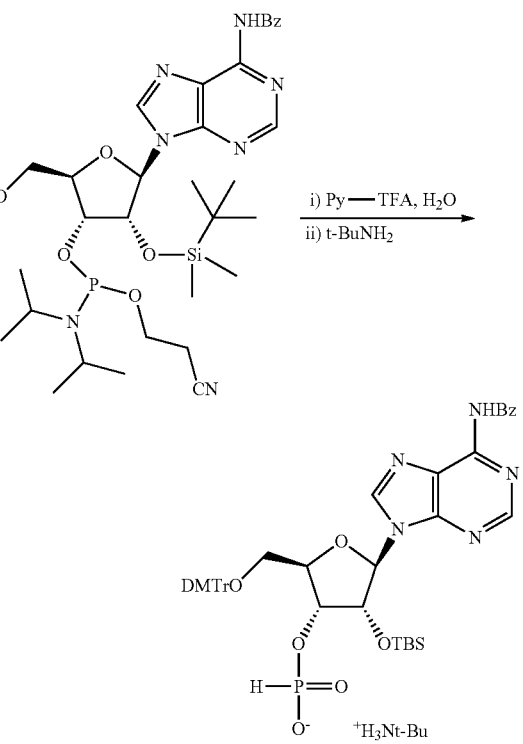

Step 1

(2R,3R,4R,5R)-5-(6-benzamido-9H-purin-9-yl)-2-((bis(4-methoxyphenyl)-(phenyl)methoxy)methyl)-4-((tert-butyldimethylsilyl)oxy)tetrahydrofuran-3-yl (2-cyanoethyl) hydrogen phosphonate To a solution of (2R,3R,4R,5R)-5-(6-benzamido-9H-purin-9-yl)-2-((bis(4-methoxyphenyl)(phenyl)methoxy)methyl)-4-((tert-butyldimethylsilyl)-oxy)tetrahydrofuran-3-yl (2-cyanoethyl) diisopropylphosphoramidite (25 g, 25.3 mmol) in MeCN (12 mL) was added $H_2O$ (912 mg, 50.6 mmol, 2.0 eq) and pyridinium trifluoroacetate (5.86 g, 30.36 mmol, 1.2 eq) and the resulting mixture was stirred for 5 minutes at RT. tert-Butylamine (1.85 g, 25.3 mmol, 1.0 eq) was added and the resulting mixture was stirred for further 25 minutes at RT and then concentrated under reduced pressure to give the title compound (23.4 g) as a white foam, which was used in the next step without further purification.
Step 2

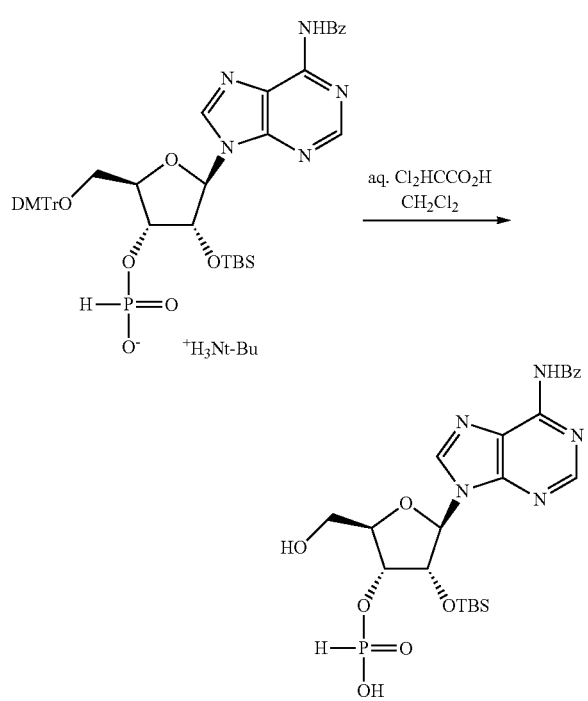

(2R,3R,4R,5R)-5-(6-benzamido-9H-purin-9-yl)-4-((tert-butyldimethylsilyl)oxy)-2-(hydroxymethyl)tetrahydrofuran-3-yl hydrogen phosphonate The crude product from the previous step (23.4 g, 25.3 mmol) was added to a solution of Cl₂CHCOOH in CH₂Cl₂ (6% v/v, 200 mL). H₂O (2.28 g, 126 mmol, 5.0 eq) was added and the resulting mixture was stirred for 20 minutes at RT. The reaction mixture was quenched by the addition of pyridine (30 mL) at RT, and was then concentrated under reduced pressure. The residue was purified by SiO₂ gel chromatography (CH₂Cl₂/MeOH=20/1 to 5/1) to give the title compound (15 g, 24.1 mmol).
Step 3

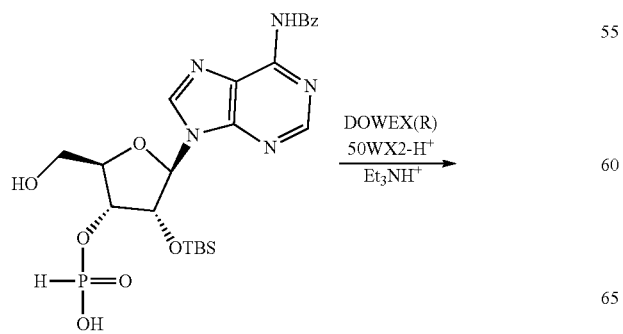

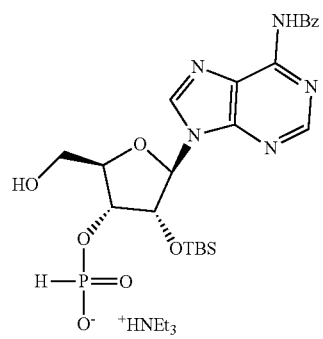

(2R,3R,4R,5R)-5-(6-benzamido-9H-purin-9-yl)-4-((tert-butyldimethylsilyl)oxy)-2-(hydroxymethyl)tetrahydrofuran-3-yl hydrogen phosphonate triethylammonium salt The product from the previous step was dissolved in MeOH (100 mL), TEA resin (50.0 g; prepared from DOWEX® 50WX2-H⁺ by washing with deionized water until pH=7; then with 1N aq. TEA; then again with deionized water until pH=7; then MeOH) was added and the mixture was stirred at RT for 0.5 h. The reaction mixture was filtered, the filtrate was concentrated under reduced pressure to give the title compound as a TEA salt (yellow solid; 15 g, 23 mmol, 95%).

$^1$H-NMR (400 MHz, DMSO-$d_6$) δ ppm 8.57 (s, 1H), 8.26 (s, 1H), 7.91 (br d, J=7.6 Hz, 2H), 7.57 (m, 1H), 7.47-7.49 (m, 2H), 7.17-7.21 (m, 9H), 6.73-6.76 (m, 4H), 6.10-6.19 (m, 1H), 5.10-5.14 (m, 1H), 4.64-4.68 (m, 1H), 4.10-4.14 (m, 1H), 3.25-3.75 (m, 7H), 3.40-3.51 (m, 4H), 3.15-3.18 (m, 1H), 2.58 (t, J=6.0 Hz, 1H), 2.41 (t, J=6.0 Hz, 1H), 1.03-1.06 (m, 9H), 0.76-0.86 (m, 12H), 0.00-0.93 (m, 6H).

INTERMEDIATE F (2R,3R,4R,5R)-5-(6-benzamido-9H-purin-9-yl)-4-chloro-2-(hydroxymethyl)tetrahydrofuran-3-yl hydrogen phosphonate

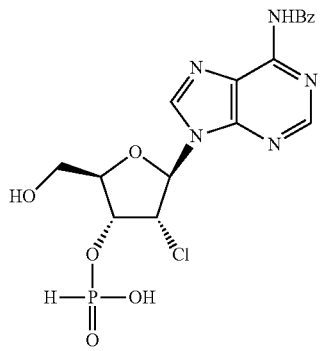

Step 1

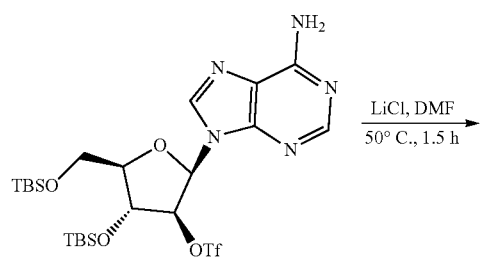

A mixture of (2R,3S,4R,5R)-2-(6-amino-9H-purin-9-yl)-4-((tert-butyldimethylsilyl)oxy)-5-(((tert-butyldimethylsilyl)oxy)methyl)tetrahydrofuran-3-yl trifluoromethanesulfonate (69.0 g, 0.11 mol, 1.0 eq) and LiCl (51.2 g, 1.21 mol, 11.0 eq) in DMF (600 mL) was heated at 50° C. for 1.5 h. The reaction mixture was diluted with DCM (500 mL) and washed with H$_2$O (300 mL×3). The organic layer was dried over Na$_2$SO$_4$, filtered and concentrated under reduced pressure. The residue was purified by SiO$_2$ gel chromatography (PE:EtOAc=1:1) to give the title compound (46.0 g, 89.5 mmol, 81.4% yield) as a yellow solid.

$^1$H NMR (400 MHz CDCl$_3$) δ ppm 8.30-8.38 (m, 1H), 8.06 (s, 1H), 6.20 (d, J=5.9 Hz, 1H), 5.82-5.95 (m, 2H), 4.96-5.04 (m, 1H), 4.56-4.63 (m, 1H), 4.17 (q, J=3.5 Hz, 1H), 3.96 (dd, J=11.4, 4.3 Hz, 1H), 3.77 (dd, J=11.4, 3.0 Hz, 1H), 0.92 (d, J=13.9 Hz, 18H), 0.14 (d, J=8.8 Hz, 6H), 0.08 (s, 6H).

Step 2.

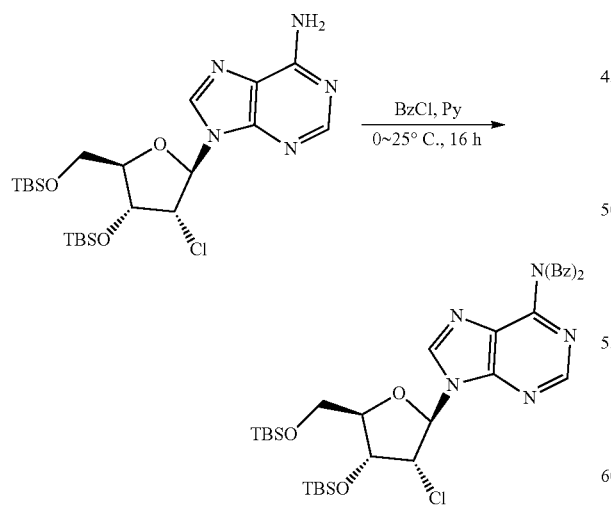

To a solution of the product from previous step (46.0 g, 89.4 mmol, 1.0 eq) in Py (460 mL) at 0° C. was added BzCl (25.2 g, 179 mmol, 20.5 mL, 2.0 eq) dropwise under N$_2$, and the resulting mixture was stirred at 25° C. for 16 hrs. The reaction was diluted with H$_2$O (200 mL) and extracted with EtOAc (200 mL×3). The combined organic layers were dried over Na$_2$SO$_4$, filtered and concentrated under reduced pressure to give N-benzoyl-N-(9-((2R,3R,4R,5R)-4-((tert-butyldimethylsilyl)oxy)-5-(((tert-butyldimethylsilyl)oxy)methyl)-3-chlorotetrahydrofuran-2-yl)-9H-purin-6-yl)benzamide (60.0 g) as yellow oil which was used for the next step without further purification. MS(ES$^+$) C$_{36}$H$_{48}$ClN$_5$O$_5$Si$_2$ requires: 721, found: 722 [M+H]$^+$;

Step 3

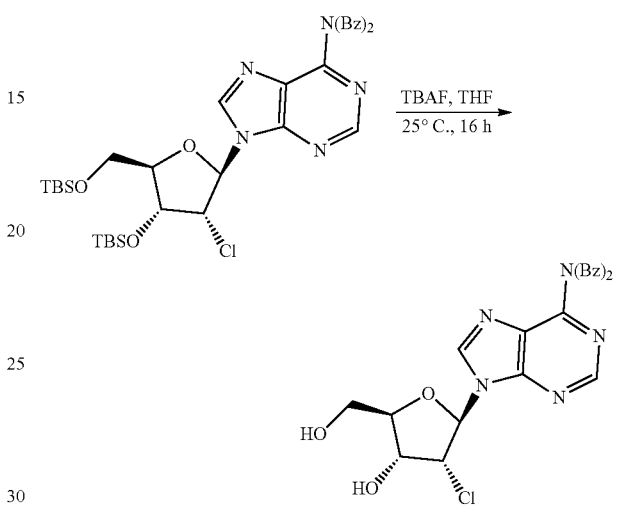

To a solution of the product from previous step (60.0 g, 97 mmol, 1.0 eq) in THF (600 mL) was added TBAF (1 M in THF, 290 mL, 3.0 eq). Then the mixture was stirred at 25° C. for 16 hrs. The volatiles were removed under reduced pressure to give N-benzoyl-N-(9-((2R,3R,4R,5R)-3-chloro-4-hydroxy-5-(hydroxymethyl)tetrahydrofuran-2-yl)-9H-purin-6-yl)benzamide (48.0 g) as a yellow oil which was used for the next step without further purification. MS(ES$^+$) C$_{24}$H$_{20}$ClN$_5$O$_5$ requires: 493, found: 494 [M+H]$^+$;

Step 4

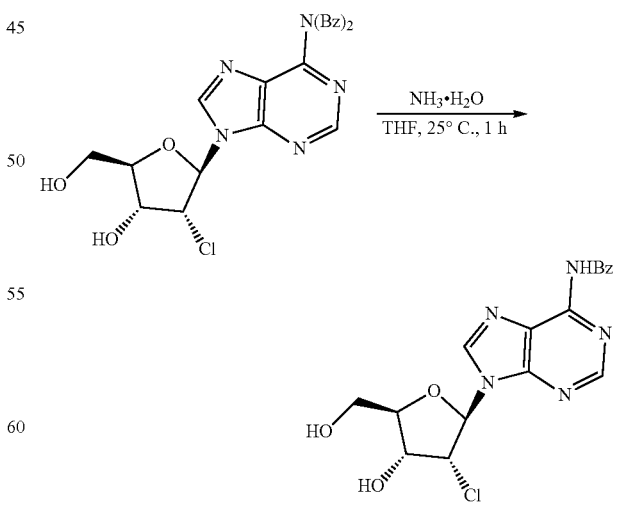

To a solution of the product from previous step (48.0 g, 97.2 mmol, 1.0 eq) in THF (500 mL) was added NH$_3$·H$_2$O (28% in water, 8.0 mL, 7.28 g, 54.0 mmol, 0.5 eq). The resulting mixture was stirred at 25° C. for 1 hr, during which time a solid product was formed. The suspension was filtered and the filter cake was washed with THF (300 mL×3). The filtrate was concentrated under reduced pressure to give N-(9-((2R,3R,4R,5R)-3-chloro-4-hydroxy-5-(hydroxymethyl)tetrahydrofuran-2-yl)-9H-purin-6-yl)benzamide (36 g, 92.3 mmol, 95% yield) as a white solid product; MS(ES+) $C_{17}H_{16}ClN_5O_4$ requires: 389, found: 390 [M+H]+;

Steps 5 to 7

(2R,3R,4R,5R)-5-(6-benzamido-9H-purin-9-yl)-4-chloro-2(hydroxymethyl)tetrahydrofuran-3-yl hydrogen phosphonate (Intermediate F)

white solid (13.0 g, 27.8 mmol, 30% over three steps); $^1$H NMR: (400 MHz DMSO-$d_6$) δ ppm 11.28 (br s, 1H), 8.78 (br d, J=4.0 Hz, 2H), 8.05 (br d, J=7.4 Hz, 2H), 7.60-7.68 (m, 1H), 7.55 (br t, J=7.5 Hz, 2H), 6.34 (br d, J=5.9 Hz, 1H), 5.27 (br d, J=5.1 Hz, 1H), 5.02 (br s, 1H), 4.30 (br s, 1H), 3.74 (br s, 2H), 3.01-3.11 (m, 2H); $^{31}$P NMR: (162 MHz DMSO-$d_6$) δ 0.63 ppm.

EXAMPLE 1a AND EXAMPLE 1b

Cyclic dinucleotides RR-CD-A-7dA and SR-CD-A-7dA dithio-[$R_p$, $R_p$]-cyclic-[A(2',5')p-7dA(3',5')p] dithio-[$S_p$, $R_p$]-cyclic-[A(2',5')p-7dA (3',5')p]

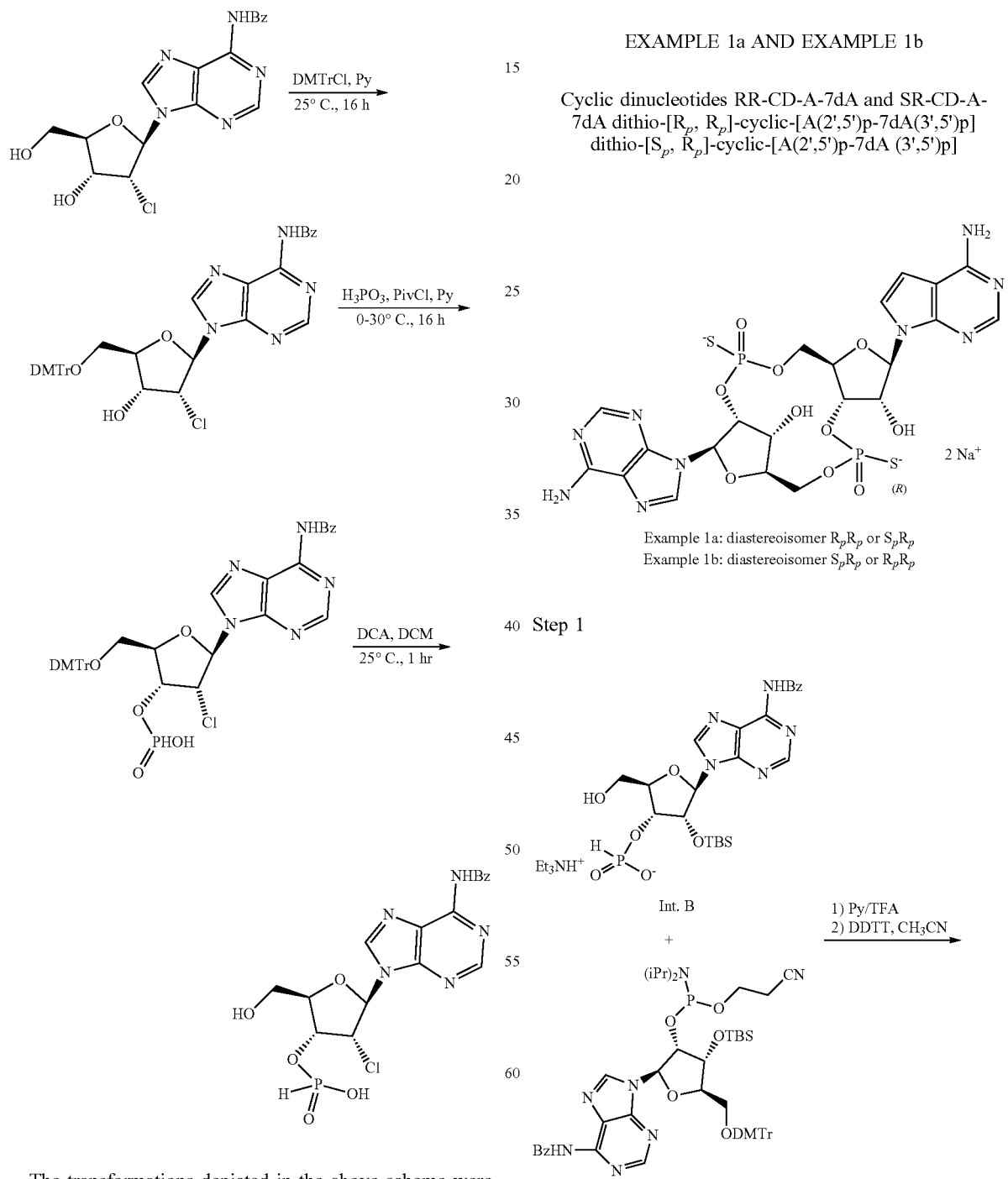

Example 1a: diastereoisomer $R_pR_p$ or $S_pR_p$
Example 1b: diastereoisomer $S_pR_p$ or $R_pR_p$ Step 1

The transformations depicted in the above scheme were performed according to the procedures previously described for the synthesis of Intermediate C, steps 1 to 3.

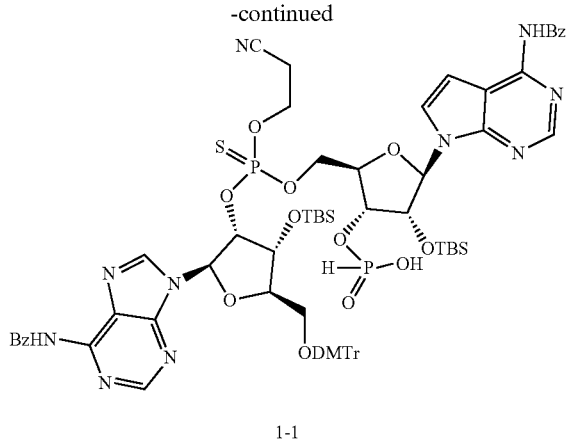

1-1

Compound 1-1

To a solution of Intermediate B (4.00 g, 6.16 mmol) in CH₃CN (50 mL) was added pyridine-TFA (2.38 g, 12.3 mmol, 2.0 eq) followed by a mixture of Intermediate D (6.70 g, 6.78 mmol, 1.10 eq) and 3 Å molecular sieves (1.0 g, 24.6 mmol, 4.0 eq) in CH₃CN (50 mL), and the resulting mixture was stirred for 30 minutes at RT. DDTT (1.52 g, 7.39 mmol, 1.20 eq) was then added and the mixture was stirred at RT for further 30 minutes. The volatiles were removed under reduced pressure to afford the crude compound 1-1 (9.04 g), which was used without further purification in the next step.

Step 2

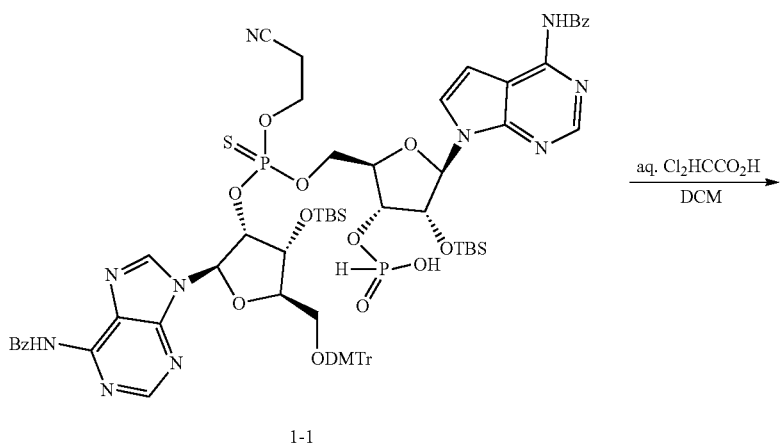

1-1 aq. Cl₂HCCO₂H
DCM

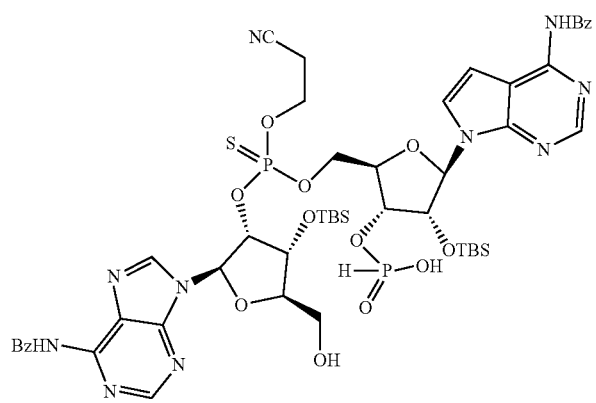

1-2

Compound 1-2

To a solution of $Cl_2CHCOOH$ in $CH_2Cl_2$ (6% v/v, 200 mL) was added $H_2O$ (2.0 g, 111 mmol, 2.0 mL, 18.0 eq) and compound 1-1 from the previous step (9.04 g, assume 6.16 mmol). The reaction mixture was stirred at RT for 0.5 h, then quenched with pyridine (120 mL) and concentrated under reduced pressure, to afford crude compound 1-2 (7.18 g), which was used without further purification in the next step.

$MS(ES^+)$ $C_{50}H_{67}N_{10}O_{13}P_2SSi_2$ requires: 1165, found: 1165.3 $[M+H]^+$.

Step 3

Compound 1-3

To a solution of compound 1-2 from the previous step (7.18 g, assume 6.16 mmol) in pyridine (50 mL) was added DMOCP (3.98 g, 21.6 mmol, 3.5 eq). The mixture was stirred for 0.5 h at RT. To the mixture was then added Beaucage reagent (3H-1,2-benzodithiol-3-one 1,1-dioxide, 1.85 g, 9.24 mmol, 1.5 eq), and the resulting mixture and stirred at RT for further 30 minutes. The reaction mixture was quenched by addition of 3.4% aq. $NaHCO_3$ (1.0 L), and then extracted with EtOAc (2×500 mL). The combined organic layers were washed with brine (300 mL), dried over anhydrous $Na_2SO_4$, filtered and concentrated under reduced pressure. The residue was purified by $SiO_2$ gel chromatography ($CH_2Cl_2$/MeOH=30/1 to 15/1) to give compound 1-3 (3.0 g, 2.04 mmol) as a mixture of diastereoisomers which was used as such in the following step.

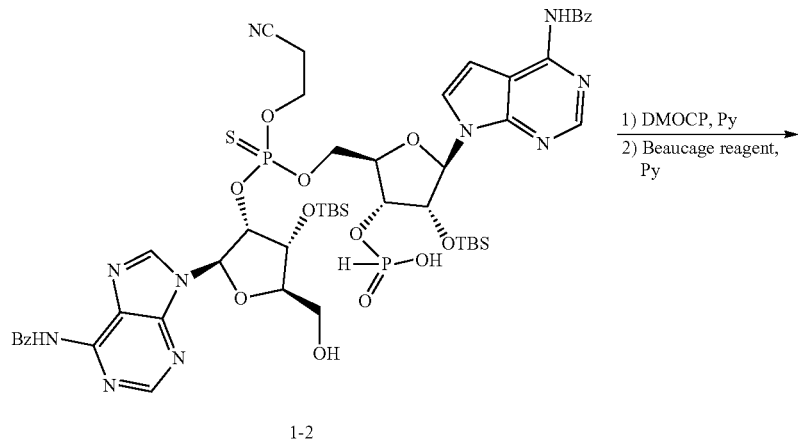

1-2

1) DMOCP, Py
2) Beaucage reagent, Py

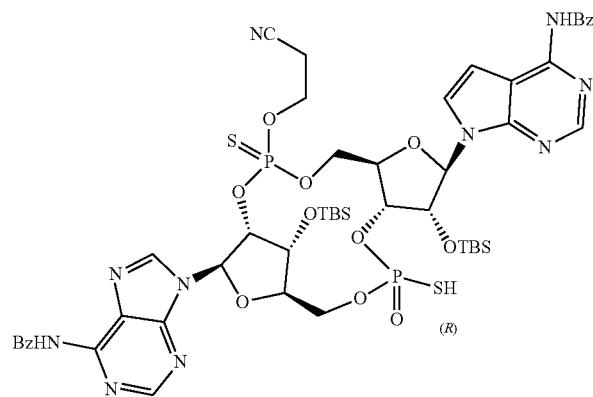

1-3

Step 4

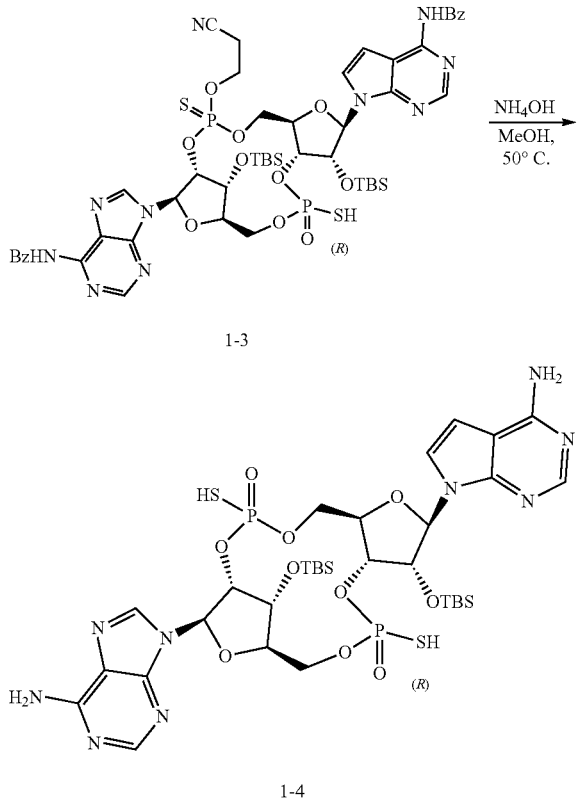

1-3

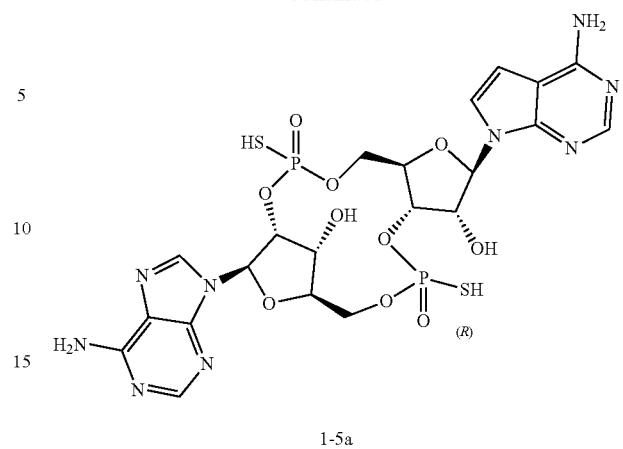

1-5a

Compound 1-5

To a solution of compound 1-4a (200 mg, 218 umol) in MeOH (5.0 mL) was added NH$_4$F (80.7 mg, 2.18 mmol, 10.0 eq) and the resulting mixture was stirred at 60° C. for 16 h. The volatiles were removed under reduced pressure and the residue was purified by prep-HPLC [Waters Xbridge 150*25 5 um; mobile phase: A: H$_2$O (10 mM NH$_4$HCO$_3$); B: MeCN; A %-B %=1%-20%, 10.5 minutes] to give compound 1-5a (30 mg, 40 umol) as a white solid.

Reaction of compound 1-4b in a similar manner afforded compound 1-5b (30 mg, 40 umol) as a white solid.

Step 6

Compound 1-4

To a solution of compound 1-3 from the previous step (3.0 g, 2.04 mmol) in MeOH (30 mL) was added NH$_4$OH (32.8 g, 935 mmol, 458 eq). The mixture was stirred at 50° C. for 12 h in a pressure safe steel vessel, then concentrated under reduced pressure. The residue was purified by prep-HPLC (PHENOMENEX® LUNA® C18 250*50 um; mobile phase: A: H$_2$O (10 mM NH$_4$HCO$_3$); B: MeCN; A %-B %=20%-50%, 20 minutes) to give two products: compound 1-4a (R$_p$R$_p$ or S$_p$R$_p$ diastereoisomer; 380 mg, 0.391 mmol;) and compound 1-4b (S$_p$R$_p$ or R$_p$R$_p$ diastereoisomer; 350 mg, 0.349 mmol) as a white solids.

Step 5

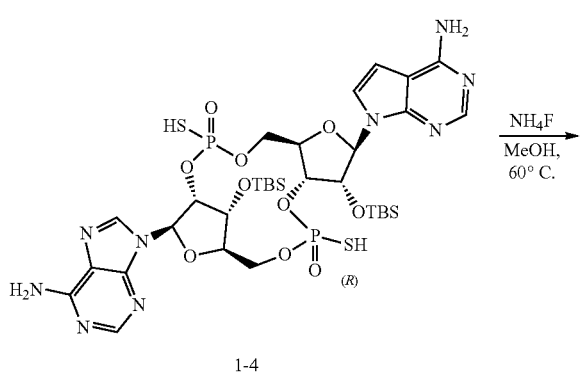

1-4

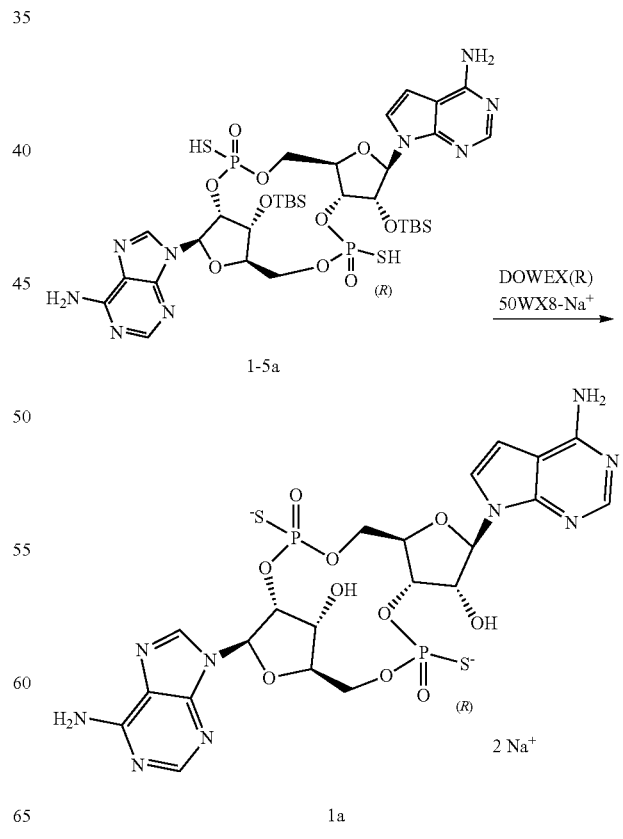

1a (1R,6R,8R,9R,10R,12R,15R,17R,18R)-17-(6-amino-9H-purin-9-yl)-8-(4-amino-7H-pyrrolo[2,3-d]pyrimidin-7-yl)-9,18-dihydroxy-3,12-dimercapto-2,4,7,11,13,16-hexaoxa-3λ$^5$, 12λ$^5$-diphosphatricyclo [13.2.1.0$^{6,10}$]octadecane-3,12-dione (1-5), disodium salt (Example 1a and Example 1b)

To a solution of compound 1-5a (30.0 mg, 41.5 umol) in H$_2$O (5.0 mL) was added DOWEX®-50WX8 (Na$^+$ form; 300 mg) and the mixture was stirred at RT for 0.5 h. The reaction was then filtered, and the filtrate was lyophilized to give Example 1a (R$_p$, R$_p$ or S$_p$, R$_p$ 28.0 mg, 38.1 umol) as a white solid.

MS(ES$^+$) C$_{21}$H$_{26}$N$_9$O$_{10}$P$_2$S$_2$ requires: 690, found: 690.0 [M+H]$^+$; $^1$H-NMR (400 MHz, DMSO-d$_6$) δ ppm 8.52 (s, 1H), 8.26 (s, 1H), 8.19 (s, 1H), 7.50 (d, J=3.6 Hz 1H), 6.85 (d, J=3.6 Hz, 1H), 6.09-6.13 (m, 2H), 5.46 (d, J=8.8 Hz, 1H), 5.28-5.30 (m, 1H) 4.63 (d, J=4 Hz, 1H), 4.03-4.27 (m, 5H), 3.64-3.69 (m, 2H); $^{31}$P NMR (162 MHz, DMSO-d$_6$) δ ppm 60.19, 56.77; R$_t$=1.797 minutes [Waters XBridge Shield RP18 2.1*50 mm, 5 um; mobile phase: A: H$_2$O+10 mM NH$_4$HCO$_3$; B: MeCN; A %-B %=0%-30%, 5.2 minutes]

Reaction of compound 1-5b in a similar manner gave Example 1b (S$_p$, R$_p$ or R$_p$, R$_p$ 30.0 mg, 39.6 umol) as a white solid.

MS(ES$^+$) C$_{21}$H$_{26}$N$_9$O$_{10}$P$_2$S$_2$ requires: 690, found: 690.0 [M+H]$^+$; $^1$H-NMR (400 MHz, DMSO-d$_6$) δ ppm 8.50 (s, 1H), 8.29 (s, 1H), 8.19 (s, 1H), 7.62 (d, J=3.2 Hz 1H), 6.85 (d, J=4.0 Hz, 1H), 6.09-6.14 (m, 2H), 5.19-5.29 (m, 2H), 4.68 (dd, J=7.6 Hz, 1H), 4.37 (d, J=4.0 Hz, 1H), 4.11-4.20 (m, 3H), 3.95-3.99 (m, 1H), 3.69-3.81 (m, 2H); $^{31}$P NMR (162 MHz, CD$_3$OD) δ ppm 59.29, 51.96; R$_t$=2.101 minutes [Waters XBridge Shield RP18 2.1*50 mm, 5 um; mobile phase: A: H$_2$O+10 mM NH$_4$HCO$_3$; B: MeCN; A %-B %=0%-30%, 5.2 minutes].

EXAMPLE 2a AND EXAMPLE 2b

Cyclic dinucleotides RR-CD-A-2'F-A and SR-CD-A-2'F-A; dithio-[R$_p$, R$_p$]-cyclic-[A(2',5')p-2'F-A(3',5')p]dithio-[S$_p$, R$_p$]-cyclic-[A(2',5')p-2'F-A (3',5')p]

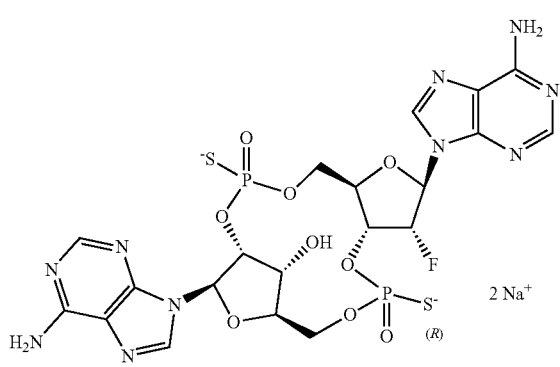

Example 2a: diastereoisomer R$_p$R$_p$ or S$_p$R$_p$
Example 2b: diastereoisomer S$_p$R$_p$ or R$_p$R$_p$ Step 1

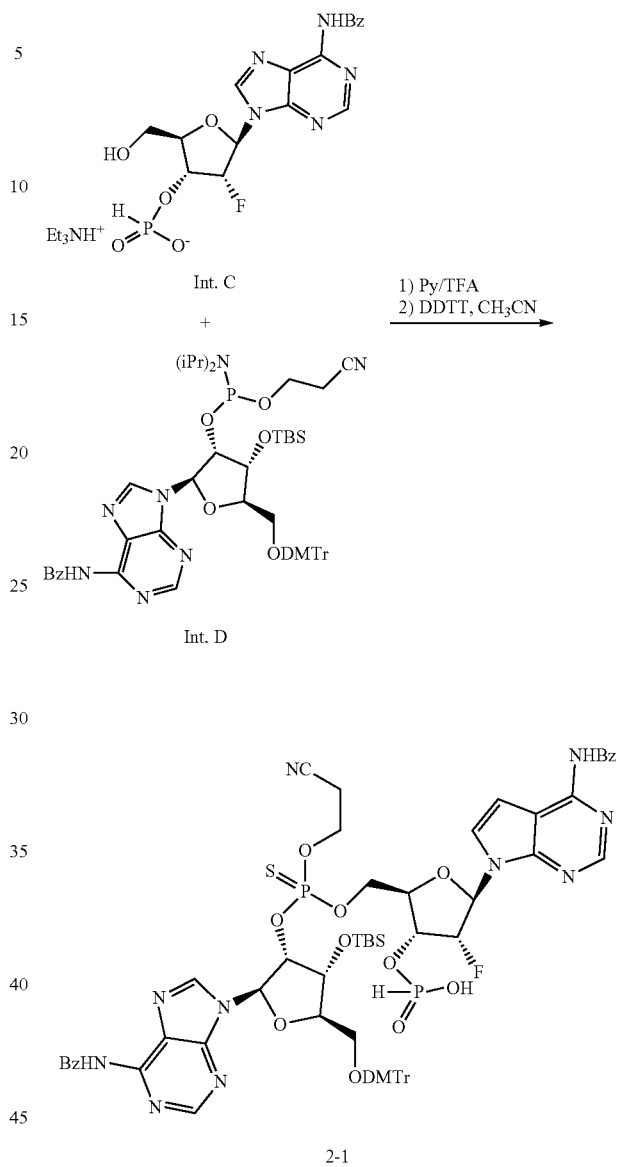

Compound 2-1

To a solution of Intermediate C (4.0 g, 9.15 mmol) in CH$_2$Cl$_2$ (40 ml) was added TEA (463 mg, 4.58 mmol, 0.50 eq). The mixture was stirred for 5 minutes at RT and the volatiles were removed under reduced pressure. The residue was dissolved in CH$_3$CN (40.00 mL) and pyridine-TFA (3.53 g, 18.3 mmol, 2.0 eq) was added, followed by a mixture of Intermediate D (9.04 g, 9.15 mmol, 1.0 eq) and 3 Å molecular sieves (1.48 g, 36.6 mmol, 4.0 eq) in CH$_3$CN (40 mL), and the resulting mixture was stirred for 30 minutes at RT. DDTT (2.25 g, 10.98 mmol, 1.2 eq) was added and the mixture was stirred at RT for further 30 minutes. The volatiles were removed under reduced pressure to afford the crude compound 2-1 (12.4 g), which was used without further purification in the next step.

Step 2
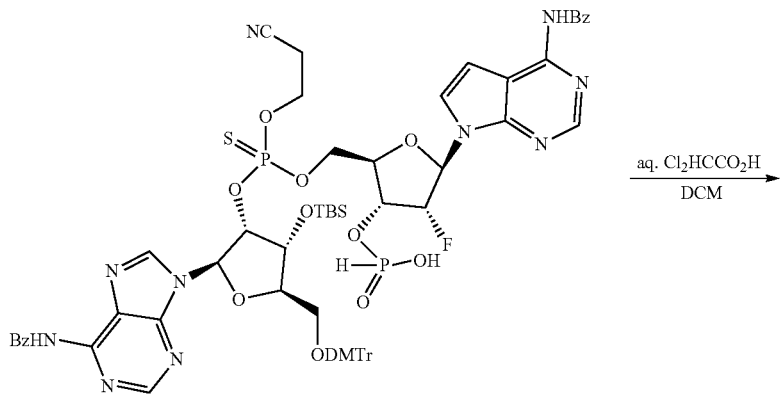
2-1
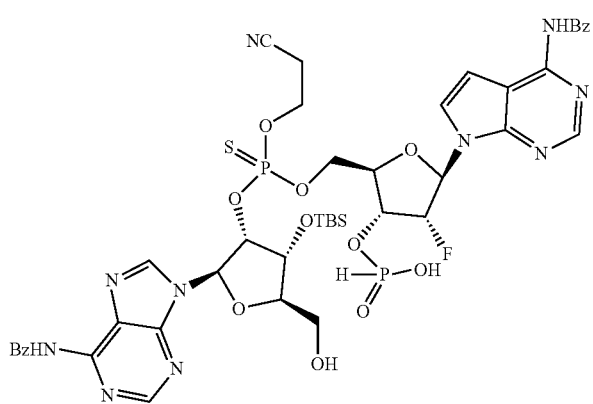
2-2
Compound 2-2
To a solution of Cl₂CHCOOH in CH₂Cl₂ (6% v/v, 200 mL) was added compound 2-1 from the previous step (12.4 g, assume 9.15 mmol) and H₂O (2.00 g, 111 mmol, 2.0 mL, 12.1 eq). The reaction mixture was stirred at RT for 0.5 h, then quenched with pyridine (100 mL) and concentrated under reduced pressure to afford compound 2-2 (9.64 g), which was used without further purification in the next step.
Step 3
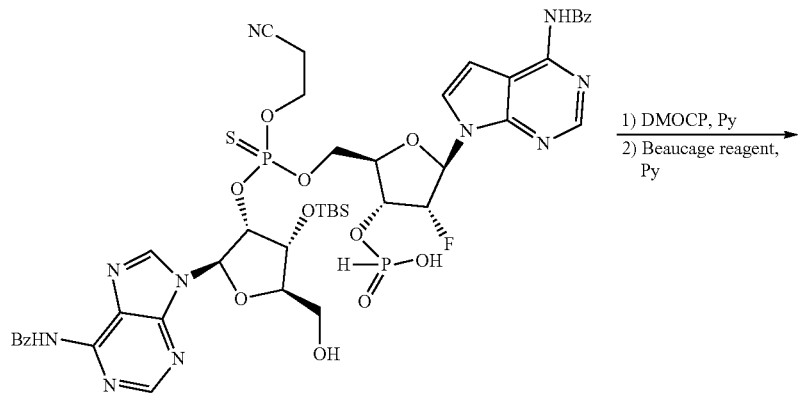
2-2

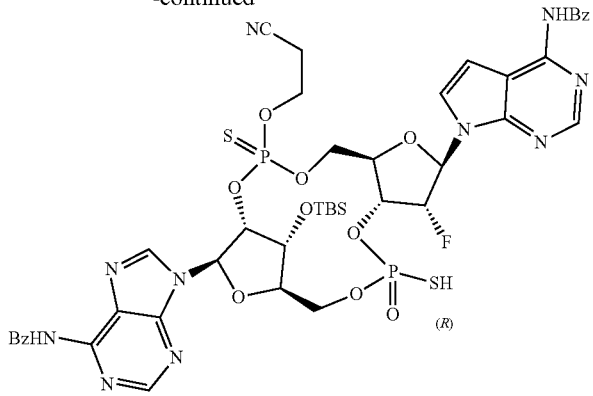

2-3

Compound 2-3

To a solution of compound 2-2 from the previous step (9.63 g, assume 9.15 mmol) in pyridine (200 mL) was added DMOCP (5.90 g, 32.0 mmol, 3.5 eq) and the mixture was stirred for 0.5 h at RT. 3H-1,2-Benzodithiol-3-one 1,1-dioxide (2.75 g, 13.7 mmol, 1.5 eq) was then added, and the resulting mixture and stirred at RT for further 30 minutes. The reaction mixture was quenched by addition of 3.4% aq. NaHCO$_3$ (1.0 L), and then extracted with EtOAc mL (2×500 mL). The combined organic layers were washed with brine (300 mL), dried over anhydrous Na$_2$SO$_4$, filtered and concentrated under reduced pressure. The residue was purified by SiO$_2$ gel chromatography (CH$_2$Cl$_2$/MeOH=30/1 to 10/1) to give compound 2-3 (3.2 g, 2.1 mmol) as a mixture of diastereoisomers which was used as such in the following step.

Step 4

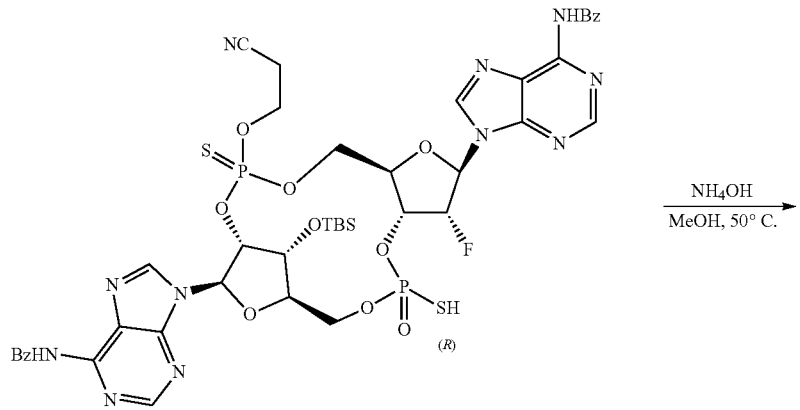

2-3

$\xrightarrow{\text{NH}_4\text{OH}}{\text{MeOH, 50° C.}}$

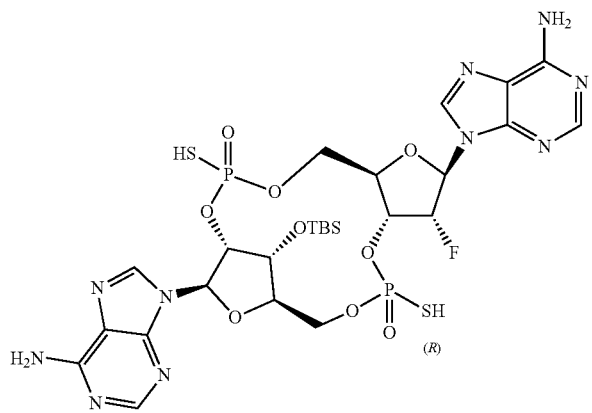

2-4

Compound 2-4

To a solution of compound 2-3 from the previous step (2.0 g, 1.87 mmol) in MeOH (10 mL) was added NH$_4$OH (18.2 g, 519 mmol, 277 eq). The mixture was stirred at 50° C. for 16 h in a pressure safe steel vessel, then concentrated under reduced pressure. The residue was purified by prep-HPLC [PHENOMENEX® LUNA® C18 250*50 10 um; mobile phase: A: H$_2$O (10 mM NH$_4$HCO$_3$); B: MeCN; A %-B %=10%-40%, 20 minutes] to give two products: compound 2-4a (R$_p$R$_p$ or S$_p$R$_p$ diastereoisomer, 180 mg, 0.209 mmol) and compound 2-4b (S$_p$R$_p$ or R$_p$R$_p$ diastereoisomer, 200 mg, 0.228 mmol) as white solids.

Step 5

The reaction mixture was then allowed to cool to RT and concentrated under reduced pressure. The residue was taken up in H$_2$O (0.5 mL), cooled to 10° C. and kept stirring for 30 minutes, then filtered and the filter cake was collected to give compound 2-5a (30.0 mg, 41.3 umol) as a white solid.

MS(ES$^+$) C$_{20}$H$_{24}$FN$_{10}$O$_9$P$_2$S$_2$ requires: 693, found: 693.2 [M+H]$^+$; $^1$H-NMR (400 MHz, CD$_3$OD) δ ppm 8.98 (s, 1H), 8.22 (s, 2H), 7.82 (s, 1H), 6.45 (d, J=14.4 Hz, 1H), 6.33 (d, J=8.0 Hz, 1H), 5.62 (d, J=53.8 Hz, 1H), 5.32 (m, 1H), 5.07-5.13 (m, 1H), 4.36-4.46 (m, 5H), 4.06 (d, J=11.2 Hz, 1H), 3.86-3.90 (m, 1H).

Reaction of compound 2-4b in a similar manner afforded compound 2-5b (30.0 mg, 41.3 umol) as a white solid.

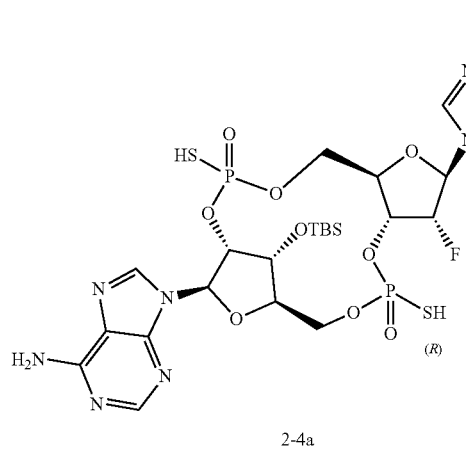

2-4a

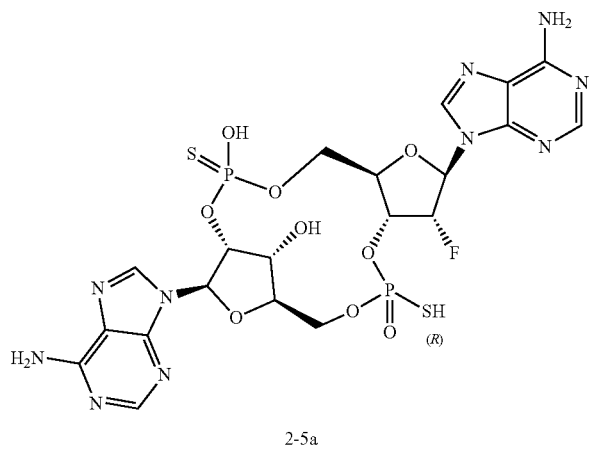

2-5a

Compound 2-5

To a solution of compound 2-4a (100 mg, 119 umol) in MeOH (3.0 mL) was added NH$_4$F (44.1 mg, 1.19 mmol, 10 eq) and the resulting mixture was stirred at 60° C. for 16 h.

MS(ES$^+$) C$_{20}$H$_{24}$FN$_{10}$O$_9$P$_2$S$_2$ requires: 693, found: 693.2 [M+H]$^+$; $^1$H-NMR (400 MHz, CD$_3$OD) δ ppm 8.76 (s, 1H), 8.49 (s, 1H), 8.24 (s, 1H), 8.18 (s, 1H), 6.34-6.41 (m, 2H), 5.70 (dd, J=51.8 Hz, 1H), 5.22-5.239 (m, 2H), 4.50-4.59 (m, 4H), 4.32 (s, 1H), 4.03-4.07 (m, 1H).

Step 6

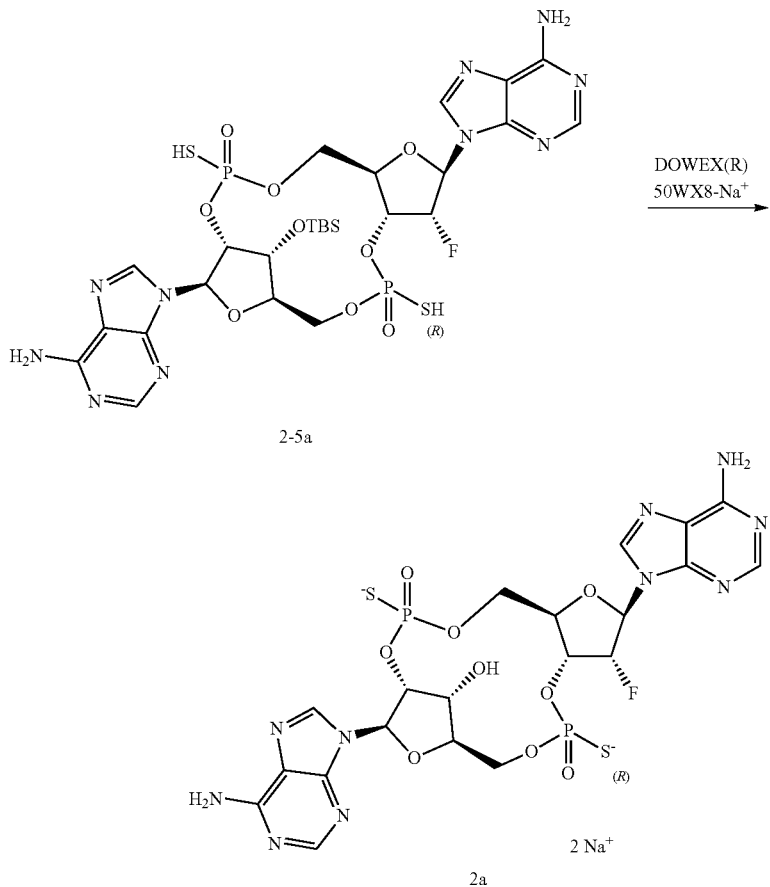

(1R,6R,8R,9R,10R,12R,15R,17R,18R)-8,17-di(6-amino-9H-purin-9-yl)-9-fluoro-18-hydroxy-3,12-dimercapto-2,4,7,11,13,16-hexaoxa-3λ⁵, 12λ⁵-diphosphatricyclo-[13.2.1.0⁶,¹⁰]octadecane-3,12-dione (2-5), disodium salt (Example 2a and Example 2b)

To a solution of compound 2-5a (30.0 mg, 41.3 umol) in H$_2$O (10.0 mL) was added Dowex®-50WX8 (Na⁺ form; 300 mg) and the mixture was stirred at RT for 4 h. The reaction was then filtered, and the filtrate was lyophilized to give Example 2a (R$_p$R$_p$ or S$_p$R$_p$; 30.0 mg, 40.6 umol) as a white solid.

MS(ES⁺) C$_{20}$H$_{24}$FN$_{10}$O$_9$P$_2$S$_2$ requires: 693, found: 693.0 [M+H]⁺; ¹H-NMR (400 MHz, DMSO-d$_6$) δ ppm 8.56 (s, 1H), 8.40 (s, 1H), 8.17 (s, 1H), 8.13 (s, 1H), 7.34 (s, 2H), 7.22 (s, 2H), 6.23 (m, 1H), 6.09 (d, J=8.4 Hz 1H), 5.71 (d, J=52.8 Hz, 1H), 5.54 (s, 1H), 5.15-5.30 (m, 2H), 3.91-4.37 (m, 5H), 3.67-3.70 (m, 1H); ³¹P NMR (162 MHz, CD$_3$OD) δ ppm 55.97, 53.66; R$_t$=1.384 minutes [Waters XBridge Shield RP18 2.1*50 mm, 5 um; mobile phase: A: H$_2$O+10 mM NH$_4$HCO$_3$; B: MeCN; A %-B %=0%-30%, 5.2 minutes].

Reaction of compound 2-5b in a similar manner gave Example 2b (S$_p$R$_p$ or R$_p$R$_p$, 28.0 mg, 40.6 umol) as a white solid.

MS(ES⁺) C$_{20}$H$_{24}$FN$_{10}$O$_9$P$_2$S$_2$ requires: 693, found: 693.0 [M+H]⁺; ¹H-NMR (400 MHz, CD$_3$OD) δ ppm 8.86 (br s, 1H), 8.39 (s, 1H), 8.19 (s, 1H), 8.02 (br s, 1H), 6.35-6.41 (m, 2H), 5.70 (d, J=51.8 Hz, 1H), 5.22-5.27 (m, 2H), 4.35-4.60 (m, 5H), 4.05-4.08 (m, 2H); ³¹P NMR (162 MHz, CD$_3$OD) δ ppm 57.39, 52.28; R$_t$=1.644 minutes [Waters XBridge Shield RP18 2.1*50 mm, 5 um; mobile phase: A: H$_2$O+10 mM NH$_4$HCO$_3$; B: MeCN; A %-B %=0%-30%, 5.2 minutes].

EXAMPLE 3a AND EXAMPLE 3b

Cyclic dinucleotides RR-CD-7dA-A and SR-CD-7dA-A dithio-[R$_p$, R$_p$]-cyclic-[7dA(2',5')p-A(3',5')p] dithio-[S$_p$, R$_p$]-cyclic-[7dA(2',5')p-A (3',5')p]

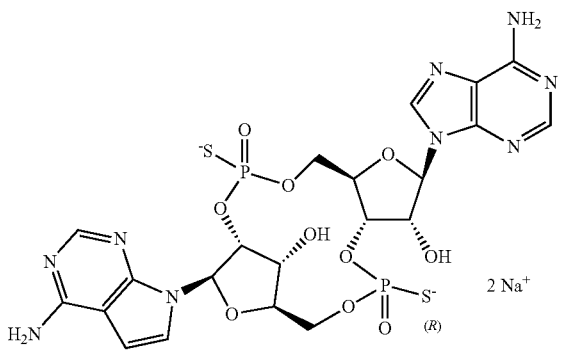

Example 3a: diastereoisomer R$_p$R$_p$ or S$_p$P$_p$
Example 3b: diastereoisomer S$_p$P$_p$ or R$_p$R$_p$

Step 1

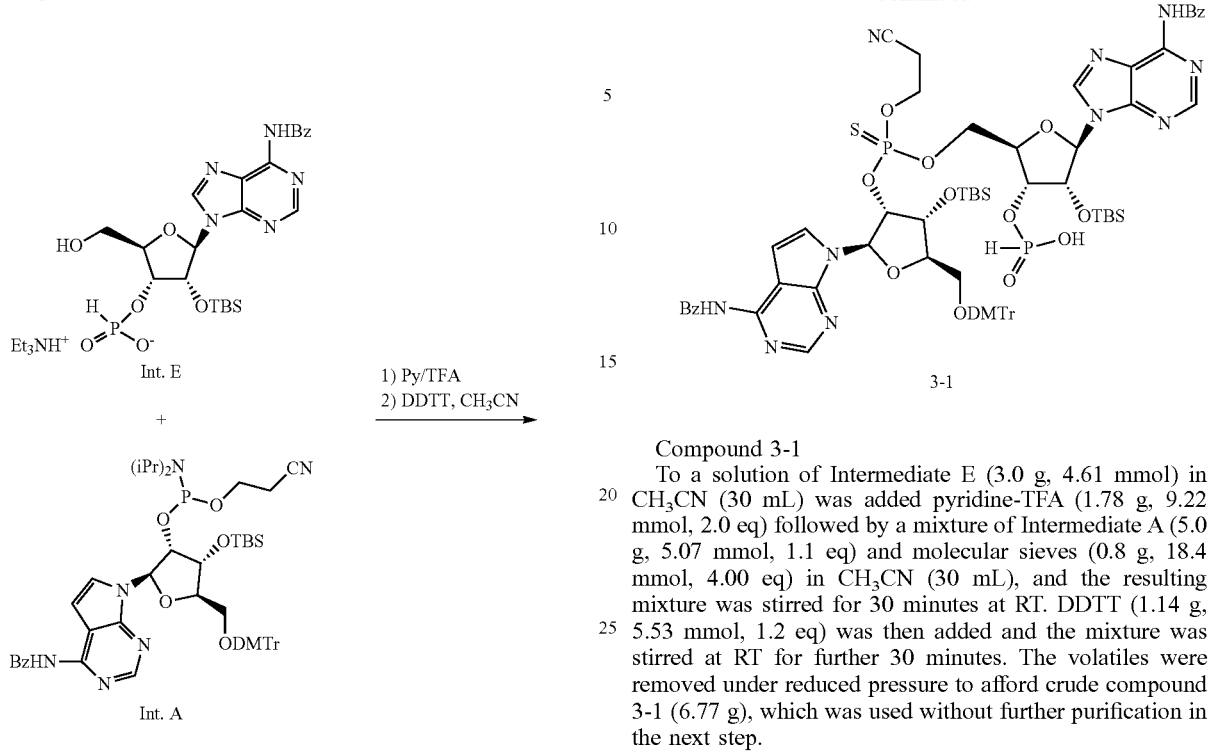

Compound 3-1

To a solution of Intermediate E (3.0 g, 4.61 mmol) in CH$_3$CN (30 mL) was added pyridine-TFA (1.78 g, 9.22 mmol, 2.0 eq) followed by a mixture of Intermediate A (5.0 g, 5.07 mmol, 1.1 eq) and molecular sieves (0.8 g, 18.4 mmol, 4.00 eq) in CH$_3$CN (30 mL), and the resulting mixture was stirred for 30 minutes at RT. DDTT (1.14 g, 5.53 mmol, 1.2 eq) was then added and the mixture was stirred at RT for further 30 minutes. The volatiles were removed under reduced pressure to afford crude compound 3-1 (6.77 g), which was used without further purification in the next step.

Step 2

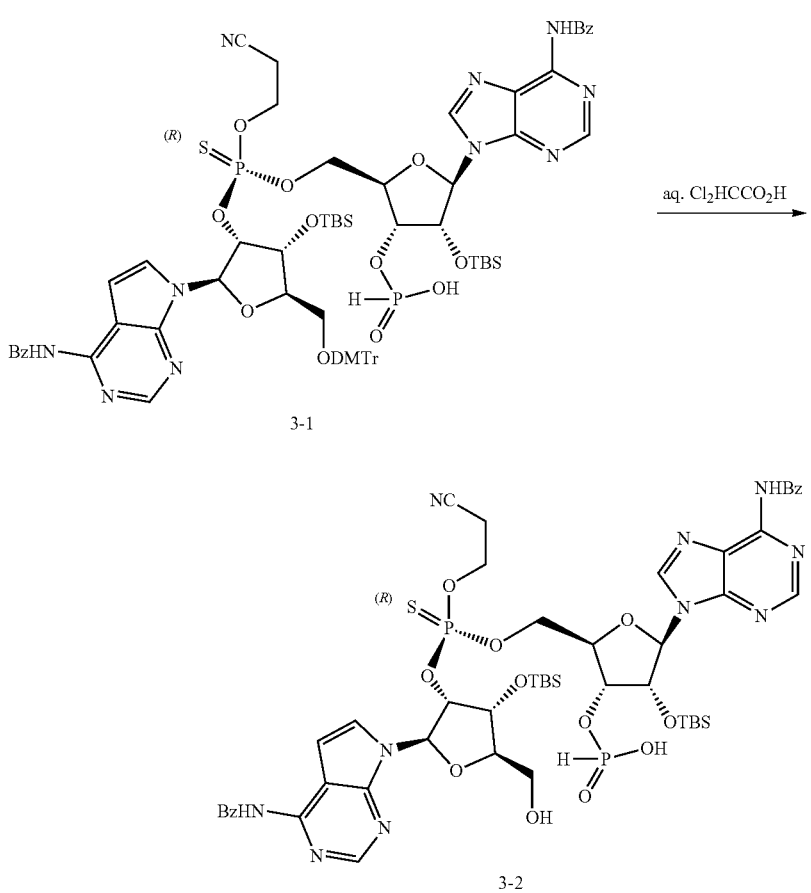

Compound 3-2

To a solution of Cl$_2$CHCOOH acid in CH$_2$Cl$_2$ (6% v/v, 100 mL) was added H$_2$O (83.1 mg, 4.61 mmol, 83.12 uL, 1.00 eq) and compound 3-1 from the previous step (6.77 g, assume 4.61 mmol, 1.00 eq). The reaction mixture was stirred at RT for 0.5 h, then quenched with pyridine (80 mL) and concentrated under reduced pressure to afford compound 3-2 (5.48 g), which was used without further purification in the next step.

Step 3

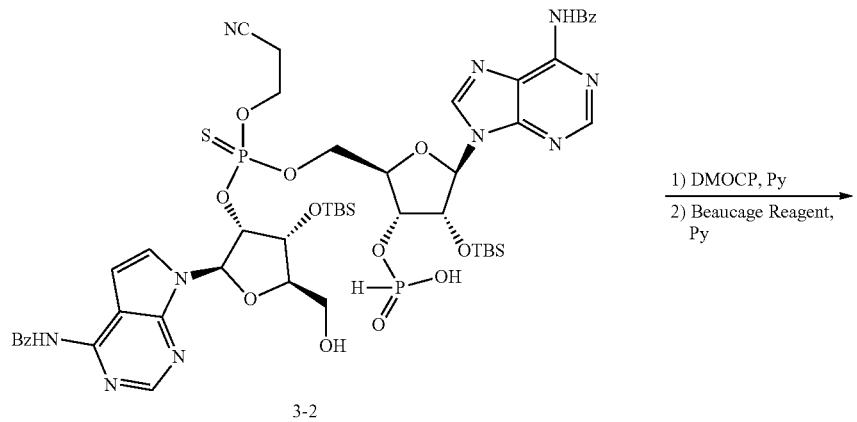

3-2 added DMOCP (4.77 g, 25.8 mmol, 5.5 eq) and the mixture was stirred for 0.5 h at RT. 3H-1,2-Benzodithiol-3-one 1,1-dioxide (1.41 g, 7.05 mmol, 1.5 eq) was then added, and the resulting mixture and stirred at RT for further 30 minutes. The reaction mixture was quenched by addition of 3.4% aq. NaHCO$_3$ (600 mL), and then extracted with EtOAc (2×300 mL). The combined organic layers were washed with brine (200 mL), dried over anhydrous Na$_2$SO$_4$, filtered and concentrated under reduced pressure. The residue was purified by SiO$_2$ gel chromatography (CH$_2$Cl$_2$/MeOH=30/1

1) DMOCP, Py
2) Beaucage Reagent, Py

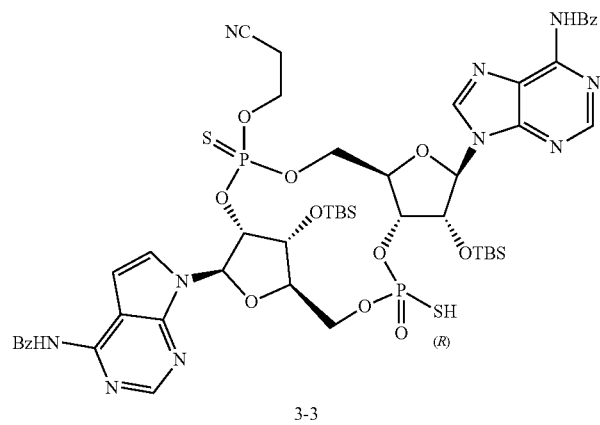

3-3

Compound 3-3

To a solution of compound 3-2 from the previous step (5.48 g, assume 4.61 mmols) in pyridine (150 mL) was to 15/1) to give compound 3-3 (3.0 g, 1.53 mmol) as a mixture of diastereoisomers which was used as such in the following step.

Step 4

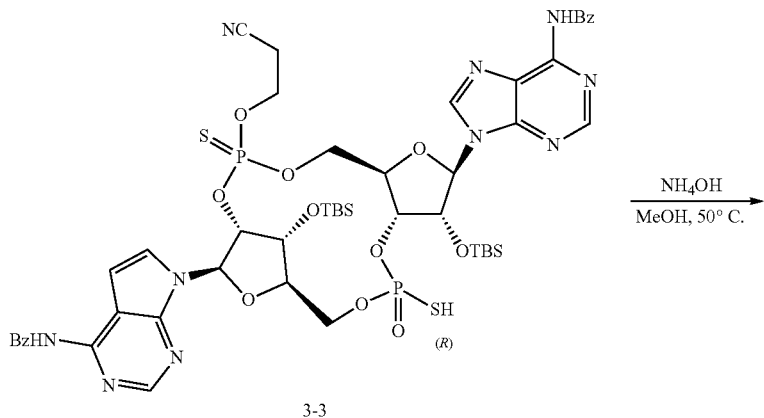

Compound 3-4

To a solution of compound 3-3 from the previous step (3.0 g, 1.53 mmol) in MeOH (30 mL) was added NH₄OH (16.4 g, 468 mmol, 307 eq). The mixture was stirred at 50° C. for 16 h in a pressure safe steel vessel, then concentrated under reduced pressure. The residue was purified by prep-HPLC [PHENOMENEX® LUNA® C18 250*50 10 um; mobile phase: A: H₂O (10 mM NH₄HCO₃); B: MeCN; A %-B %=20%-45%, 20 minutes] to give compound 3-4a ($R_pR_p$ or $S_pR_p$ diastereoisomer, 220 mg, 208 umol) and compound 3-4b ($S_pR_p$ or $R_pR_p$ diastereoisomer, 220 mg, 208 umol) as white solids.

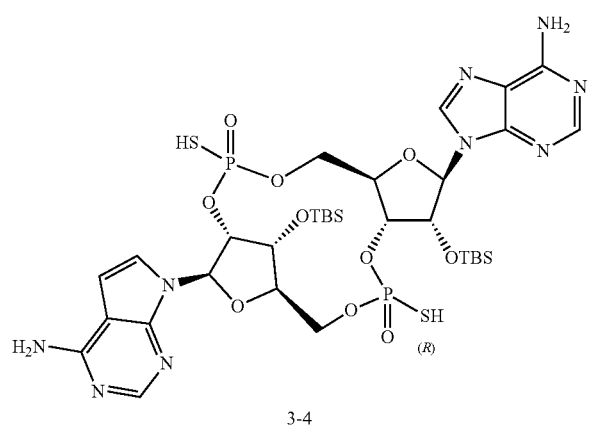

Step 5

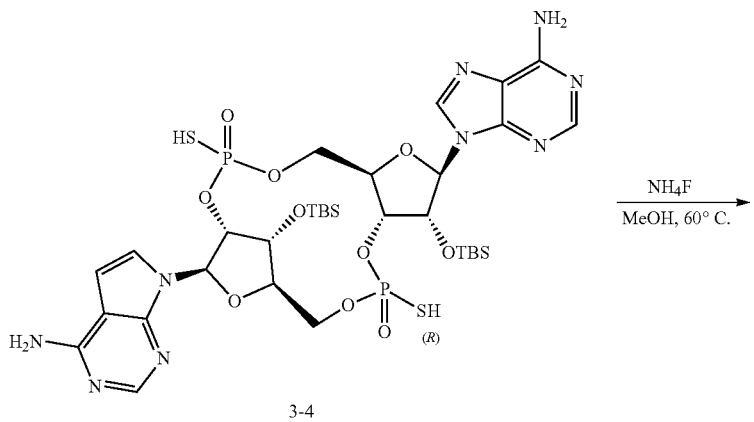

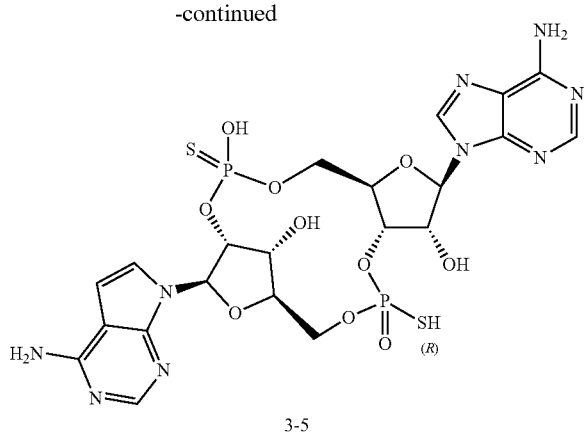

3-5

Compound 3-5

To a solution of compound 3-4a (100 mg, 105 umol) in MeOH (3.0 mL) was added NH$_4$F (38.9 mg, 1.05 mmol, 10 eq) and the resulting mixture was stirred at 60° C. for 12 h. The reaction mixture was then allowed to reach RT and concentrated under reduced pressure. The residue was taken up in H$_2$O (1 mL) at 40° C., cooled to 5° C. and kept stirring for 30 minutes, then filtered and the filter cake was collected to give compound 3-5a (20.0 mg, 26.3 umol,) as a white solid.

Reaction of compound 3-4b in a similar manner afforded compound 3-5b (33.0 mg, 45.6 umol) as a white solid.

Step 6

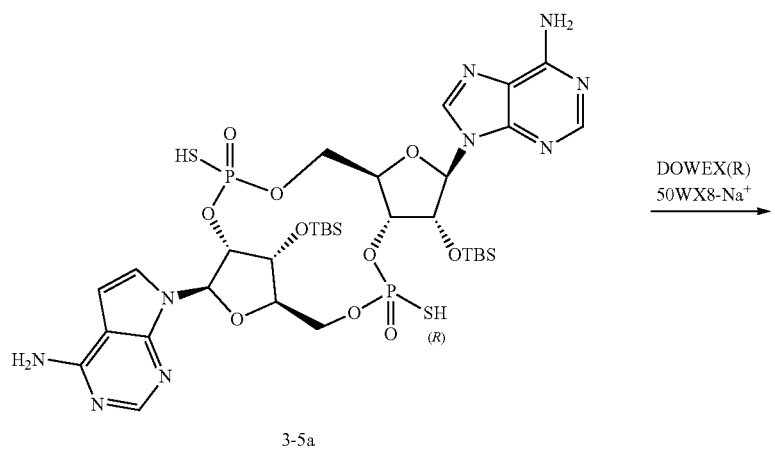

3-5a

DOWEX(R) 50WX8-Na$^+$

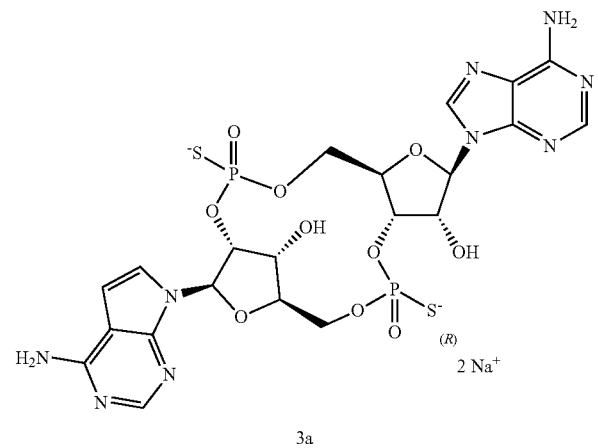

3a (1R,6R,8R,9R,10R,12R,15R,17R,18R)-17-(4-amino-7H-pyrrolo[2,3-d]pyrimidin-7-yl)-8-(6-amino-9H-purin-9-yl)-9,18-dihydroxy-3,12-dimercapto-2,4,7,11,13,16-hexaoxa-3$\lambda^5$,12$\lambda^5$-diphosphatricyclo[13.2.1.0$^{6,10}$]octadecane-3,12-dione, disodium salt (Example 3a and Example 3b)

To a solution of compound 3-5a (20.0 mg, 27.6 umol) in H$_2$O (5 mL) was added DOWEX® 50WX8 (Na$^+$ form; 300 mg) and the mixture was stirred at RT for 3 h. The reaction was then filtered, and the filtrate was lyophilized to give Example 3a as a white solid (R$_p$R$_p$ or S$_p$R$_p$, 18.0 mg, 24.5 umol).

MS(ES$^+$) C$_{21}$H$_{26}$N$_9$O$_{10}$P$_2$S$_2$ requires: 690, found: 690.0 [M+H]$^+$; $^1$H-NMR (400 MHz, CD$_3$OD) δ ppm 8.33 (s, 1H), 8.20 (s, 1H), 8.05 (s, 1H), 7.84 (d, J=4.0 Hz 1H), 6.62 (d, J=3.6 Hz, 1H), 6.51 (d, J=8.4 Hz, 1H), 6.12 (d, J=6.8 Hz, 1H), 5.59-5.60 (m, 1H), 5.35-5.59 (m, 1H), 5.21-5.24 (m, 1H), 4.25-4.45 (m, 4H), 3.99 (d, J=12.0 Hz, 1H), 3.90-3.92 (m, 1H); $^{31}$P NMR (162 MHz, CD$_3$OD) δ ppm 60.36, 60.28; R$_t$=1.497 minutes [Waters XBridge Shield RP18 2.1*50 mm, 5 um; mobile phase: A: H$_2$O+10 mM NH$_4$HCO$_3$; B: MeCN; A %-B %=0%-30%, 5.2 minutes].

Reaction of compound 3-5b in a similar manner gave Example 3b (S$_p$R$_p$ or R$_p$R$_p$, 33.0 mg, 44.9 umol) as a white solid.

MS(ES$^+$) C$_{21}$H$_{26}$N$_9$O$_{10}$P$_2$S$_2$ requires: 690, found: 690.0 [M+H]$^+$; $^1$H-NMR (400 MHz, CD$_3$OD) δ ppm 8.34 (s, 1H), 8.21 (s, 1H), 8.07 (s, 1H), 7.97 (d, J=3.6 Hz 1H), 6.72 (d, J=4 Hz, 1H), 6.56 (d, J=8.0 Hz, 1H), 6.12 (d, J=3.2 Hz, 1H), 5.20-5.31 (m, 2H), 4.98-5.01 (m, 1H), 4.71 (d, J=4 Hz, 1H), 4.33-4.49 (m, 1H), 4.25-4.30 (m, 3H), 4.07-4.12 (m, 1H); $^{31}$P NMR (162 MHz, CD$_3$OD) δ ppm 57.30, 53.90; R$_t$=1.647 minutes [Waters XBridge Shield RP18 2.1*50 mm, 5 um; mobile phase: A: H$_2$O+10 mM NH$_4$HCO$_3$; B: MeCN; A %-B %=0%-30%, 5.2 minutes].

EXAMPLE 4a, 4b, 4c AND 4b

Cyclic dinucleotides RR-CD-A-2'Cl-A, RS-CD-A-2'Cl-A, SS-CD-A-2'Cl-A, and SR-CD-A-2' Cl-A; dithio-[R$_p$, R$_p$]-cyclic-[A(2',5')p-2'Cl-A(3',5')p], dithio-[R$_p$, S$_p$]-cyclic-[A(2',5')p-2'Cl-A(3',5')p], dithio-[S$_p$, S$_p$]-cyclic-[A(2',5')p-2'Cl-A(3',5')p]dithio-[S$_p$, R$_p$]-cyclic-[A(2',5')p-2'Cl-A (3',5')p]

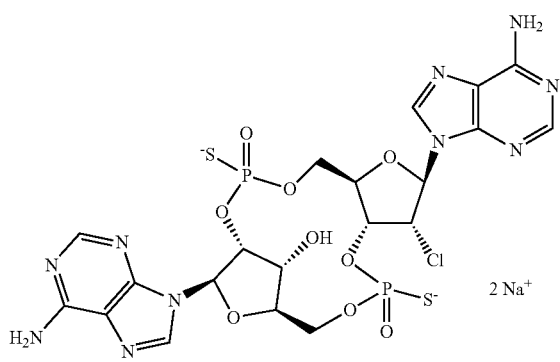

Example 4a, Example 4b, Example 4c, Example 4d

Step 1

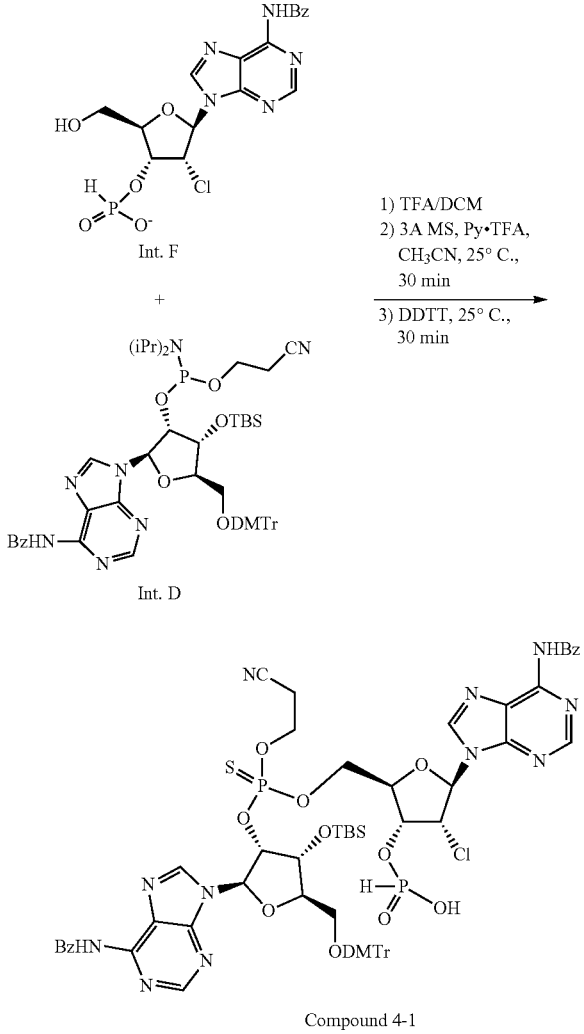

Compound 4-1.

To a solution of Int F (3.00 g, 6.61 mmol, 1.0 eq) in DCM (60 mL) was added TEA (0.334 g, 3.31 mmol, 0.46 uL, 0.5 eq). The volatiles were removed under reduced pressure, pyridine-TFA (2.55 g, 13.2 mmol, 2.0 eq) was added to the residue, and the mixture was co-evaporated three times with anhydrous CH$_3$CN (40 mL). The residue was dissolved in anhydrous CH$_3$CN (30 mL) and stirred with 3 Å molecular sieves (3.00 g, 6.61 mmol, 1.0 eq) for five minutes. In a separate vessel Int D (6.53 g, 6.61 mmol, 1.0 eq) was co-evaporated three times with anhydrous CH$_3$CN (20 mL), then dissolved in anhydrous CH$_3$CN (30 mL). The resulting solution of Int D was added to the mixture of Int F, pyridine-TFA and 3 Å molecular sieves, followed by DDTT (1.63 g, 7.93 mmol, 1.2 eq), and the resulting mixture was stirred at 25° C. for 30 min. The mixture was then concentrated under reduced pressure to give Compound 4-1 (9.0 g) as a yellow solid which was used for the next step without further purification.

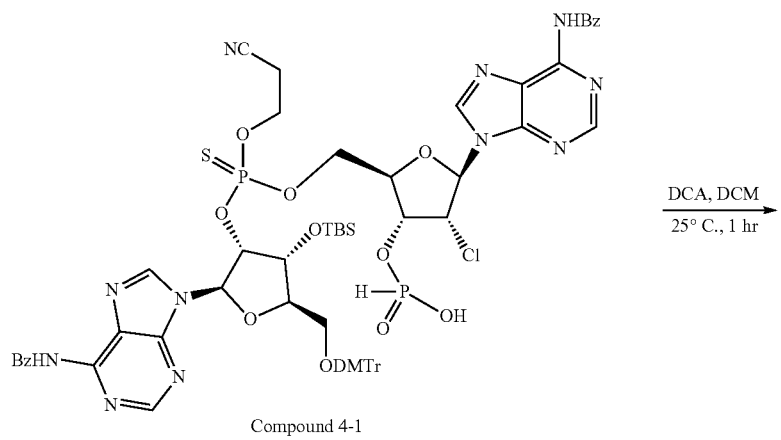

Compound 4-1

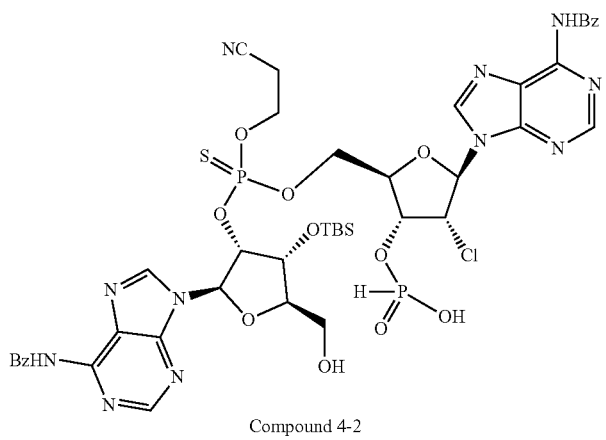

Compound 4-2

Step 2

Compound 4-2.

To a solution of Compound 4-1 (9.0 g, 6.56 mmol, 1.0 eq) in DCM (90 mL) was added Cl$_2$CHCOOH acid (2.7 mL). The mixture was stirred at 25° C. for 1 hr, and triethylsilane (4.57 g, 39.3 mmol, 6.28 mL, 6.0 eq) was added followed by pyridine (45.0 mL). The resulting mixture was stirred at RT for 30 minutes, then concentrated under reduced pressure. The residue was purified by SiO$_2$ gel chromatography (DCM:MeOH=10:1 to 3:1) to give Compound 4-2 (2.12 g, 1.98 mmol, 30% yield) as a light yellow solid. MS(ES$^+$) C$_{43}$H$_{50}$ClN$_{11}$O$_{12}$P$_2$SSi requires: 1069, found: 1070 [M+H]$^+$.

Step 3

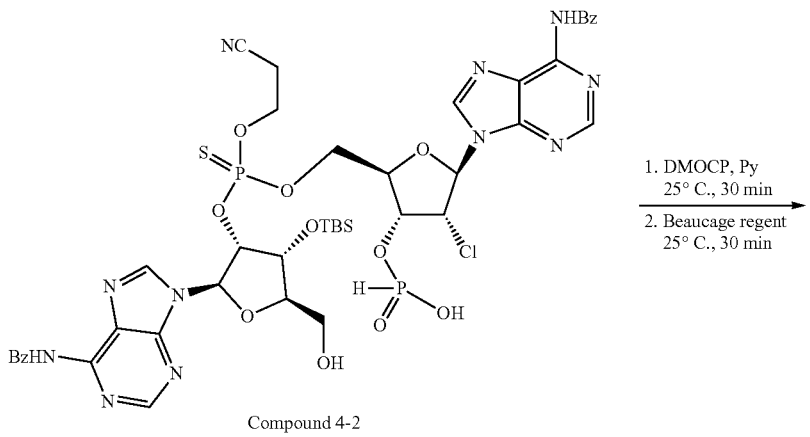

Compound 4-2

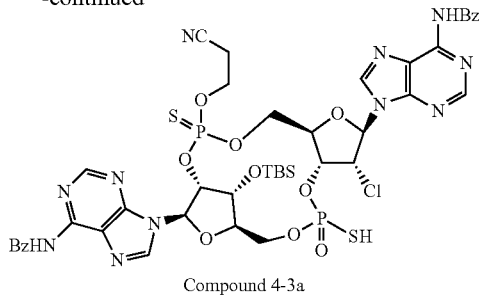
Compound 4-3a

+

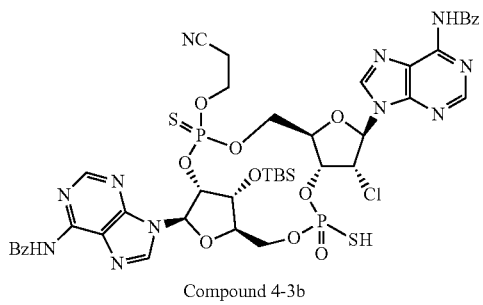
Compound 4-3b

Compound 4-3a and Compound 4-3b.

Compound 4-2 (2.12 g, 1.98 mmol, 1.0 eq) was co-evaporated three times with anhydrous Pyridine (40.0 mL), dissolved in anhydrous Pyridine (40.0 mL) and the solution was cooled to 0° C. DMOCP (1.28 g, 6.93 mmol, 3.5 eq) was added, and the mixture was stirred for 0.5 h at RT. 3H-1,2-Benzodithiol-3-one 1,1-dioxide (0.595 g, 2.97 mmol, 1.5 eq) was then added, and the resulting mixture and stirred at RT for further 30 minutes. The reaction mixture was quenched by addition of 3.4% aq. $NaHCO_3$ (600 mL), and then extracted with EtOAc (2×300 mL). The combined organic layers were washed with brine (200 mL), dried over anhydrous $Na_2SO_4$, filtered and concentrated under reduced pressure. The residue was purified by $SiO_2$ gel chromatography ($CH_2Cl_2$/MeOH=30/1 to 10/1) to give compound 4-3a (0.470 g, 0.348 mmol, 17% yield) and compound 4-3b (0.380 g, 0.28 mmol, 14% yield), each one as a mixture of diastereoisomers of undefined stereochemistry at the phosphorothioate centers.

Step 4

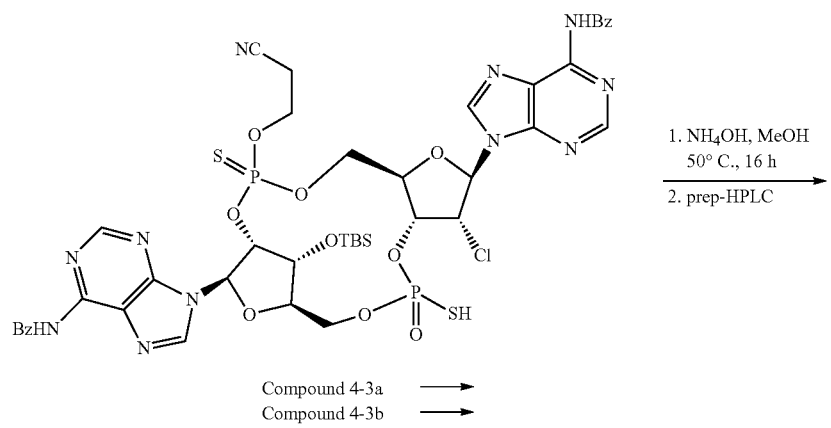

Compound 4-3a ⟶
Compound 4-3b ⟶

1. $NH_4OH$, MeOH 50° C., 16 h
2. prep-HPLC

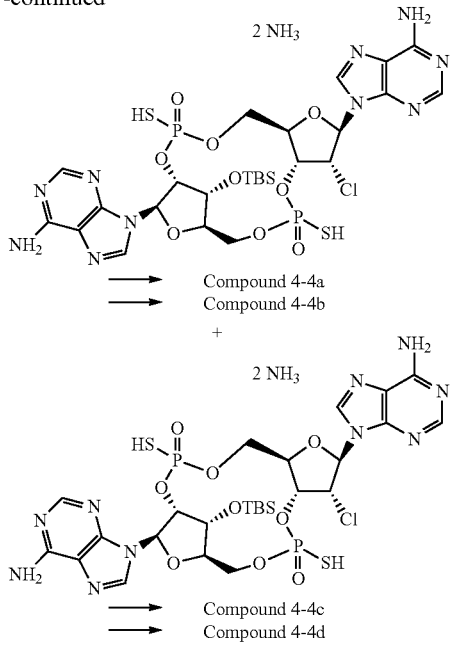

Compound 4-4a
Compound 4-4b

+

Compound 4-4c
Compound 4-4d

Compound 4-4a, 4-4b, 4-4c, 4-4d.

To a solution of Compound 4-3a (0.47 g, 0.43 mmol, 1.0 eq) in MeOH (3 mL) was added $NH_4OH$ (4.2 g, 519 mmol, 277 eq). The mixture was stirred at 50° C. for 16 h in a pressure safe steel vessel, then cooled to RT and concentrated under reduced pressure. The residue was purified by prep-HPLC [Agela Durashell® C18 150×25 5 um; mobile phase: A: $H_2O$ (10 mM $NH_4HCO_3$); B: MeCN; A %-B %=10%-40%, 10.5 minutes] to give two stereoisomer products of undefined stereochemistry at the phosphorothioate centers; compound 4-4a (93.0 mg, 0.11 mmol, 25% yield) and compound 4-4c (105 mg, 0.13 mmol, 29% yield), both as white solids.

Compound 4-3b (0.380 g, 0.28 mmol) was reacted in the same manner to give compounds 4-4b (82.0 mg, 99.6 umol, 28% yield) and 4-4d (82.0 mg, 99.6 umol, 28% yield) as two stereoisomers of undefined stereochemistry at the phosphorothioate centers, both as white solids.

Step 5

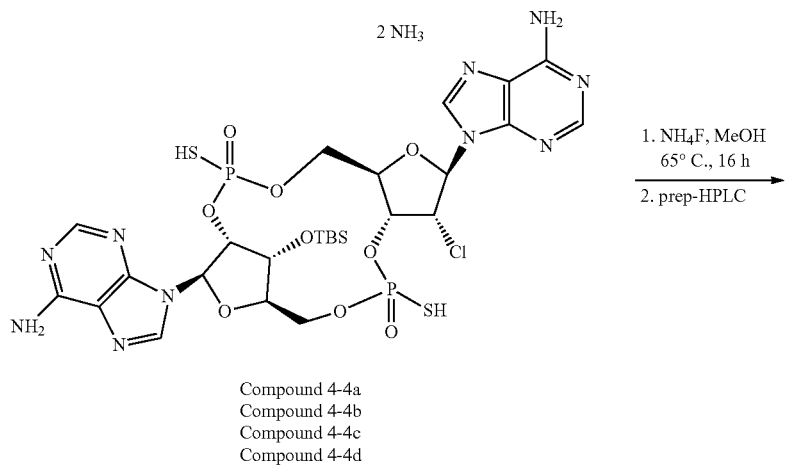

Compound 4-4a
Compound 4-4b
Compound 4-4c
Compound 4-4d

1. $NH_4F$, MeOH 65° C., 16 h
2. prep-HPLC

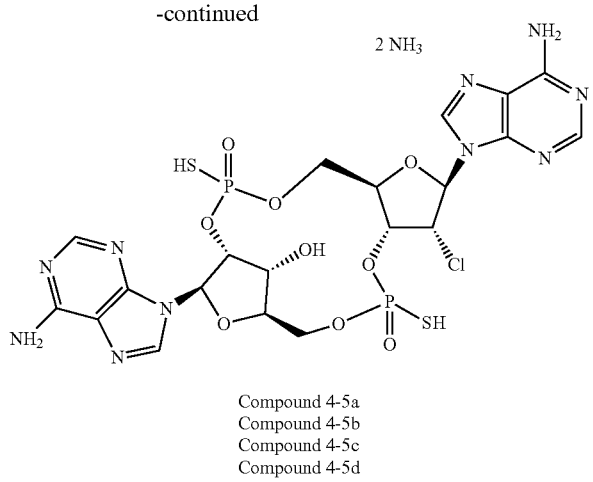

Compound 4-5a
Compound 4-5b
Compound 4-5c
Compound 4-5d

Compound 4-5a, 4-5b, 4-5c, 4-5d.

To a solution of compound 4-4a (93.0 mg, 0.11 mmol, 1.0 eq) in MeOH (3.0 mL) was added NH$_4$F (80 mg, 2.17 mmol, 20.0 eq) and the resulting mixture was stirred at 65° C. for 16 h. The reaction mixture was then allowed to cool to RT and concentrated under reduced pressure. The residue was purified by prep-HPLC [Agela Durashell® C18 150×25 5 um; mobile phase: A: H$_2$O (10 mM NH$_4$HCO$_3$); B: MeCN; A %-B %=10%-40%, 10.5 minutes] to give compound 4-5a (50.0 mg, 65.1 umol, 60% yield) as a white solid; Compounds 4-4b, 4-4c and 4-4d were reacted in the same manner to give the following compounds: 4-5b (40.0 mg, 56.4 umol, 56% yield); 4-5c (58.0 mg, 78.1 umol, 64% yield); and 4-5d (20.0 mg, 22.6 umol, 23% yield).

Step 6

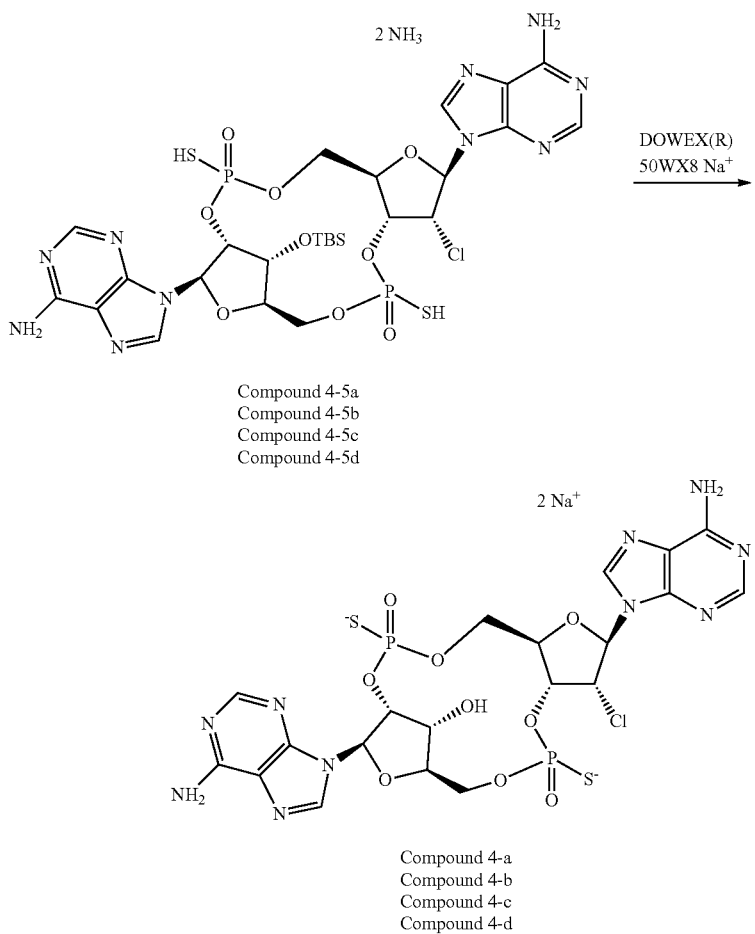

Compound 4-5a
Compound 4-5b
Compound 4-5c
Compound 4-5d

Compound 4-a
Compound 4-b
Compound 4-c
Compound 4-d

EXAMPLE 4a, 4b, 4c AND 4d

To a solution of compound 4-5a (50.0 mg, 67.3 umol, 1.0 eq) in H$_2$O (20.0 mL) was added Dowex®-50WX8 (Na$^+$ form; 500 mg) and the mixture was stirred at RT for 4 h. The reaction was then filtered, and the filtrate was lyophilized to give Example 4a (36.5 mg, 46.6 umol, 69% yield) as a white solid; single stereoisomer, undefined stereochemistry at the phosphorothioate centers; MS(ES$^+$) C$_{20}$H$_{23}$ClN$_{10}$O$_9$P$_2$S$_2$ requires: 708, found: 709 [M+H]$^+$; $^1$H-NMR (400 MHz D$_2$O) δ ppm 8.68 (s, 1H), 8.13 (s, 1H), 8.07 (s, 1H), 8.01 (s, 1H), 6.28 (d, J=2.0 Hz, 1H), 6.17 (d, J=8.4 Hz, 1H), 5.29-5.40 (m, 2H), 5.18-5.26 (m, 1H), 4.62 (d, J=4.0 Hz, 1H), 4.57 (br s, 1H), 4.42-4.51 (m, 2H), 4.14-4.25 (m, 2H), 4.09 (br d, J=12.8 Hz, 1H); $^{31}$P NMR (162 MHz, D$_2$O) δ ppm 55.69, 54.83; R$_t$=1.64 minutes [Waters XBridge Shield RP18 2.1*50 mm, 5 um; mobile phase: A: H$_2$O+10 mM NH$_4$HCO$_3$; B: MeCN; A %-B %=0%-30%, 5.2 minutes].

Compounds 4-5b, 4-5c and 4-5d were reacted in the same manner to give the following compounds, all as single stereoisomers, with undefined stereochemistry at the phosphorothioate centers:

Example 4b (40.0 mg, 48.2 umol, 89.6% yield); MS(ES$^+$) C$_{20}$H$_{23}$ClN$_{10}$O$_9$P$_2$S$_2$ requires: 708, found: 709 [M+H]$^+$; $^1$H-NMR (400 MHz D$_2$O) δ ppm 8.42 (s, 1H), 8.16 (s, 1H), 8.04 (s, 1H), 7.94 (s, 1H), 6.26 (d, J=3.1 Hz, 1H), 6.20 (d, J=8.3 Hz, 1H), 5.33-5.43 (m, 2H), 5.09-5.13 (m, 1H), 4.55-4.61 (m, 2H), 4.42-4.49 (m, 3H), 4.34-4.41 (m, 1H), 4.05-4.14 (m, 2H); $^{31}$P NMR (162 MHz, D$_2$O) δ ppm 56.58, 54.75; R$_t$=1.74 minutes [Waters XBridge Shield RP18 2.1*50 mm, 5 um; mobile phase: A: H$_2$O+10 mM NH$_4$HCO$_3$; B: MeCN; A %-B %=0%-30%, 5.2 minutes].

Example 4c (35.2 mg, 46.6 umol, 59.7% yield), MS(ES$^+$) C$_{20}$H$_{23}$ClN$_{10}$O$_9$P$_2$S$_2$ requires: 708, found: 709 [M+H]$^+$; $^1$H-NMR (400 MHz D$_2$O) δ ppm 8.65 (s, 1H), 8.19 (s, 1H), 8.08 (s, 1H), 8.05 (s, 1H), 6.37 (s, 1H), 6.17 (d, J=8.3 Hz, 1H), 5.42 (d, J=4.8 Hz, 1H), 5.33 (m, 1H), 5.08-5.16 (m, 1H), 4.93 (d, J=3.9 Hz, 1H), 4.62 (br d, J=9.0 Hz, 1H), 4.44-4.51 (m, 2H), 4.27 (m, 1H), 4.18 (br s, 2H); $^{31}$P NMR (162 MHz, D$_2$O) δ ppm 53.99, 51.92; R$_t$=2.09 minutes [Waters XBridge Shield RP18 2.1*50 mm, 5 um; mobile phase: A: H$_2$O+10 mM NH$_4$HCO$_3$; B: MeCN; A %-B %=0%-30%, 5.2 minutes].

Example 4d (17.0 mg, 24.0 umol, 89.1% yield) C$_{20}$H$_{23}$ClN$_{10}$O$_9$P$_2$S$_2$ requires: 708, found: 709 [M+H]$^+$; $^1$H-NMR (400 MHz D$_2$O) δ ppm 8.34 (s, 1H), 8.10 (s, 1H), 8.04 (s, 1H), 7.86 (s, 1H), 6.30 (s, 1H), 6.14 (d, J=8.4 Hz, 1H), 5.36 (m, 1H), 5.24 (m, 1H), 5.05 (d, J=4.4 Hz, 1H), 4.80 (d, J=4.0 Hz, 1H), 4.55 (br d, J=8.0 Hz, 1H), 4.36-4.44 (m, 2H), 4.32 (ddd, J=12.0, 6.4, 2.0 Hz, 1H), 4.20 (m, 1H), 4.02 (dd, J=11.2, 3.6 Hz, 1H); $^{31}$P NMR (162 MHz, D$_2$O) δ ppm 54.64, 52.01; R$_t$=2.03 minutes [Waters XBridge Shield RP18 2.1*50 mm, 5 um; mobile phase: A: H$_2$O+10 mM NH$_4$HCO$_3$; B: MeCN; A %-B %=0%-30%, 5.2 minutes].

The following compounds, or a salt, ester, prodrug, or tautomer thereof, can generally be made using the methods described above. It is expected that these compounds when made will have activity similar to those that have been prepared.

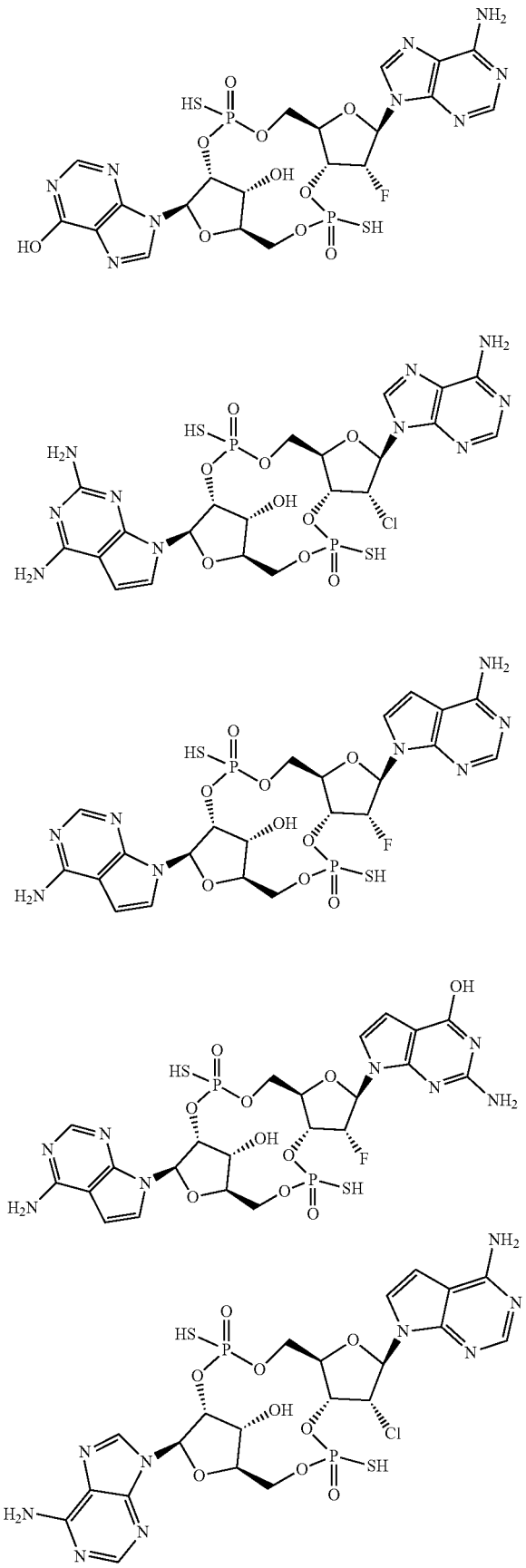

-continued

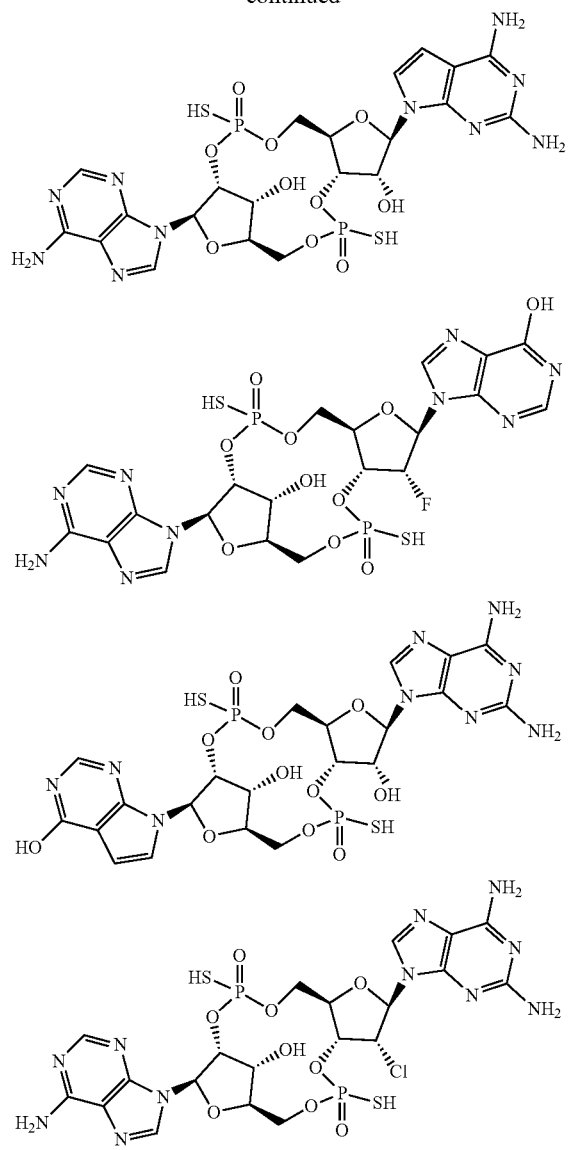

Biological Activity Assays

THP-1 Dual Assay

The INVIVOGEN® THP-1 Dual™ assay (catalog code: thpd-nfis) was used to evaluate the listed compounds as agonist of the STING receptor. The THP-1 Dual™ cells are derived from the human monocytic cell line THP-1 by stable integration of two inducible reporter constructs. This assay enables simultaneous study of the two main signaling pathways for STING: (a) the NF-κB pathway, by monitoring the activity of secreted embryonic alkaline phosphatase (SEAP); and (b) the Interferon regulatory factor (IRF) pathway, by assessing the activity of a secreted luciferase (Lucia™).

The procedure as set forth by the manufacturer was followed, with the following modifications: (1) plates are incubated 18 h after addition of cell suspension, and (2) the optional differentiation step is not employed.

Tables 1 and 2. Biological Activity

TABLE 1

Fold induction of IRF3 activation in THP-1 Dual ™ cells upon treatment with increasing concentrations of STING agonist.

|  | 0.1 mg/mL | 0.5 mg/mL | 1 mg/mL | 5 mg/mL | 10 mg/mL |
|---|---|---|---|---|---|
| 3',5'-c-di-GMP | 1.07 | 1.26 | 1.32 | 2.87 | 5.93 |
| ML-RS-CDA* | 1.31 | 11.55 | 56.72 | 144.86 | 141.76 |
| ML-RR-CDA** | 2.65 | 4.57 | 8.91 | 148.89 | 166.88 |
| Example 1a | 1.14 | 1.84 | 9.77 | 112.64 | 157.93 |
| Example 1b | 0.99 | 1.88 | 3.52 | 25.91 | 87.63 |
| Example 2a | 27.89 | 138.29 | 148.06 | 147.12 | 143.02 |
| Example 2b | 16.46 | 95.25 | 156.38 | 159.53 | 157.10 |
| Example 3a | 1.41 | 0.98 | 2.07 | 3.04 | 4.29 |
| Example 3b | 1.38 | 1.48 | 1.56 | 5.05 | 6.70 |
| Example 4d | 1.99 | nd | 5.89 | nd | 22.37 |

*= dithio-[$R_p,S_p$]-cyclic-[A(2',5')p-A(3',5')p];
**= dithio-[$R_p,R_p$]-cyclic-[A(2',5')p-A(3',5')p]; prep'd as in WO 2014/189805. Examples 4a-4c did not show significant activity.

TABLE 2

Fold induction of NF-κB activation THP-1 Dual ™ cells upon treatment with increasing concentrations of STING agonist.

|  | 0.1 mg/mL | 0.5 mg/mL | 1 mg/mL | 5 mg/mL | 10 mg/mL |
|---|---|---|---|---|---|
| 3',5'-c-di-GMP | 0.99 | 0.98 | 0.97 | 1.02 | 1.10 |
| ML-RS-CDA* | 0.99 | 1.05 | 1.42 | 17.03 | 20.05 |
| ML-RR-CDA** | 1.02 | 1.09 | 1.17 | 9.06 | 16.89 |
| Example 1a | 1.02 | 1.04 | 1.07 | 2.77 | 7.30 |
| Example 1b | 0.97 | 0.99 | 1.01 | 1.29 | 3.71 |
| Example 2a | 1.14 | 5.73 | 11.47 | 12.81 | 11.52 |
| Example 2b | 1.09 | 1.70 | 4.26 | 13.22 | 13.68 |
| Example 3a | 0.99 | 0.96 | 0.99 | 1.01 | 1.04 |
| Example 3b | 0.98 | 0.99 | 1.00 | 1.08 | 1.14 |
| Example 4d | 0.21 | nd | 0.24 | nd | 0.36 |

*= dithio-[$R_p,S_p$]-cyclic-[A(2',5')p-A(3',5')p];
**= dithio-[$R_p,R_p$]-cyclic-[A(2',5')p-A(3',5')p]; prep'd as in WO 2014/189805.
Examples 4a-4c did not show significant activity.

Mouse Ductal Pancreatic Cancer Assay

The procedure of Boj et al. (Cell 2015, 160, 324-338) was followed, which employs murine organoids. $2.5 \times 10^5$ MT4-2D cells were injected subcutaneously on the right flank of male 6 week old C57BL/6J mice. 5 ug of the indicated STING agonist was injected intra-tumorally on day 15 in a volume of 50 ul.

TABLE 3

In Vivo Activity

| Days Post Challenge | ML-RR-CDA (Tumor Vol, mm³) | Example 2a (Tumor Vol, mm³) | Example 2b (Tumor Vol, mm³) |
|---|---|---|---|
| 0 | 0.0 | 0.0 | 0.0 |
| 4 | 19.0 | 29.2 | 28.4 |
| 6 | 56.3 | 64.3 | 53.9 |
| 8 | 81.9 | 84.3 | 66.5 |
| 10 | 84.5 | 103.3 | 87.4 |
| 12 | 107.3 | 125.9 | 98.3 |
| 14 | 110.9 | 113.8 | 106.6 |
| 15 | 125.6 | 132.1 | 114.7 |
| 16 | 193.2 | 134.0 | 130.8 |
| 17 | 131.1 | 122.7 | 128.3 |
| 18 | 117.0 | 82.8 | 90.4 |
| 20 | 141.9 | 72.8 | 115.3 |
| 22 | 147.2 | 91.6 | 64.9 |
| 25 | 154.0 | 124.0 | 70.4 |

TABLE 3-continued

| | In Vivo Activity | | |
|---|---|---|---|
| Days Post Challenge | ML-RR-CDA (Tumor Vol, mm³) | Example 2a (Tumor Vol, mm³) | Example 2b (Tumor Vol, mm³) |
| 27 | 241.4 | 142.0 | 80.7 |
| 29 | 198.5 | 163.1 | 99.6 |
| 32 | 250.1 | 217.7 | 102.6 |

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of structural Formula I:

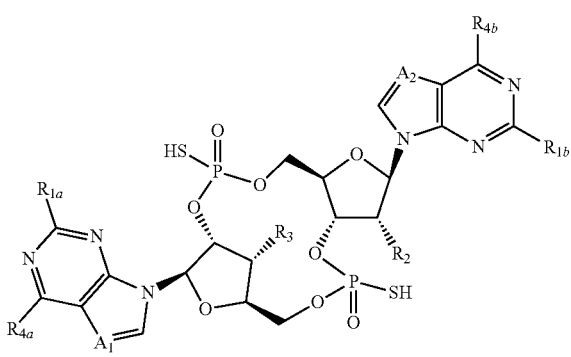

(I)

or a salt, ester, tautomer, or prodrug thereof, wherein:
$A_1$ is CH and $A_2$ is N, or $A_1$ is N and $A_2$ is CH, or $A_1$ is CH and $A_2$ is CH;
$R_{1a}$ and $R_{1b}$ are independently selected from H and $NH_2$;
$R_2$ is selected from OH, F, Cl, $N_3$, and $NH_2$;
$R_3$ is selected from OH, F, Cl, $N_3$, and $NH_2$;
$R_{4a}$ and $R_{4b}$ are independently selected from $NH_2$, OH, $NHR_5$, and $OR_5$; and
$R_5$ is independently selected from methyl, ethyl, and propyl,
with the provisos that:
when $A_1$ is CH, then $R_{4a}$ is not $NHR_5$ or $OR_5$; and
when $A_2$ is CH, then $R_{4b}$ is not $NHR_5$ or $OR_5$.

2. The compound as recited in claim 1, wherein $A_1$ is CH and $A_2$ is N.

3. The compound as recited in claim 1, wherein $A_1$ is N and $A_2$ is CH.

4. The compound as recited in claim 1, wherein $A_1$ is CH and $A_2$ is CH.

5. The compound as recited in claim 1, wherein $R_{4a}$ and $R_{4b}$ are both $NH_2$.

6. The compound as recited in claim 5, wherein $R_2$ is selected from F and Cl.

7. The compound as recited in claim 1 wherein the compound has structural Formula II:

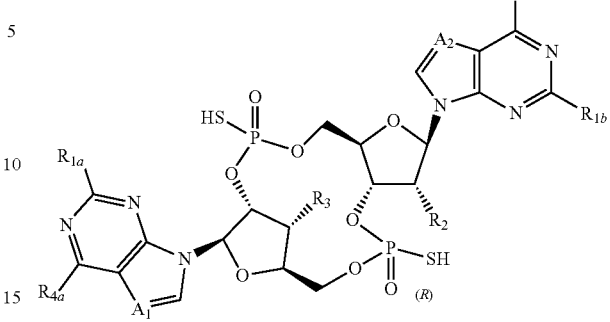

(II)

or a salt, ester, tautomer, or prodrug thereof, wherein:
$A_1$ is CH and $A_2$ is N, or $A_1$ is N and $A_2$ is CH, or $A_1$ is CH and $A_2$ is CH;
$R_{1a}$ and $R_{1b}$ are independently selected from H and $NH_2$;
$R_2$ is selected from OH, F, and Cl;
$R_3$ is OH;
$R_{4a}$ and $R_{4b}$ are independently selected from $NH_2$ and OH.

8. The compound as recited in claim 7, wherein $A_1$ is CH and $A_2$ is N.

9. The compound as recited in claim 7, wherein $A_1$ is N and $A_2$ is CH.

10. The compound as recited in claim 7, wherein $A_1$ is CH and $A_2$ is CH.

11. The compound as recited in claim 7, wherein $R_{4a}$ and $R_{4b}$ are both $NH_2$.

12. The compound as recited in claim 11, wherein $R_2$ is selected from F and Cl.

13. The compound as recited in claim 1, wherein the compound is selected from

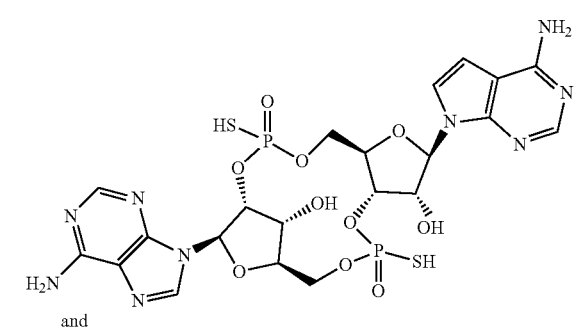

and

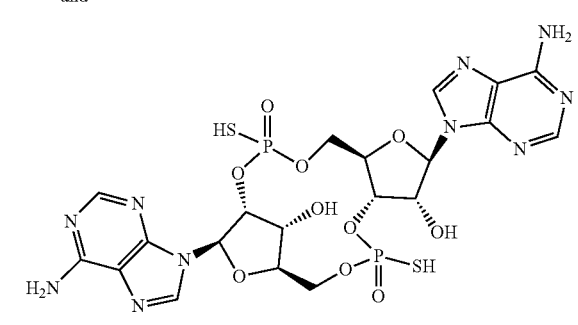

or a salt, ester, tautomer, or prodrug of either of the above compounds.

14. The compound as recited in claim 1, wherein the compound is selected from

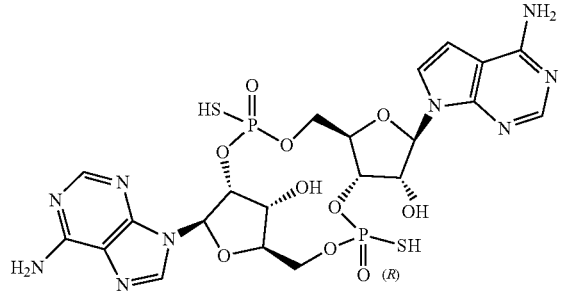

and

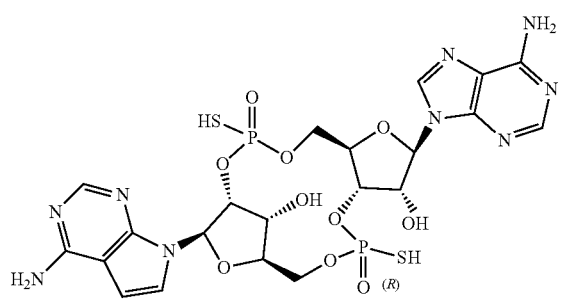

or a salt, ester, tautomer, or prodrug of either of the above compounds.

15. The compound as recited in claim 1, wherein the compound is selected from

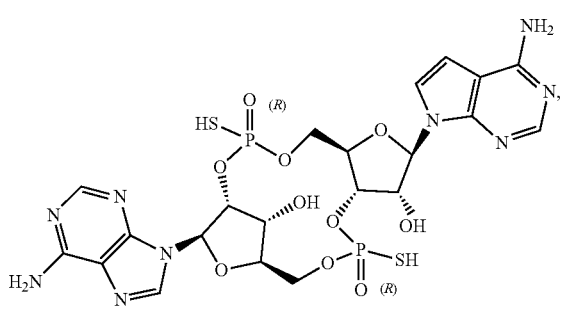

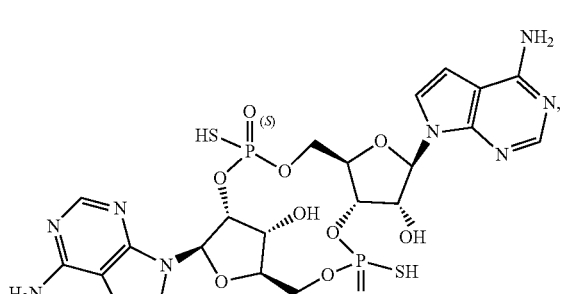

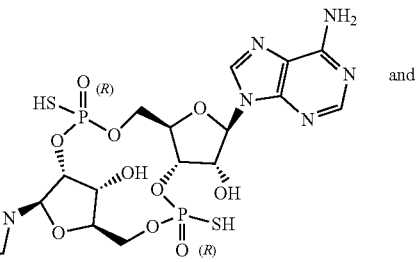

and

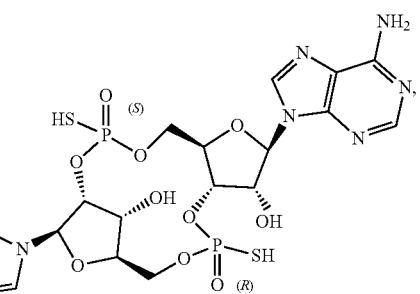

or a salt, ester, tautomer, or prodrug of any of the above compounds.

16. The compound as recited in claim 1, wherein the compound is selected from

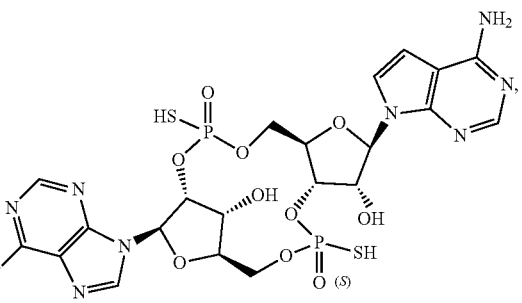

and

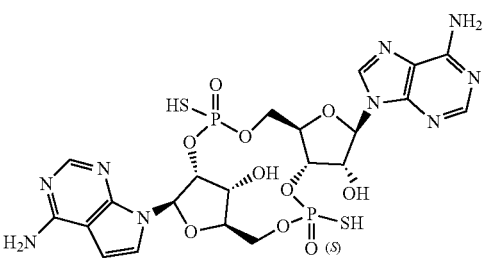

or a salt, ester, tautomer, or prodrug of either of the above compounds.

17. The compound as recited in claim 1, wherein the compound is selected from

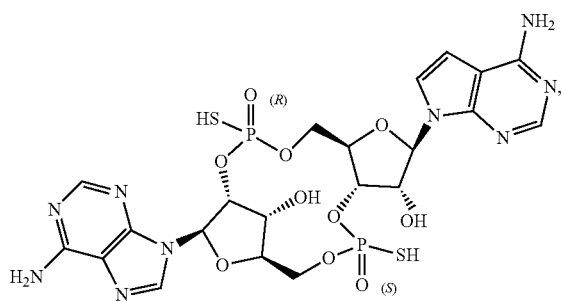

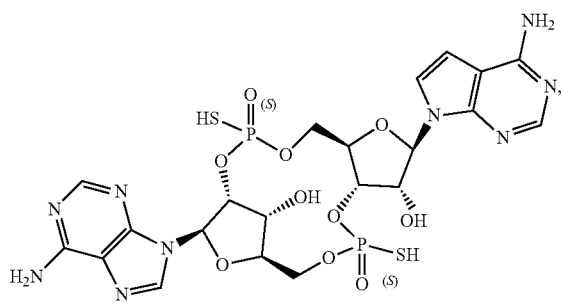

and

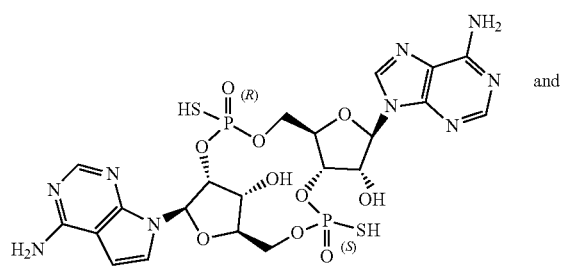

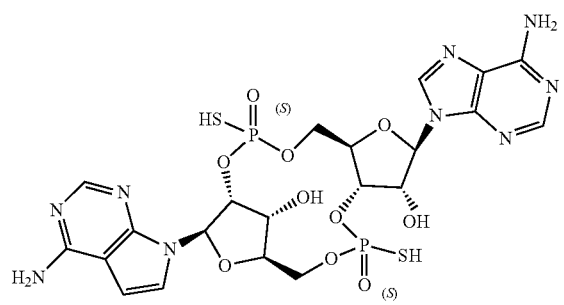

or a salt, ester, tautomer, or prodrug of any of the above compounds.

18. A drug delivery vehicle comprising a compound of Formula I having the structure shown below or a salt, ester, tautomer, or prodrug thereof which is conjugated to a targeting moiety,

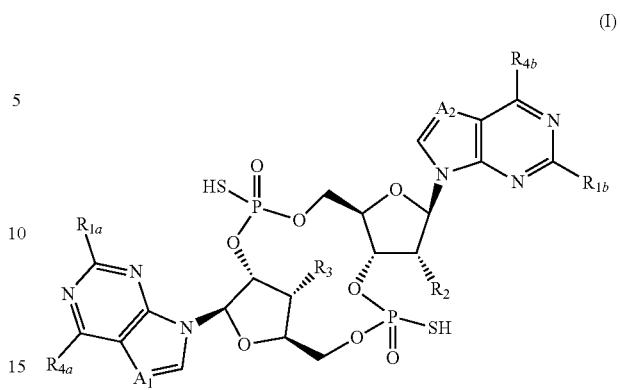

wherein:
$A_1$ and $A_2$ are independently selected from CH and N;
$R_{1a}$ and $R_{1b}$ are independently selected from H and $NH_2$;
$R_2$ is selected from OH, F, Cl, $N_3$, and $NH_2$;
$R_3$ is selected from OH, F, Cl, $N_3$, and $NH_2$;
$R_{4a}$ and $R_{4b}$ are independently selected from $NH_2$, OH, $NHR_5$, and $OR_5$;
$R_5$ is independently selected from methyl, ethyl, and propyl;
with the proviso that:
when $A_1$ is CH, then $R_{4a}$ is not $NHR_5$ or $OR_5$;
when $A_2$ is CH, then $R_{4b}$ is not $NHR_5$ or $OR_5$; and
when $A_1$ and $A_2$ are both N then at least one of $R_2$ and $R_3$ is not OH.

19. A drug delivery vehicle comprising a compound as recited in claim 1 contained within a container moiety.

20. A pharmaceutical composition comprising a compound as recited in claim 1 together with a pharmaceutically acceptable carrier.

21. A method of agonism of STING comprising contacting STING with a compound as recited in claim 1.

22. A method of treatment of a STING-mediated disease comprising the administration of a therapeutically effective amount of a compound as recited in claim 1 to a patient in need thereof.

23. A method for achieving an effect in a patient comprising the administration of a therapeutically effective amount of a compound as recited in claim 1 to a patient, wherein said effect is chosen from induction of transcription of host defense genes, production of a cytokine, release of chemokines, priming of antigen-specific T-cells.

24. A method of inducing STING-dependent type I interferon production in an individual comprising the administration of a sufficient amount of a compound as recited in claim 1 to a patient.

25. A method for administration of a vaccine to a subject comprising:
    (a) administration of an effective amount of said vaccine; and
    (b) administration of an effective amount of a compound as recited in claim 1;
    wherein the efficacy of said vaccine is greater with administration of said compound as recited in claim 1.

26. The compound as recited in claim 1, wherein $R_{1a}$ and $R_{1b}$ are both H.

27. The compound as recited in claim 26, wherein $R_{4a}$ and $R_{4b}$ are independently selected from $NH_2$ and $NHR_5$.

28. The compound as recited in claim 27, wherein $R_{4a}$ and $R_{4b}$ are both $NH_2$.

* * * * *